(12) United States Patent
Hillis et al.

(10) Patent No.: US 8,353,896 B2
(45) Date of Patent: *Jan. 15, 2013

(54) CONTROLLABLE RELEASE NASAL SYSTEM

(75) Inventors: W. Daniel Hillis, Encino, CA (US); Roderick A. Hyde, Livermore, CA (US); Muriel Y. Ishikawa, Livermore, CA (US); Elizabeth A. Sweeney, Seattle, WA (US); Clarence T. Tegreene, Bellevue, WA (US); Richa Wilson, San Francisco, CA (US); Lowell L. Wood, Jr., Livermore, CA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 796 days.

This patent is subject to a terminal disclaimer.

(21) Appl. No.: 11/417,898

(22) Filed: May 4, 2006

(65) Prior Publication Data

US 2010/0256609 A1 Oct. 7, 2010

Related U.S. Application Data

(63) Continuation-in-part of application No. 11/403,230, filed on Apr. 12, 2006, and a continuation-in-part of application No. 10/949,186, filed on Sep. 24, 2004, and a continuation-in-part of application No. 10/827,576, filed on Apr. 19, 2004, and a continuation-in-part of application No. 10/827,578, filed on Apr. 19, 2004, and a continuation-in-part of application No. 10/827,572, filed on Apr. 19, 2004, and a continuation-in-part of application No. 10/827,390, filed on Apr. 19, 2004.

(51) Int. Cl.
*A61K 9/22* (2006.01)
(52) U.S. Cl. ............... 604/890.1; 604/503; 604/516; 604/77; 604/93.01; 604/95.01
(58) Field of Classification Search ............ 604/8, 19, 604/36, 48, 503, 516, 65–66, 77, 93.01, 94.01, 604/95.01, 294, 303, 278, 275; 128/200.24, 128/204.12–204.13, 206.11
See application file for complete search history.

(56) References Cited

U.S. PATENT DOCUMENTS 3,391,697 A 7/1968 Greatbatch
(Continued)

FOREIGN PATENT DOCUMENTS

CN 998102717 10/2001
(Continued)

OTHER PUBLICATIONS

Christensen, Bill; "Propulsion System for 'Fantastic Voyage' Robot"; Technovelgy.com; pp. 1-4; Technovelgy.com; located http://www.technovelgy.com/ct/Science-Fiction-News.asp?NewsNum=811; printed on Jan. 4, 2007.

(Continued)

*Primary Examiner* — Quynh-Nhu H Vu
(74) *Attorney, Agent, or Firm* — Suiter Swantz pc llo

(57) ABSTRACT

Embodiments of devices and system for controllable nasal delivery of materials are described. Methods of use of such devices and system and software for controlling the operation of such devices and systems are also disclosed.

16 Claims, 37 Drawing Sheets

U.S. PATENT DOCUMENTS

| | | |
|---|---|---|
| 3,821,469 A | 6/1974 | Whetstone et al. |
| 3,837,339 A | 9/1974 | Aisenberg et al. |
| 3,941,127 A | 3/1976 | Froning |
| 3,983,474 A | 9/1976 | Kuipers |
| 4,054,881 A | 10/1977 | Raab |
| 4,119,900 A | 10/1978 | Kremnitz |
| 4,202,349 A | 5/1980 | Jones |
| 4,262,306 A | 4/1981 | Renner |
| 4,267,831 A | 5/1981 | Aguilar |
| 4,314,251 A | 2/1982 | Raab |
| 4,317,078 A | 2/1982 | Weed et al. |
| 4,339,953 A | 7/1982 | Iwasaki |
| 4,367,741 A | 1/1983 | Michaels |
| 4,396,885 A | 8/1983 | Constant |
| 4,403,321 A | 9/1983 | Krüger |
| 4,418,422 A | 11/1983 | Richter et al. |
| 4,431,005 A | 2/1984 | McCormick |
| 4,583,190 A | 4/1986 | Salb |
| 4,585,652 A | 4/1986 | Miller et al. |
| 4,628,928 A | 12/1986 | Lowell |
| 4,638,798 A | 1/1987 | Shelden et al. |
| 4,642,786 A | 2/1987 | Hansen |
| 4,651,732 A | 3/1987 | Frederick |
| 4,658,214 A | 4/1987 | Petersen |
| 4,714,460 A | 12/1987 | Calderon |
| 4,717,381 A | 1/1988 | Papantonakos |
| 4,733,661 A | 3/1988 | Palestrant |
| 4,750,488 A | 6/1988 | Wuchinich et al. |
| 4,763,667 A | 8/1988 | Manzo |
| 4,769,006 A | 9/1988 | Papantonakos |
| 4,771,772 A | 9/1988 | DeWitt |
| 4,795,434 A | 1/1989 | Kujawski |
| 4,800,898 A | 1/1989 | Hess et al. |
| 4,805,615 A | 2/1989 | Carol |
| 4,817,601 A | 4/1989 | Roth et al. |
| 4,871,351 A | 10/1989 | Feingold |
| 4,889,526 A | 12/1989 | Rauscher et al. |
| 4,905,689 A | 3/1990 | Stack et al. |
| 4,943,296 A | 7/1990 | Funakubo et al. |
| 4,944,659 A | 7/1990 | Labbe et al. |
| 4,962,453 A | 10/1990 | Pong et al. |
| 4,994,071 A | 2/1991 | MacGregor |
| 5,019,372 A | 5/1991 | Folkman et al. |
| 5,031,109 A | 7/1991 | Gloton |
| 5,051,906 A | 9/1991 | Evans, Jr. et al. |
| 5,078,140 A | 1/1992 | Kwoh |
| 5,086,401 A | 2/1992 | Glassman et al. |
| 5,153,827 A | 10/1992 | Coutre et al. |
| 5,165,064 A | 11/1992 | Mattaboni |
| 5,176,638 A | 1/1993 | Don Michael |
| 5,188,111 A | 2/1993 | Yates et al. |
| 5,204,814 A | 4/1993 | Noonan et al. |
| 5,234,457 A | 8/1993 | Andersen |
| 5,269,303 A | 12/1993 | Wernicke et al. |
| 5,279,607 A | 1/1994 | Schentag et al. |
| 5,310,404 A | 5/1994 | Gyory et al. |
| 5,313,835 A | 5/1994 | Dunn |
| 5,314,451 A | 5/1994 | Mulier |
| 5,321,614 A | 6/1994 | Ashworth |
| 5,335,657 A | 8/1994 | Terry, Jr. et al. |
| 5,337,732 A | 8/1994 | Grundfest et al. |
| 5,338,625 A | 8/1994 | Bates et al. |
| 5,339,051 A | 8/1994 | Koehler et al. |
| 5,353,807 A | 10/1994 | DeMarco |
| 5,374,285 A | 12/1994 | Vaiani et al. |
| 5,381,786 A | 1/1995 | Spears |
| 5,386,741 A | 2/1995 | Rennex |
| 5,395,390 A | 3/1995 | Simon et al. |
| 5,398,670 A | 3/1995 | Ortiz et al. |
| 5,403,311 A | 4/1995 | Abele et al. |
| 5,411,551 A | 5/1995 | Winston et al. |
| 5,437,660 A | 8/1995 | Johnson et al. |
| 5,476,450 A | 12/1995 | Ruggio |
| 5,497,147 A | 3/1996 | Arms et al. |
| 5,502,638 A | 3/1996 | Takenaka |
| 5,507,287 A | 4/1996 | Palcic et al. |
| 5,522,394 A | 6/1996 | Zurbrügg |
| 5,551,953 A * | 9/1996 | Lattin et al. .................... 604/20 |
| 5,554,914 A | 9/1996 | Miyazawa |
| 5,569,968 A | 10/1996 | Lal et al. |
| 5,574,347 A | 11/1996 | Neubauer |
| 5,589,932 A | 12/1996 | Garcia-Rubio et al. |
| 5,593,434 A | 1/1997 | Williams |
| 5,599,324 A | 2/1997 | McAlister et al. |
| 5,610,488 A | 3/1997 | Miyazawa |
| 5,624,398 A | 4/1997 | Smith et al. |
| 5,632,754 A | 5/1997 | Farley et al. |
| 5,643,296 A | 7/1997 | Hundertmark et al. |
| 5,662,587 A | 9/1997 | Grundfest et al. |
| 5,669,874 A | 9/1997 | Feiring |
| 5,670,329 A | 9/1997 | Oberhardt |
| 5,674,276 A | 10/1997 | Andersen et al. |
| 5,688,269 A | 11/1997 | Newton et al. |
| 5,695,457 A | 12/1997 | St. Goar et al. |
| 5,697,967 A | 12/1997 | Dinh et al. |
| 5,702,432 A | 12/1997 | Chen et al. |
| 5,705,293 A | 1/1998 | Hobson |
| 5,728,089 A | 3/1998 | Lal et al. |
| 5,735,276 A | 4/1998 | Lemelson |
| 5,737,279 A | 4/1998 | Carter |
| 5,758,298 A | 5/1998 | Guldner |
| 5,782,798 A | 7/1998 | Rise |
| 5,804,563 A | 9/1998 | Still et al. |
| 5,807,395 A | 9/1998 | Mulier et al. |
| 5,819,736 A | 10/1998 | Avny et al. |
| 5,827,190 A | 10/1998 | Palcic et al. |
| 5,830,179 A | 11/1998 | Mikus et al. |
| 5,830,207 A | 11/1998 | Leeb et al. |
| 5,831,012 A | 11/1998 | Nilsson et al. |
| 5,833,603 A | 11/1998 | Kovacs et al. |
| 5,843,139 A | 12/1998 | Goedeke et al. |
| 5,855,801 A | 1/1999 | Lin et al. |
| 5,865,754 A | 2/1999 | Sevick-Muraca et al. |
| 5,873,835 A | 2/1999 | Hastings et al. |
| 5,908,027 A | 6/1999 | Butterfield et al. |
| 5,921,982 A | 7/1999 | Lesh et al. |
| 5,947,119 A * | 9/1999 | Reznick .................. 128/204.12 |
| 5,951,600 A | 9/1999 | Lemelson |
| 5,954,675 A | 9/1999 | Dellagatta |
| 5,964,773 A | 10/1999 | Greenstein |
| 6,004,269 A | 12/1999 | Crowley et al. |
| 6,016,449 A | 1/2000 | Fischell et al. |
| 6,019,729 A | 2/2000 | Itoigawa et al. |
| 6,022,316 A | 2/2000 | Eppstein et al. |
| 6,053,873 A | 4/2000 | Govari et al. |
| 6,086,528 A | 7/2000 | Adair |
| 6,102,845 A | 8/2000 | Woodard et al. |
| 6,108,597 A | 8/2000 | Kirchner et al. |
| 6,111,520 A | 8/2000 | Allen et al. |
| 6,128,538 A | 10/2000 | Fischell et al. |
| 6,134,474 A | 10/2000 | Fischell et al. |
| 6,149,603 A | 11/2000 | Parker |
| 6,159,230 A | 12/2000 | Samuels |
| 6,164,284 A | 12/2000 | Schulman et al. |
| 6,170,488 B1 | 1/2001 | Spillman, Jr. et al. |
| 6,175,757 B1 | 1/2001 | Watkins et al. |
| 6,179,789 B1 | 1/2001 | Tu et al. |
| 6,185,452 B1 | 2/2001 | Schulman et al. |
| 6,186,986 B1 | 2/2001 | Berg et al. |
| 6,187,599 B1 | 2/2001 | Asher et al. |
| 6,197,013 B1 | 3/2001 | Reed et al. |
| 6,219,577 B1 | 4/2001 | Brown, III et al. |
| 6,221,099 B1 | 4/2001 | Andersen et al. |
| 6,240,312 B1 | 5/2001 | Alfano et al. |
| 6,240,316 B1 | 5/2001 | Richmond et al. |
| 6,248,345 B1 | 6/2001 | Goldenheim et al. |
| 6,249,076 B1 | 6/2001 | Madden et al. |
| 6,255,361 B1 | 7/2001 | Rajagopalan et al. |
| 6,255,793 B1 | 7/2001 | Peless et al. |
| 6,263,245 B1 | 7/2001 | Snell |
| 6,278,379 B1 | 8/2001 | Allen et al. |
| 6,280,386 B1 | 8/2001 | Alfano et al. |
| 6,289,270 B1 | 9/2001 | Baumgarten |
| 6,295,990 B1 | 10/2001 | Lewis et al. |
| 6,296,638 B1 | 10/2001 | Davison et al. |
| 6,322,532 B1 | 11/2001 | D'Sa et al. |
| 6,337,997 B1 | 1/2002 | Rise |

| Patent No. | Date | Name |
|---|---|---|
| 6,372,248 B1 | 4/2002 | Qin et al. |
| 6,383,162 B1 | 5/2002 | Sugarbaker |
| 6,384,741 B1 | 5/2002 | O'Leary, Sr. |
| 6,385,472 B1 | 5/2002 | Hall et al. |
| 6,398,280 B1 | 6/2002 | Parker et al. |
| 6,400,980 B1 | 6/2002 | Lemelson |
| 6,402,678 B1 | 6/2002 | Fischell et al. |
| 6,409,674 B1 | 6/2002 | Brockway et al. |
| 6,417,641 B2 | 7/2002 | Peless et al. |
| 6,431,171 B1 | 8/2002 | Burton |
| 6,436,120 B1 | 8/2002 | Meglin |
| 6,442,413 B1 | 8/2002 | Silver |
| 6,450,937 B1 | 9/2002 | Mercereau et al. |
| 6,453,199 B1 | 9/2002 | Kobozev |
| 6,464,687 B1 | 10/2002 | Ishikawa et al. |
| 6,475,639 B2 | 11/2002 | Shahinpoor et al. |
| 6,490,483 B2 | 12/2002 | Willis |
| 6,491,618 B1 | 12/2002 | Ganz |
| 6,493,607 B1 | 12/2002 | Bourne et al. |
| 6,497,714 B1 | 12/2002 | Ishikawa et al. |
| 6,500,174 B1 | 12/2002 | Maguire et al. |
| 6,512,949 B1 | 1/2003 | Combs et al. |
| 6,512,950 B2 | 1/2003 | Li et al. |
| 6,514,237 B1 | 2/2003 | Maseda |
| 6,530,950 B1 | 3/2003 | Alvarado et al. |
| 6,547,723 B1 | 4/2003 | Ouchi |
| 6,547,825 B1 | 4/2003 | Shimizu et al. |
| 6,548,982 B1 | 4/2003 | Papanikolopoulos et al. |
| 6,554,798 B1 | 4/2003 | Mann et al. |
| 6,575,969 B1 | 6/2003 | Rittman, III et al. |
| 6,585,763 B1 | 7/2003 | Keilman et al. |
| 6,591,137 B1 | 7/2003 | Fischell et al. |
| 6,592,567 B1 | 7/2003 | Levin et al. |
| 6,597,954 B1 | 7/2003 | Pless et al. |
| 6,607,553 B1 | 8/2003 | Healy et al. |
| 6,612,982 B1 | 9/2003 | Ouchi |
| 6,616,676 B2 | 9/2003 | Bashiri et al. |
| 6,623,519 B2 | 9/2003 | Edwin et al. |
| 6,632,216 B2 | 10/2003 | Houzego et al. |
| 6,638,273 B1 | 10/2003 | Farley et al. |
| 6,648,908 B2 | 11/2003 | Dobak, III et al. |
| 6,666,860 B1 | 12/2003 | Takahashi |
| 6,669,683 B2 | 12/2003 | Santini, Jr. et al. |
| 6,673,042 B1 | 1/2004 | Samson et al. |
| 6,673,363 B2 | 1/2004 | Luo et al. |
| 6,679,893 B1 | 1/2004 | Tran |
| 6,709,388 B1 | 3/2004 | Mosse et al. |
| 6,711,423 B2 | 3/2004 | Colvin, Jr. |
| 6,712,835 B2 | 3/2004 | Mazzocchi et al. |
| 6,719,684 B2 | 4/2004 | Kim et al. |
| 6,723,092 B2 | 4/2004 | Brown et al. |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,743,211 B1 | 6/2004 | Prausnitz et al. |
| 6,754,536 B2 | 6/2004 | Swoyer et al. |
| 6,755,802 B2 | 6/2004 | Bell |
| 6,755,803 B1 | 6/2004 | Le et al. |
| 6,764,441 B2 | 7/2004 | Chiel et al. |
| 6,770,071 B2 | 8/2004 | Woloszko et al. |
| 6,773,429 B2 | 8/2004 | Sheppard, Jr. et al. |
| 6,776,165 B2 | 8/2004 | Jin |
| 6,797,522 B1 | 9/2004 | Still et al. |
| 6,802,811 B1 | 10/2004 | Slepian |
| 6,816,632 B1 | 11/2004 | Slice |
| 6,824,508 B2 | 11/2004 | Kim et al. |
| 6,824,510 B2 | 11/2004 | Kim et al. |
| 6,824,561 B2 | 11/2004 | Soykan et al. |
| 6,834,118 B2 | 12/2004 | Kim |
| 6,849,183 B2 | 2/2005 | Gorsuch et al. |
| 6,855,115 B2 | 2/2005 | Fonseca et al. |
| 6,860,867 B2 | 3/2005 | Seward et al. |
| 6,861,001 B2 | 3/2005 | Lee et al. |
| 6,866,626 B2 | 3/2005 | Long et al. |
| 6,869,430 B2 | 3/2005 | Balbierz et al. |
| 6,875,209 B2 | 4/2005 | Zvuloni et al. |
| 6,882,881 B1 | 4/2005 | Lesser et al. |
| 6,889,091 B2 | 5/2005 | Hine et al. |
| 6,890,303 B2 | 5/2005 | Fitz |
| 6,898,464 B2 | 5/2005 | Edell et al. |
| 6,911,004 B2 | 6/2005 | Kim et al. |
| 6,911,496 B2 | 6/2005 | Rhee et al. |
| 6,920,359 B2 | 7/2005 | Meadows et al. |
| 6,921,413 B2 | 7/2005 | Mahadevan-Jansen et al. |
| 6,925,357 B2 | 8/2005 | Wang et al. |
| 6,929,636 B1 | 8/2005 | Von Alten |
| 6,936,003 B2 | 8/2005 | Iddan |
| 6,939,290 B2 | 9/2005 | Iddan |
| 6,939,376 B2 | 9/2005 | Shulze et al. |
| 6,950,707 B2 | 9/2005 | Whitehurst |
| 6,953,589 B1 | 10/2005 | Trautman et al. |
| 6,958,034 B2 | 10/2005 | Iddan |
| 6,959,215 B2 | 10/2005 | Gliner et al. |
| 6,960,227 B2 | 11/2005 | Jones et al. |
| 6,963,792 B1 | 11/2005 | Green |
| 6,984,205 B2 | 1/2006 | Gazdzinski |
| 6,984,952 B2 | 1/2006 | Peless et al. |
| 6,991,617 B2 | 1/2006 | Hektner et al. |
| 7,003,352 B1 | 2/2006 | Whitehurst |
| 7,013,177 B1 | 3/2006 | Whitehurst et al. |
| 7,020,531 B1 | 3/2006 | Frey et al. |
| 7,027,134 B1 | 4/2006 | Garcia-Rubio et al. |
| 7,037,343 B2 | 5/2006 | Imran |
| 7,039,453 B2 | 5/2006 | Mullick et al. |
| 7,042,184 B2 | 5/2006 | Oleynikov et al. |
| 7,044,911 B2 | 5/2006 | Drinan et al. |
| RE39,133 E | 6/2006 | Clayton et al. |
| 7,066,180 B2 | 6/2006 | Aylsworth et al. |
| 7,083,578 B2 | 8/2006 | Lewkowicz et al. |
| 7,101,386 B2 | 9/2006 | Dobak, III |
| 7,115,109 B2 | 10/2006 | Gerdts et al. |
| 7,118,531 B2 | 10/2006 | Krill |
| 7,125,382 B2 | 10/2006 | Zhou et al. |
| 7,131,979 B2 | 11/2006 | DiCarlo et al. |
| 7,160,258 B2 | 1/2007 | Imran et al. |
| 7,171,285 B2 | 1/2007 | Kim et al. |
| 7,181,261 B2 | 2/2007 | Silver et al. |
| 7,195,641 B2 | 3/2007 | Palmaz et al. |
| 7,212,110 B1 | 5/2007 | Martin et |
| 7,214,182 B2 | 5/2007 | Shimizu et al. |
| 7,228,162 B2 | 6/2007 | Ward et al. |
| 7,236,821 B2 | 6/2007 | Cates et al. |
| 7,245,954 B2 | 7/2007 | Glukhovsky |
| 7,297,113 B1 | 11/2007 | Russell et al. |
| 7,341,577 B2 | 3/2008 | Gill |
| 7,365,509 B2 | 4/2008 | Park et al. |
| 7,365,614 B2 | 4/2008 | McCorquodale et al. |
| 7,383,071 B1 | 6/2008 | Russell et al. |
| 7,398,734 B1 | 7/2008 | Jean |
| 7,451,537 B2 | 11/2008 | Liu et al. |
| 7,486,967 B2 | 2/2009 | Pan et al. |
| 7,572,228 B2 | 8/2009 | Wolinsky et al. |
| 7,596,403 B2 | 9/2009 | Horn |
| 7,625,338 B2 | 12/2009 | Gilad et al. |
| 7,684,840 B2 | 3/2010 | Palti |
| 7,713,196 B2 | 5/2010 | Baker, Jr. |
| 7,736,300 B2 | 6/2010 | Ziegler et al. |
| 7,744,542 B2 | 6/2010 | Piaget et al. |
| 7,801,626 B2 | 9/2010 | Moser |
| 7,840,271 B2 | 11/2010 | Kieval et al. |
| 7,857,767 B2 | 12/2010 | Ferren et al. |
| 2001/0029348 A1 | 10/2001 | Willis |
| 2001/0051766 A1 | 12/2001 | Gazdzinski |
| 2002/0026188 A1 | 2/2002 | Balbierz et al. |
| 2002/0065509 A1 | 5/2002 | Lebel et al. |
| 2002/0068080 A1 | 6/2002 | Lerner |
| 2002/0090388 A1 | 7/2002 | Humes et al. |
| 2002/0103417 A1 | 8/2002 | Gazdzinski |
| 2002/0116029 A1 | 8/2002 | Miller et al. |
| 2002/0116034 A1 | 8/2002 | Miller et al. |
| 2002/0120263 A1 | 8/2002 | Brown et al. |
| 2002/0147480 A1 | 10/2002 | Mamayek |
| 2002/0156462 A1 | 10/2002 | Stultz |
| 2002/0165592 A1 | 11/2002 | Glukhovsky et al. |
| 2002/0169436 A1 | 11/2002 | Gurm et al. |
| 2002/0171385 A1 | 11/2002 | Kim et al. |
| 2002/0188323 A1 | 12/2002 | Penner et al. |
| 2002/0193679 A1 | 12/2002 | Malave et al. |

| | | |
|---|---|---|
| 2002/0193874 A1 | 12/2002 | Crowley |
| 2002/0198470 A1 | 12/2002 | Imran et al. |
| 2002/0198521 A1 | 12/2002 | Maguire |
| 2002/0198604 A1 | 12/2002 | Schulman et al. |
| 2003/0004403 A1 | 1/2003 | Drinan et al. |
| 2003/0023150 A1 | 1/2003 | Yokoi et al. |
| 2003/0024534 A1 | 2/2003 | Silvestri et al. |
| 2003/0040704 A1 | 2/2003 | Dorros et al. |
| 2003/0060723 A1 | 3/2003 | Joo et al. |
| 2003/0065250 A1 | 4/2003 | Chiel et al. |
| 2003/0065358 A1 | 4/2003 | Frecker et al. |
| 2003/0069475 A1 | 4/2003 | Banik et al. |
| 2003/0069523 A1 | 4/2003 | Williams et al. |
| 2003/0093031 A1 | 5/2003 | Long et al. |
| 2003/0151524 A1 | 8/2003 | Clark |
| 2003/0152823 A1 | 8/2003 | Heller |
| 2003/0153866 A1 | 8/2003 | Long et al. |
| 2003/0158584 A1 | 8/2003 | Cates et al. |
| 2003/0163177 A1 | 8/2003 | Eggers et al. |
| 2003/0167000 A1 | 9/2003 | Mullick et al. |
| 2003/0191430 A1 | 10/2003 | D'Andrea et al. |
| 2003/0214579 A1 | 11/2003 | Iddan |
| 2003/0214580 A1 | 11/2003 | Iddan |
| 2003/0220556 A1 | 11/2003 | Porat et al. |
| 2004/0008853 A1 | 1/2004 | Pelrine et al. |
| 2004/0018508 A1 | 1/2004 | Friedman |
| 2004/0019374 A1 | 1/2004 | Hojeibane et al. |
| 2004/0034332 A1 | 2/2004 | Uhland |
| 2004/0064093 A1 | 4/2004 | Hektner et al. |
| 2004/0073177 A1 | 4/2004 | Hickle |
| 2004/0073190 A1 | 4/2004 | Deem et al. |
| 2004/0092825 A1 | 5/2004 | Madar et al. |
| 2004/0097805 A1 | 5/2004 | Verard et al. |
| 2004/0097819 A1 | 5/2004 | Duarte |
| 2004/0098030 A1 | 5/2004 | Makower et al. |
| 2004/0111019 A1 | 6/2004 | Long |
| 2004/0133147 A1 | 7/2004 | Woo |
| 2004/0138517 A1 | 7/2004 | Osorio et al. |
| 2004/0147939 A1 | 7/2004 | Rabkin et al. |
| 2004/0148034 A1 | 7/2004 | Kagan et al. |
| 2004/0152988 A1 | 8/2004 | Weirich |
| 2004/0162469 A1 | 8/2004 | Imran |
| 2004/0162501 A1 | 8/2004 | Imran |
| 2004/0176664 A1 | 9/2004 | Iddan |
| 2004/0193010 A1 | 9/2004 | Fujimori et al. |
| 2004/0199246 A1 | 10/2004 | Chu et al. |
| 2004/0225325 A1 | 11/2004 | Bonutti |
| 2004/0225326 A1 | 11/2004 | Weiner et al. |
| 2004/0260391 A1 | 12/2004 | Santini, Jr. et al. |
| 2004/0267240 A1 | 12/2004 | Gross et al. |
| 2005/0004474 A1 | 1/2005 | Iddan |
| 2005/0004553 A1 | 1/2005 | Douk |
| 2005/0021023 A1 | 1/2005 | Guglielmi et al. |
| 2005/0027236 A1 | 2/2005 | Douk |
| 2005/0043583 A1 | 2/2005 | Killmann et al. |
| 2005/0058701 A1 | 3/2005 | Gross et al. |
| 2005/0062562 A1 | 3/2005 | Ries |
| 2005/0065592 A1 | 3/2005 | Holzer |
| 2005/0069925 A1 | 3/2005 | Ford et al. |
| 2005/0079132 A1 | 4/2005 | Wang et al. |
| 2005/0107870 A1 | 5/2005 | Wang et al. |
| 2005/0113460 A1 | 5/2005 | Glick |
| 2005/0121411 A1 | 6/2005 | Cohen |
| 2005/0126916 A1 | 6/2005 | Lockard et al. |
| 2005/0149170 A1 | 7/2005 | Tassel et al. |
| 2005/0151524 A1 | 7/2005 | Sae-Ueng et al. |
| 2005/0171418 A1 | 8/2005 | Lin |
| 2005/0171434 A1 | 8/2005 | Madden et al. |
| 2005/0177223 A1 | 8/2005 | Palmaz |
| 2005/0182482 A1 | 8/2005 | Wang et al. |
| 2005/0203613 A1 | 9/2005 | Arney et al. |
| 2005/0215911 A1 | 9/2005 | Alfano et al. |
| 2005/0216074 A1 | 9/2005 | Sahatjian et al. |
| 2005/0221529 A1 | 10/2005 | Bang et al. |
| 2005/0228259 A1 | 10/2005 | Glukhovsky et al. |
| 2005/0234393 A1 | 10/2005 | Wood, Jr. |
| 2005/0234440 A1 | 10/2005 | Wood, Jr. |
| 2005/0238689 A1 | 10/2005 | Carpenter et al. |
| 2005/0272806 A1 | 12/2005 | Falotico et al. |
| 2005/0272974 A1 | 12/2005 | Iddan |
| 2005/0277839 A1 | 12/2005 | Alderman et al. |
| 2005/0278020 A1 | 12/2005 | Wang et al. |
| 2006/0004395 A1 | 1/2006 | Chiel et al. |
| 2006/0009810 A1 | 1/2006 | Mann et al. |
| 2006/0015146 A1 | 1/2006 | Girouard et al. |
| 2006/0037617 A1 | 2/2006 | Walke et al. |
| 2006/0042631 A1 | 3/2006 | Martin et al. |
| 2006/0074479 A1 | 4/2006 | Bailey et al. |
| 2006/0119304 A1 | 6/2006 | Farritor et al. |
| 2006/0152309 A1 | 7/2006 | Mintchev et al. |
| 2006/0167339 A1 | 7/2006 | Gilad et al. |
| 2006/0169294 A1 | 8/2006 | Kaler et al. |
| 2006/0235275 A1 | 10/2006 | Rabinovitz et al. |
| 2006/0252987 A1 | 11/2006 | Hasegawa et al. |
| 2007/0010868 A1* | 1/2007 | Ferren et al. .................. 623/1.15 |
| 2007/0066929 A1* | 3/2007 | Ferren et al. ....................... 604/8 |
| 2007/0088334 A1* | 4/2007 | Hillis et al. ................ 604/891.1 |
| 2007/0156211 A1 | 7/2007 | Ferren et al. |
| 2007/0225634 A1* | 9/2007 | Ferren et al. .................... 604/27 |
| 2008/0033569 A1 | 2/2008 | Ferren et al. |
| 2008/0063703 A1 | 3/2008 | Gross et al. |
| 2008/0103440 A1 | 5/2008 | Ferren et al. |
| 2008/0121054 A1 | 5/2008 | Goldenberg et al. |
| 2008/0241847 A1 | 10/2008 | Hoon et al. |
| 2008/0266106 A1 | 10/2008 | Lim et al. |
| 2009/0062646 A1 | 3/2009 | Creighton, IV et al. |
| 2009/0069821 A1 | 3/2009 | Farritor et al. |
| 2009/0082652 A1 | 3/2009 | Koh et al. |
| 2009/0182388 A1 | 7/2009 | Von Arx et al. |

FOREIGN PATENT DOCUMENTS

| | | |
|---|---|---|
| EP | 1 245 201 A1 | 10/2002 |
| EP | 1 618 831 A2 | 1/2006 |
| EP | 2 163 206 A1 | 3/2010 |
| JP | 2001-506871 | 3/1998 |
| JP | 2002-153569 | 5/2002 |
| JP | 2005-74229 | 3/2005 |
| WO | WO 96/39999 | 12/1996 |
| WO | WO 98/09582 | 3/1998 |
| WO | WO 98/14243 | 4/1998 |
| WO | WO 99/20335 | 4/1999 |
| WO | WO 99/44665 | 9/1999 |
| WO | WO 00/69515 | 11/2000 |
| WO | WO 01/08548 A1 | 2/2001 |
| WO | WO 01/24731 A1 | 4/2001 |
| WO | WO 03/072157 A1 | 9/2003 |
| WO | WO 03/090618 A2 | 11/2003 |
| WO | WO 03/106966 A2 | 12/2003 |
| WO | WO 2004/028335 A2 | 4/2004 |
| WO | WO 2004/058041 A2 | 7/2004 |
| WO | WO 2004/086958 A1 | 10/2004 |
| WO | WO 2005/082248 A1 | 9/2005 |

OTHER PUBLICATIONS

Mohseni, Kamran; "Biomimetic & Bio-Inspired Aerial and Underwater Vehicles"; bearing a date of Sep. 23, 2006; pp. 1-10; printed on Jan. 4, 2007; located at http://enstrophy.colorado.edu/~mohseni/MicroVehicles1.html#UUV1#UUV1.

Murthy, S. Narasimha; Hiremath, Shobha Rani R.; "Physical and Chemical Permeation Enhancers in Transdermal Delivery of Terbutaline Sulphate"; AAPS PharmSciTech; bearing a date of 2001; pp. 1-5; vol. 2001, 2(1); Technical Note 1; located at http://www.pharmscitech.com/.

"Researchers: Squid-Inspired Vortex Generators Could Mean Better Propulsion for Unmanned Underwater Vehicles"; UnderwaterTimes.com; Dec. 12, 2006; pp. 1-2; UnderwaterTimes.com; printed on Jan. 4, 2007; located at http://www.underwatertimes.com/print.php?article_id=51030782641.

Senel, Sevda; Hincal, A. Atilla; "Drug permeation enhancement via buccal route: possibilities and limitations"; Journal of Controlled Release; bearing a date of 2001; pp. 133-144; vol. 72 (2001); Elsevier; located at www.elsevier.com/locate/jconrel.

UK Intellectual Property Office Examination Report Under Section 18(3); App. No. GB0706802.6; bearing a date of Dec. 1, 2008; pp. 1-2.

UK Intellectual Property Office Examination Report Under Section 18(3); App. No. GB0821519.6; Nov. 12, 2009; 1-4.
UK Intellectual Property Office Examination Report Under Section 18(3); App. No. GB0821526.1; Nov. 11, 2009; 1-5.
UK Intellectual Property Office Examination Report Under Section 18(3), App. No. GB0821523.8; Jul. 2, 2009; pp. 1-2.
UK Intellectual Property Office Examination Report Under Section 18(3); App. No. GB0706802.6; Nov. 23, 2009; pp. 1-2.
U.S. Appl. No. 11/485,619, Hillis et al.
U.S. Appl. No. 11/478,368, Ferren et al.
U.S. Appl. No. 11/541,492, Jung et al.
U.S. Appl. No. 11/541,452, Jung et al.
U.S. Appl. No. 11/541,448, Jung et al.
Bialek, William; Rieke, Fred; De Ruyter Van Steveninck, Rob R.; Warland, David; "Reading a Neural Code"; Science; bearing a date of Jun. 28, 1991; pp. 1854-1857; vol. 252.
Bucher, Volker; Graf, Michael; Stelzle, Martin; Nisch, Wilfried; "Low-Impedance Thin-Film Polycrystalline Silicon Microelectrodes for Extracellular Stimulation and Recording"; Biosensors and Bioelectronics; bearing a date of 1999; pp. 639-649; vol. 14; Elsevier Science S.A.; located at: www.elsevier.com/locate/bios.
Butson, Christopher R.; McIntyre, Cameron C.; "Role of Electrode Design on the Volume of Tissue Activated During Deep Brain Stimulation"; Journal of Neural Engineering; bearing a date of 2006; vol. 3; pp. 1-8; IOP Publishing Ltd.
Chang, Suk Tai; Paunov, Vesselin N.; Petsev, Dimiter N.; Velev, Orlin D.; "Articles: Remotely Powered Self-Propelling Particles and Micropumps Based on Miniature Diodes"; Nature Materials; bearing a date of 2007; pp. 1-6; Nature Publishing Group; located at: www.nature.com/naturematerials.
U.S. Appl. No. 11/541,378, Jung et al.
U.S. Appl. No. 11/541,377, Jung et al.
U.S. Appl. No. 11/526,203, Jung et al.
U.S. Appl. No. 11/526,201, Jung et al.
U.S. Appl. No. 11/526,144, Jung et al.
U.S. Appl. No. 11/526,089, Jung et al.
U.S. Appl. No. 11/455,010, Jung et al.
U.S. Appl. No. 11/454,343, Jung et al.
Cui, Xinyan; Hetke, Jamille F.; Wiler, James A.; Anderson, David J.; Martin, David C.; "Electrochemical Deposition and Characterization of Conducting Polymer Polypyrrole/PPS on Multichannel Neural Probes"; Sensors and Actuators A Physical; bearing a date of 2001; pp. 8-18; vol. 93; Elsevier Science B.V.; located at: www.elsevier.com/locate/sna.
Dillier, Norbert; Lai, Wai Kong; Almqvist, Bengt; Frohne, Carolin; Müller-Deile, Joachim; Stecker, Matthias; Von Wallenberg, Ernst; "Measurement of the Electrically Evoked Compound Action Potential Via a Neural Response Telemetry System"; Annals of Otology Rhinology and Laryngology; bearing a date of May 2002; pp. 407-414; vol. 111, No. 5; Annals Publishing Company.
Donoghue, John P.; "Review: Connecting Cortex to Machines: Recent Advances in Brain Interfaces"; Nature Neuroscience Supplement; bearing a date on Nov. 2002; pp. 1085-1088; vol. 5; Nature Publishing Group; located at: http://www.nature.com/natureneuroscience.
Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.
Fiaccabrino, G.C.; Tang, X.-M.; Skinner, N.; De Rooij, N.F.; Koudelka-Hep, M.; "Electrochemical Characterization of Thin-Film Carbon Interdigitated Electrode Arrays"; Analytica Chimica Acta; bearing a date of 1996; pp. 155-160; vol. 326; Elsevier Science B.V.
Gitter, Alfred H.; Fromm, Michael; Schulzke, Jörg-Dieter; "Impedance Analysis for the Determination of Epithelial and Subepithelial Resistance in Intestinal Tissues"; Journal of Biochemical and Biophysical Methods, bearing a date of 1998; pp. 35-46; vol. 37; Elsevier Science B.V.
Goda, Yukiko; Colicos, Michael A.; "Protocol: Photoconductive Stimulation of Neurons Cultured on Silicon Wafers"; Nature Protocols; bearing a date of 2006; pp. 461-467; vol. 1, No. 1; Nature Publishing Group; located at: http://www.nature.com/natureprotocols.

Gozani, Shai N.; Miller, John P.; "Optimal Discrimination and Classification of Neuronal Action Potential Waveforms from Multiunit, Multichannel Recordings Using Software-Based Linear Filters"; IEEE Transactions on Biomedical Engineering; bearing a date of Apr. 1994; pp. 358-372; vol. 41, No. 4; IEEE.
Gray, Charles M.; Maldonado, Pedro E.; Wilson, Mathew; McNaughton, Bruce; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; vol. 63; Elsevier Science B.V.
Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.
Hofmann, U.G.; Folkers, A.; Mösch, F.; Höhl, D.; Kindlundh, M.; Norlin, P.; "A 64(128)-Channel Multisite Neuronal Recording System"; bearing a date of 2002; pp. 1-4.
Inmann, Andreas; Haugland, Morten; Haase, Jens; Biering-Sørensen, Fin; Sinkjaer, Thomas; "NeuroReport: Signals from Skin Mechanoreceptors used in Control of a Hand Grasp Neuroprosthesis"; Motor Systems; bearing a date of Sep. 17, 2001; pp. 2817-2819; vol. 12, No. 13; Lippincott Williams & Wilkins.
Janders, M.; Egert, U.; Stelze, M.; Nisch, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE.
"Japanese Researchers Unveil Medical Mini Robot"; Yahoo! News; bearing a date of Mar. 8, 2007; pp. 1-2; Yahoo! Inc.; located at: http://news.yahoo.com/s/afp/20070308/hl_afp/afplifestyleshealthscience; printed on Mar. 8, 2007.
Ji, Jin; Najafi, Khalil, Wise, Kensall D.; "A Low-Noise Demultiplexing System for Active Multichannel Microelectrode Arrays"; IEEE Transactions of Biomedical Engineering; bearing a date of Jan. 1991; pp. 77-81; vol. 38, No. 1; IEEE.
Kennedy, P.R.; Bakay, R.A.E.; Moore, M.M.; Adams, K.; Goldwaithe, J.; "Direct Control of a Computer from the Human Central Nervous System"; IEEE Transactions on Rehabilitation Engineering; bearing a date of Jun. 2000; pp. 198-202; vol. 8, No. 2; IEEE.
Kobetic, Rudi; Triolo, Ronald J.; Uhlir, James P.; Bieri, Carole; Wibowo, Michael; Polando, Gordie; Marsolais, E. Byron; Davis Jr., John A.; Ferguson, Kathleen A.; Sharma, Mukut; "Implanted Functional Electrical Stimulation System for Mobility in Paraplegia: A Follow-Up Case Report"; IEEE Transactions on Rehabilitation Engineering; bearing a date of Dec. 1999; pp. 390-398; vol. 7, No. 4; IEEE.
Loeb, Gerald E.; Peck, Raymond A.; Moore, William H.; Hood, Kevin; "Bion System for Distributed Neural Prosthetic Interfaces"; Medical Engineering and Physics; bearing a date of 2001; pp. 9-18; vol. 23; Elsevier Science Ltd.; located at: www.elsevier.com/locate/medengphy.
Loeb, G.E.; Peck, R.A.; Martyniuk, J.; "Toward the Ultimate Metal Microelectrode"; Journal of Neuroscience Methods; bearing a date of 1995; pp. 175-183; vol. 63; Elsevier Science B.V.
Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.
Martel, Sylvain; Mathieu, Jean-Baptiste; Felfoul, Ouajdi; Chanu, Arnaud; Aboussouan, Eric; Tamaz, Samer; Pouponneau, Pierre; "Automatic Navigation of an Untethered Device in the Artery of a Living Animal using a Conventional Clinical Magnetic Resonance Imaging System"; Applied Physics Letters; 2007; pp. 114105-1-114105-3; vol. 90, No. 114105; American Institute of Physics.
Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabilization That Self-Regulates the Temperature"; IEEE Transactions on Biomedical Engineering; bearing dates of Jun. 2002 and 2002; pp. 621-623; vol. 49, No. 6; IEEE.

McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.

Naqvi, Nasir H.; Rudrauf, David; Damasio, Hanna; Bechara, Antoine; "Damage to the Insula Disrupts Addiction to Cigarette Smoking"; Science; bearing a date of Jan. 26, 2007; pp. 531-534; vol. 315, No. 531; located at: www.sciencemag.org; printed on Jan. 25, 2007.

Olsson III, R.H.; Gulari, M.N.; Wise, K.D.; "Poster 114: Silicon Neural Recording Arrays with On-Chip Electronics for In-Vivo Data Acquisition"; Microtechnologies in Medicine and Biology; bearing dates of May 2, 2002-May 4, 2002; pp. 237-240; IEEE.

Oweiss, Karim G.; Anderson, David J.; "A New Technique for Blind Source Separation Using Subband Subspace Analysis in Correlated Multichannel Signal Environments"; bearing a date of 2001; pp. 2813-2816; IEEE.

Peckham, P. Hunter; Knutson, Jayme S.; "Functional Electrical Stimulation for Neuromuscular Applications"; Annual Review Biomedical Engineering; bearing a date of 2005; pp. 327-360; vol. 7; Annual Reviews.

Rattay, F.; "The Basic Mechanism for the Electrical Stimulation of the Nervous System"; Neuroscience; 1999; pp. 335-346; vol. 98. No. 2; Elsevier Science Ltd; printed on Mar. 15, 2007.

Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.

Rattay, Frank; Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.

Riedmüller, J.; Bolz, A.; Rebling, H.; Schaldach, M.; "Improvement of Stimulation and Sensing Performance of Bipolar Pacemaker Leads"; IEEE Eng. Med. Biol. Soc.; 1992; pp. 2364-2365; IEEE.

Robinson, David A.; "The Electrical Properties of Metal Microelectrodes"; Proceedings of the IEEE; bearing a date of Jun. 1968; pp. 1065-1071; vol. 56, No. 6.

Rousche, Patrick J.; Pellinen, David S.; Pivin, David P.; Williams, Justin C.; Vetter, Rio J.; Kipke, Daryl R.; "Flexible Polyimide-Based Intracortical Electrode Arrays with Bioactive Capability"; IEEE Transactions on Biomedical Engineering; bearing a date Mar. 2001; pp. 361-371; vol. 48, No. 3; IEEE.

Rutten, Wim; Mouveroux, Jean-Marie; Buitenweg, Jan; Heida, Ciska; Ruardij, Teun; Marani, Enrico; Lakke, Egbert; "Neuroelectronic Interfacing with Cultured Multielectrode Arrays Toward a Cultured Probe"; Proceedings of the IEEE; bearing a date of Jul. 2001; pp. 1013-1029; vol. 89, No. 7; IEEE.

Schoonhoven, R.; Stegeman, D.F.; "Models and Analysis of Compound Nerve Action Potentials"; Critical Reviews in Biomedical Engineering; bearing a date of 1991; pp. 47-111; vol. 19, No. 1; CRC Press, Inc.

Serruya, Mijail D.; Hatsopoulos, Nicholas G.; Paninski, Liam; Fellows, Matthew R.; Donoghue, John P.; "Brief Communications: Instant Neural Control of a Movement Signal"; Nature; bearing a date of Mar. 14, 2002; pp. 141-142; vol. 416; Macmillan Magazines Ltd; located at: www.nature.com.

Snoek, GJ; Ijzerman, MJ; In 'T Groen, Facg; Stoffers, TS; Zilvold, G; "Use of the NESS Handmaster to Restore Handfunction in Tetraplegia: Clinical Experiences in Ten Patients"; Spinal Cord; bearing a date of 2000; pp. 244-249; vol. 38; International Medical Society of Paraplegia.

Struijk, Johannes Jan; "The Extracellular Potential of a Myelinated Nerve Fiber in an Unbounded Medium and in Nerve Cuff Models"; Biophysical Journal; bearing a date of Jun. 1997; pp. 2457-2469; vol. 72; Biophysical Society.

Taylor, Dawn M.; Helms Tillery, Stephen I.; Schwartz, Andrew B.; "Research Article: Direct Cortical Control of 3D Neuroprosthetic Devices"; Science; bearing a date of Jun. 7, 2002; pp. 1829-1832; vol. 296; located at: www.sciencemag.org.

"Tiny Robot Reduces Need for Surgery"; Pink Tentacle; bearing a date of Feb. 26, 2007; p. 1; located at: http://www.pinktentacle.com/2007/02/tiny-robot-reduces-need-for-surgery/; printed on Mar. 8, 2007.

Twardoch, U.M.; "Integrity of Ultramicro-Stimulation Electrodes Determined from Electrochemical Measurements"; Journal of Applied Electrochemistry; bearing a date of 1994; pp. 835-857; vol. 24; Chapman & Hall.

Warland, David K.; Reinagel, Pamela; Meister, Markus; "Decoding Visual Information from a Population of Retinal Ganglion Cells"; bearing a date of 1997; pp. 2336-2350; The American Physiological Society.

Weis, Rolf; Müller, Bernt; Fromherz, Peter; "Neuron Adhesion on a Silicon Chip Probed by an Array of Field-Effect Transitors"; Physical Review Letters; bearing a date of Jan. 8, 1996; pp. 327-330; vol. 76, No. 2; The American Physical Society.

Wessberg, Johan; Stambaugh, Christopher R.; Kralik, Jerald D.; Beck, Pamela D.; Laubach, Mark; Chapin, John K.; Kim, Jung; Biggs, S. James; Srinivasan, Mandayam A.; Nicolelis, Miguel A.L.; "Letters to Nature: Real-Time Prediction of Hand Trajectory by Ensembles of Cortical Neurons in Primates"; Nature; bearing a date of Nov. 16, 2000; pp. 361-365; vol. 408; Macmillan Magazines Ltd; located at: www.nature.com.

White, Dave; "Mini Robot Explores, Gives you Medicine from Within"; Mobile Magazine; bearing a date of Feb. 27, 2007; p. 1; located at: http://www.mobilemag.com/content/100/313/C11869/; printed on Mar. 8, 2007.

U.S. Appl. No. 11/726,031, Ferren et al.
U.S. Appl. No. 11/726,025, Ferren et al.
U.S. Appl. No. 11/725,982, Ferren et al.
U.S. Appl. No. 11/651,946, Ferren et al.
U.S. Appl. No. 11/645,358, Ferren et al.
U.S. Appl. No. 11/645,357, Ferren et al.

UK Examination Report Under Section 18(3); App. No. GB0821524.6; bearing a date of May 6, 2010 (received by our Agent on May 7, 2010); pp. 1-3.

Japanese Office Action; Japanese App. No. 2007-533572; Sep. 22, 2010 (received by our Agent on Sep. 28, 2010); pp. 1-4; (no English translation currently available).

UK Intellectual Property Office Examination Report Under Section 18(3); App. No. GB0821519.6; Oct. 19, 2010 (received by our Agent on Oct. 19, 2010); 1 page.

UK Intellectual Property Office Combined Search and Examination Report Under Sections 17 & 18(3); App. No. GB1016383.0 ; Nov. 1, 2010; pp. 1-4.

U.S. Appl. No. 11/403,230, Ferren et al.
U.S. Appl. No. 11/417,898, Hillis et al.
U.S. Appl. No. 10/949,186, Hillis et al.
U.S. Appl. No. 12/075,480, Hillis et al.
U.S. Appl. No. 10/827,572, Wood, Jr., Lowell L.
U.S. Appl. No. 10/827,576, Wood, Jr., Lowell L.
U.S. Appl. No. 10/827,578, Wood, Jr., Lowell L.
U.S. Appl. No. 10/827,390, Wood, Jr., Lowell L.
U.S. Appl. No. 11/891,333, Wood, Jr., Lowell L.
U.S. Appl. No. 11/891,355, Wood, Jr., Lowell L.
U.S. Appl. No. 11/891,334, Wood, Jr., Lowell L.
U.S. Appl. No. 11/891,356, Wood, Jr., Lowell L.
U.S. Appl. No. 11/891,573, Wood, Jr., Lowell L.
U.S. Appl. No. 11/891,371, Wood, Jr., Lowell L.

"001_08 Comparison of Capsule Cameras: M2A (Given Imaging) vs. NORIKA3 (RF System lab)" RF System lab; bearing dates of 2001-2004; pp. 1-2; located at http://www.rfnorika.com/eng/system/sys_008.html; printed on May 4, 2006.

"Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html.

"Agile new plastics change shape with heat"; MIT Tech Talk; Nov. 22, 2006; p. 5 (1 page).

Ananthaswamy, Anil; "First robot moved by muscle power"; bearing a date of Feb. 27, 2004; pp. 1-3; New Scientist; located at http://www.newscientist.com/article.ns?id=dn4714; printed on Sep. 12, 2006.

Asari, Vijayan K.; Kumar, Sanjiv; Kassim, Irwan M.; "A Fully Autonomous Microrobotic Endoscopy System"; Journal of Intelligent and Robotic Systems; bearing a date of 2000; pp. 325-341; vol. 28; Kluwer Academic Publishers.

Behkam, Bahareh; Sitti, Metin; "Towards Hybrid Swimming Microrobots: Bacteria Assisted Propulsion of Polystyrene Beads"; Proceedings of the 28th IEEE EMBS Annual International Conference; bearing dates of Aug. 30, 2006-Sep. 3, 2006 and 2006; pp. 2421-2424; IEEE.

Berlinger, Norman T.; "Robotic Surgery—Squeezing into Tight Places"; New England Journal of Medicine; bearing dates of May 17, 2006, May 18, 2006, and 2006; pp. 2099-2101; Massachusetts Medical Society; located at www.nejm.org.

Costamagna; Guido M.D.; "PillCam™ SB Capsule Endoscopy"; Given Imaging.com; bearing dates of 2001-2006; pp. 1-4; located at http://www.givenimaging.com/Cultures/en-US/Given/English/Products/CapsuleEndoscopy/; printed on May 4, 2006.

Dario, P.; Carrozza, M.C.; Lencioni, L.; Magnani, B.; D'Attanasio, S.; "A Micro Robotic System for Colonoscopy"; Proceedings of the 1997 IEEE International Conference on Robotics and Automation; bearing dates of Apr. 1997 and 1997; pp. 1567-1572; IEEE.

Dongxiang, Chi; Guozheng, Yan; "An earthworm based miniature robot for intestinal inspection"; Proceedings of SPIE; bearing dates of Nov. 7, 2001-Nov. 9, 2001; pp. 396-400; vol. 4601; SPIE.

Freitas Jr., Robert A.; "8.2.1.2 Arteriocenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine vol. I: Basic Capabilities"; bearing a date of 1999; pp. 211-214, pp. 316-318; Landes Bioscience; Georgetown, Texas, USA.

Høeg, H.D.; Slatkin, A.B.; Burdick, J.W.; Grundfest, Dr. Warren S.; "Biomechanical Modeling of the Small Intestine as Required for the Design and Operation of a Robotic Endoscope"; Proceedings ICRA '00 IEEE International Conference on Robotics and Automation; Apr. 24, 2000-Apr. 28, 2000; pp. 1-8; vol. 2.

Ikeuchi, K.; Yoshinaka, K.; Hashimoto, S.; Tomita, N.; "Locomotion of Medical Micro Robot with Spiral Ribs Using Mucus"; Seventh International Symposium on Micro Machine and Human Science; bearing a date of 1996; pp. 217-222; IEEE.

Kassim, Irwan; Phee, Louis; NG, Wan S.; Gong, Feng; Dario, Paolo; Mosse, Charles A.; "Locomotion Techniques for Robotic Colonoscopy"; IEEE Engineering in Medicine and Biology Magazine; bearing dates of May/Jun. 2006 and 2006; pp. 49-56; IEEE.

Krueger, Curtis; "New light on blood testing"; Oct. 20, 2006; pp. 1-2; St. Petersburg Times; printed on Oct. 24, 2006; located at http://www.sptimes.com/2006/10/20news_pf/Tampabay/New_light_on_blood_te.shtml.

Lu, Zhao; Martel, Sylvain; "Preliminary Investigation of Bio-carriers Using Magnetotactic Bacteria"; Proceedings of the 28th IEEE EMBS Annual International Conference; bearing dates of Aug. 30, 2006-Sep. 3, 2006 and 2006; pp. 3415-3418; IEEE.

Mangan, Elizabeth V.; Kingsley, Dan A.; Quinn, Roger D.; Chiel, Hillel J.; "Development of a Peristaltic Endoscope"; IEEE International Conference on Robotics & Automation 2002; pp. 1-6; located at http://biorobots.cwru.edu/publications/ICRA02_Mangan_Endoscope.pdf.

Martel, Sylvain; "Fundamentals of high-speed piezo-actuated three-legged motion for miniature robots designed for nanometer-scale operations"; pp. 1-8.

Martel, Sylvain; "Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28th IEEE EMBS Annual International Conference; bearing dates of Aug. 30, 2006-Sep. 3, 2006 and 2006; pp. 3399-3402; IEEE.

Mathieu, J-B.; Martel, S.; Yahia, L'H.; Soulez, G.; Beaudoin, G.; "MRI Systems as a Mean of Propulsion for a Microdevice in Blood Vessels"; bearing a date of 2003; pp. 3419-3422; IEEE.

Meier, P.; Oberthür, S.; Lang, M.; "Development of a compliant device for minimally invasive surgery"; Proceedings of the 28th IEEE EMBS Annual International Conference; bearing dates of Aug. 30, 2006-Sep. 3, 2006 and 2006; pp. 331-334; IEEE.

"MEMS at the cutting edge®, Patent Pending"; Verimetra; pp. 1-2; located at http://www.verimetra.com/flow.htm; printed on May 4, 2006.

Menciassi, A.; Park, Jong H.; Lee, S.; Gorini, S.; Dario, P.; Park, Jong-Oh; "Robotic Solutions and Mechanisms for a Semi-Autonomous Endoscope"; Proceedings of the 2002 IEEE/RSJ International Conference on Intelligent Robots and Systems; bearing a date of 2002; pp. 1379-1384; IEEE.

Mosse, Charles; Mills, Tim; Appleyard, Mark; Swain, Paul; "Electrostimulation to move endoscopes in the small bowel"; Proceedings of SPIE; bearing a date of 2001; pp. 24-28; vol. 4158.

Nyitrai, Zsolt; Illyefalvi-Vitéz, Zsolt; Pinkola, János; "Preparing Stents with Masking & Etching Technology"; 26th International Spring Seminar on Electronics Technology; bearing dates of May 8, 2003-May 11, 2003 and 2003; pp. 321-324; IEEE.

Patronik, N.A.; Ota, T.; Zenati, M.A.; Riviere, C.N.; "Improved Traction for a Mobile Robot Traveling on the Heart"; Proceedings of the 28th IEEE EMBS Annual International Conference; bearing dates of Aug. 30, 2006-Sep. 3, 2006 and 2006; pp. 339-342; IEEE.

"Remote-Control Electrostimulation Capsule"; Popular Science; bearing dates of 2002 and 2003; pp. 1-2; located at http://www.popsci.com/popsci/brown/2003/article/0,18881,537028,00.html; printed on May 4, 2006.

Rice, Mike; "Implantable Neurostimulation Device Market Poised for Explosive Growth"; Future Fab International; Jan. 7, 2006; pp. 1-4; printed on Oct. 6, 2006; located at http://www.future-fab.com/documents.asp?d_ID=3725.

Rice, Mike; "New Products, Emphasis on Miniaturization Driving Medical Device Innovation"; bearing a date Aug. 23, 2006; pp. 1-3; Advantage Business Media; located at http://www.mdtmag.com/scripts/ShowPR.asp?PUBCODE=046&ACCT=0006109&ISSUE=0603&RELTYPE=PR&PROCODE=0790&PRODLETT=A; printed on Aug. 23, 2006.

Saltzman, John R.; "Endoscopic Advances—A View Toward the Future"; bearing dates of May 4, 2006, May 17, 2005, and 2005; pp. 1-4; Medscape; located at http://www.medscape.com/viewarticle/505100; printed on May 4, 2006.

Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.

"Trying to control pain can be a double-edged sword, say scientists"; PhysOrg.com; printed on Nov. 2, 2006; pp. 1-2; located at http://www.physorg.com/printnews.php?newsid=81599312.

Tummala, R. Lal; Mukherjee, R.; Aslam, D.; Xi, Ning; Mahadevan, S.; Weng, J.; "Reconfigurable Adaptable Micro-robot"; IEEE; bearing a date of 1999; pp. 687-691.

"Zyvex NanoEffector Microgrippers"; Nanotechnology at Zyvex; printed on Dec. 7, 2006; pp. 1-2; located at http://www.zyvex.com/Products/Grippers_Features.html.

"Zyvex NanoEffector Microgrippers"; Zyvex.com; bearing a date of 2006; pp. 1-2; Zyvex Corporation.

UK Intellectual Property Office Examination Report Under Section 18(3); App. No. GB0821530.3; Aug. 27, 2010 (received by our Agent on Sep. 3, 2010); pp. 1-6.

Arkin, Ronald C.; "Towards the Unification of Navigational Planning and Reactive Control"; Working Notes of the AAAI Spring Symposium on Robot Navigation; bearing dates of Mar. 20-28, 1989; pp. 1-6.

Arleo et al.; "Spatial Cognition and Neuro-Mimetic Navigation: A Model of Hippocampal Place Cell Activity"; bearing a date of Oct. 28, 1999; pp. 1-13.

Balakrishnan et al.; "Spatial Learning and Localization in Rodents: A Computational Model of the Hippocampus and its Implications for Mobile Robots"; Adaptive Behavior; bearing a date of 1999; pp. 173-216 plus cover page; vol. 7, No. 2; SAGE Publications.

Bellin et al.; "Polymeric triple-shape materials"; PNAS; bearing dates of Nov. 18, 2006 and 2006; pp. 18043-18047; vol. 103, No. 48; The National Academy of Sciences of the USA; located at www.pnas.org/cgi/doi/10.1073/pnas.0608586103.

Berman et al.; "Decentralized Autonomous AGV System for Material Handling"; iFirst; bearing a date of Oct. 2002; pp. 3995-4006 (Only the Abstract is being provided); vol. 40, No. 15; located at: http://www.informaworld.com/smpp/content~content=a713846479~db=ai; printed on Apr. 24, 2007.

Bianco et al.; "Carbon Nanotube-based Vectors for Delivering Immunotherapeutics and Drugs"; Nanotechnologies for the Live Sciences: Nanomaterials for Medical Diagnosis and Therapy; bearing a date of 2007; Chapter 3; pp. 85-142.; vol. 10; WILEY-VCH Verlag GmbH & Co. KGaA; Weinheim.

Breslin et al.; "Autofluorescence and Diffuse Reflectance Properties Malignant and Benign Breast Tissues"; Annals of Surgical Oncology; bearing dates of 2003 and 2004; pp. 65-70; vol. 11, No. 1; Lippincott Williams & Wilkin.

Bright et al.; "Automated Pipe Inspection Robot"; Industrial Robot: An International Journal; bearing a date of Aug. 1997; pp. 285-289 (Only the Abstract is being provided); vol. 24, No. 4; located at: http://www.emeraldinsight.com/10.1108/01439919710176372; printed on Apr. 23, 2007.

Brinn, David; "A incredible journey from an Israeli robotics team"; ISRAEL21c: A Focus Beyond; bearing a date of Nov. 12, 2006; pp. 1-3; ISRAEL21c.org.

Brown et al.; "Performance Test Results of an Integrated GPS/MEMS Inertial Navigation Package"; Proceedings of ION GNSS 2004, bearing a date of Sep. 2004; pp. 1-8.

Budgett et al.; "Novel technology for the provision of power to implantable physiological devices"; Journal of Applied Physiology; bearing dates of Jan. 27, 2006, Jan. 5, 2007, and 2007; pp. 1658-1663; vol. 102; The American Physiological Society.

Bullitt et al.; "Analysis of Time-Varying Images Using 3D Vascular Models"; Proceedings 30th Applied Imagery Pattern Recognition Workshop; bearing a date of Apr. 2001; pp. 9-14; IEEE Computer Society; Piscataway, NJ.

Burke et al.; "Towards a single-chip, implantable RFID system: is a single-cell radio possible?"; Biomed Microdevices; bearing a date of 2009; pp. 1-8; Springer.

Cady et al.; "Optimized linkage and quenching strategies for quantum dot molecular beacons"; Molecular and Cellular Probes; bearing dates of Jul. 5, 2006, Sep. 7, 2006, Sep. 17, 2006, 2006, and 2007; pp. 116-124; vol. 21; Elsevier Ltd.

Cavalcanti et al.; "Autonomous Multi-Robot Sensor-Based Cooperation for Nanomedicine"; Nanotechnology Special Edition; bearing a date of Aug. 2002; pp. 1-4; International Journal of Nonlinear Science and Numerical Stimulation.

Chen et al.; "Review on the Achievements in Simultaneous Localization and Map Building for Mobile Robot" CSA Illumina; bearing a date of Jun. 2005; pp. 455-460 (Only the Abstract is being provided); vol. 22, No. 3; ProQuest-CSA LLC; located at: http://mdl.csa.com/partners/viewrecord.php?requester=gs&collection=TRD&recid=A056354818AH&recid=2005134422784EA&q=Review+on+the+Achievements+in+Simultaneous+Localization+and+Map+Building+for+Mobile+Robot&uid=790366044&setcookie=yes.

Chiyo et al.; "Effective detection of bronchial preinvasive lesions by a new autofluorescence imaging bronchovideoscope system"; Lung Cancer; bearing dates of May 12, 2004, Nov. 17, 2004, Nov. 23, 2004, 2004, and 2005; pp. 307-313; vol. 48; Elsevier Ireland Ltd.

Chung et al.; "Advanced Optical Imaging Requiring No Contrast Agents—A New Armamentarium for Medicine and Surgery"; Current Surgery; bearing dates of May/Jun. 2005 and 2005; pp. 365-370; vol. 62, No. 3; Elsevier Inc.

Dacosta et al.; "Autofluorescence characterisation of isolated whole crypts and primary cultured human epithelial cells from normal, hyperplastic, and adenomatous colonic mucosa"; Journal of Clinical Pathology; bearing dates of 2004 and 2005; pp. 766-774; vol. 58.

Degani et al.; "Minimalistic, Dynamic, Tube Climbing Robot"; 2010 IEEE International Conference on Robotics and Automation; bearing dates of May 3-8, 2010 and 2010; pp. 1100-1101; IEEE.

Desouza et al.; "Vision for Mobile Robot Navigation: A Survey"; IEEE Transactions on Pattern Analysis and Machine Intelligence; bearing a date of Feb. 2002; pp. 237-267 (Only the Abstract is being provided); vol. 24, No. 2; located at: http://csdl2.computer.org/persagen/DLAbsToc.jsp?resoureePath=/dl/trans/tp/&toc=comp/trans/tp/2002/02/i2toc.xml&DOI=10.1109/34.982903; printed on Apr. 23, 2007.

Diard et al.; "A theoretical comparison of probabilistic and biomimetic models of mobile robot navigation"; Proceedings of the 2004 IEEE International Conference on Robotics & Automation; bearing dates of Apr. 2004 and 2004; pp. 933-938; IEEE.

Dweik et al.; "Exhaled breath analysis: the new frontier in medical testing"; Journal of Breath Research; bearing a date of 2008; pp. 1-3; vol. 2; IOP Publishing Ltd; UK.

Edwards, Lin; "Spider pill to seek out disease"; PhysOrg.com; bearing dates of Oct. 16, 2009 and 2009; p. 1.

Eker et al.; "Clinical spectral characterisation of colonic mucosal lesions using autofluorescence and δ aminolevulinic acid sensitization"; Gut; bearing dates of 1998 and 1999; pp. 511-518; vol. 44.

Eulenstein et al.; "Ultrasound-Based Navigation System Incorporating Preoperative Planning for Liver Surgery"; International Congress Series CARS 2004—Computer Assisted Radiology and Surgery, Proceedings of the 18$^{th}$ International Congress and Exhibition; bearing a date of 2004; pp. 758-763; vol. 1268.

Filliat et al.; "Map Based Navigation in Mobile Robots: I. A Review of Localization Strategies"; Science Direct-Cognitive Systems Research; bearing dates of Feb. 12, 2003 and Dec. 2003; pp. 1-58; vol. 4, No. 4; Elsevier Science.

Foxlin et al.; "Miniature 6-DOF inertial system for tracking HMDs"; Helmet and Head-Mounted Displays III, AeroSense 98; bearing dates of Apr. 13-14, 1998; pp. 1-15; vol. 3362; SPIE.

Gabrecht et al.; "Detection of early bronchial cancer by autofluorescence: results in patients with H&N cancer"; Diagnostic Optical Spectroscopy in Biomedicine IV, Proc. SPIE-OSA Biomedical Optics; bearing a date of 2007; pp. 1-8; vol. 6628; SPIE-OSA.

Gao et al., "A Micro Sensing Probe for Detecting Individual Biological Cells"; Proceedings of the 25$^{th}$ Annual International Conference of the IEEE EMBS; bearing dates of Sep. 17-21, 2003 and 2003; pp. 3348-3351; IEEE.

Gillenwater et al.; "Noninvasive Diagnosis of Oral Neoplasia Based on Fluorescence Spectroscopy and Native Tissue Autofluorescence"; Archives of Otolaryngology—Head & Neck Surgery; bearing a date of Nov. 1998 and 1998; pp. 1251-1258; vol. 124.

Grifantini, Kristina; "Voyage of the Bacteria Bots"; Technology Review; bearing a date of Oct. 31, 2008; pp. 1-4; Technology Review.

Groothuis et al.; "The entry of antiviral and antiretroviral drugs into the central nervous system"; Journal of NeuroVirology; bearing a date of 1997; pp. 387-400; vol. 3; Journal of NeuroVirology, Inc.

"Guessing Robots Predict Their Environments, Navigate Better"; PhysOrg.com; printed on Sep. 16, 2008; pp. 1-2; original story found at www.phyorg.com/news100887209.html.

Gur, Amir; "The Nanobots are Coming"; TFOT; bearing a date of Jul. 9, 2007; pp. 1-2; The Future of Things.

Hattori, Kevin; "Robot Can Crawl Through Human Body"; American Technion Society; bearing a date of Jul. 7, 2009; pp. 1-2; American Technion Society; located at http://www.ats.org/site/News2?page=NewsArticle&id=6063 &news_iv_ctrl=1161&printer_friendly=1.

Herth et al.; "Successful Bronchoscopic Placement of Tracheobronchial Stents Without Fluoroscopy*"; Chest; bearing a date of Jun. 2001; pp. 1910-1912; vol. 119, No. 6; American College of Chest Physicians.

Hertzberg et al.; "Landmark-Based Autonomous Navigation in Sewerage Pipes"; Proceedings of EUROBOT; bearing a date of 1996; pp. 68-73; IEEE.

Hirsch et al.; "A new device with PZT ultrasonic transducers in MEMS technology"; Journal of Physics: Conference Series 34, International MEMS Conference 2006; bearing a date of 2006; pp. 475-480; IOP Publishing Ltd.

Hollings et al.; "Diagnostic imaging of lung cancer"; European Respiratory Journal; bearing a date of 2002, pp. 722-742; vol. 19; ERS Journals Ltd.

Hornyak, Tim; "RFID Powder"; Scientific American Magazine; bearing dates of Feb. 2008 and 2008; pp. 68-71; Scientific American, Inc.

Hosseini-Khayat, Saied; "A Lightweight Security Protocol for Ultra-low Power ASIC Implementation for Wireless Implantable Medical Devices"; 2011 Symposium on Medical Information and Communication Technology (ISMICT); bearing dates of 2011 and Mar. 27-30, 2011; pp. 6-9; IEEE.

Howell et al.; "Practical Mobile Robot Self-Localization"; Proceedings of the IEEE International Conference on Robotics and Automation, 2000; bearing dates of Apr. 24-28, 2000; pp. 3485-3492; vol. 4.

Jaiswal et al.; "Long-term multiple color imaging of live cells using quantum dot bioconjugates"; Nature Biotechnology; bearing dates of Jan. 2003 and 2003; pp. 47-51; vol. 21; Nature Publishing Group.

Jovanov et al.; "A wireless body area network of intelligent motion sensors for computer assisted physical rehabilitation"; Journal of NeuroEngineering and Rehabilitation; bearing dates of Mar. 1, 2005, Jan. 28, 2005, Mar. 1, 2005, and 2005; pp. 1-10; vol. 2, No. 6; BioMed Central Ltd.

Karino et al.; "Flow Patterns in Vessels of Simple and Complex Geometries""; Annals of the New York Academy of Sciences; bearing a date of 1987; pp. 422-441; vol. 516.

Kawaguchi et al.; "Internal Pipe Inspection Robot"; IEEE Xplore; bearing dates of May 21, 1995-May 27, 1995 and 2005; pp. 857-862 (Only the Abstract is being provided); vol. 1; IEEE; located at: http://ieeexplore.ieee.org/xpls/abs_all.jsp?rnumber=525390; printed on Apr. 23, 2007.

Kharitonov et al.; "Exhaled Markers of Pulmonary Disease"; American Journal of Respiratory and Critical Care Medicine; bearing dates of Sep. 5, 2000, Jan. 24, 2001, and 2001; pp. 1693-1722; vol. 163.

Kim et al.; "Inchworm-Like Microbot for Capsule Endoscope"; Proceedings of the 2004 IEEE International Conference on Robotics and Biomimetics; bearing dates of Aug. 22-26, 2004 and 2004; pp. 458-463; IEEE.

Kim et al.; "Ultrasensitive carbon nanotube-based biosensors using antibody-binding fragments"; Analytical Biochemistry; bearing a date of 2008; pp. 193-198; vol. 381; Elsevier Inc.

Kirchner et al.; "A Prototype Study of an Autonomous Robot Platform for Sewerage System Maintenance"; Autonomous Robots; bearing a date of 1997; pp. 319-331; vol. 4; Kluwer Academic Publishers.

Kitaoka et al.; "A three-dimensional model of the human airway tree"; Journal of Applied Physiology; bearing a date of 1999; pp. 2207-2217; vol. 87; The American Physiological Society.

Kitching, John; "Time for a Better Receiver: Chip-Scale Atomic Frequency References"; GPS World; bearing a date of Nov. 2007; pp. 52-57.

Knappe, Svenja; "Emerging Topics: MEMS Atomic Clocks"; Comprehensive Microsystems; bearing a date of 2007; pp. 571-612; vol. 3; Elsevier B.V.; Netherlands.

Koenig et al.; "Laser-Induced Autofluorescence for Medical Diagnosis"; Journal of Fluorescence; bearing a date of 1994, pp. 17-40; vol. 4, No. 1; Plenum Publishing Corporation.

Kuipers et al.; "A Robot Exploration and Mapping Strategy Based on a Semantic Hierarchy of Spatial Representations"; Robotics and Autonomous Systems; bearing a date of 1981; pp. 47-63; vol. 8; Elsevier Science Publishers B.V.

Kuntze et al.; "Experiences With the Development of a Robot for Smart Multisensoricpipe Inspection"; IEEE Xplore; bearing dates of May 16, 1998-May 20, 1998 and 2005; pp. 1773-1778 (Only the Abstract is being provided); vol. 2; IEEE; located at: http://ieeexplore.ieee.org/xpls/abs_all.jsp?rnumber=677423; printed on Apr. 23, 2007.

Latombe, Jean-Claude; "Chapter 1: Introduction and Overview"; Robot Motion Planning; bearing a date of 1991; 11 pages total, pp. 12-20; Kluwer Academic Publishers.

Laumond et al.; "Robot Motion Planning and Control"; bearing a date of 1998; pp. 1-343 plus cover page, foreword and table of contents (353 total pages); Springer.

Leong et al.; "Tetherless thermobiochemically actuated microgrippers"; PNAS; bearing dates of Jan. 20, 2009 and 2009; pp. 703-708; vol. 106, No. 3; The National Academy of Sciences of the USA; located at www.pnas.org_cgi_doi_10.1073_pnas.0807698106.

Luckevich, Mark, "MEMS microvalves: the new valve world"; Valve-World; bearing a date of May 2007; pp. 79-83.

Lynch et al.; "Design of Piezoresistive MEMS-Based Accelerometer for Integration with Wireless Sensing Unit for Structural Monitoring"; Journal of Aerospace Engineering; bearing a date of Jul. 2003; pp. 108-114; vol. 3; ASCE.

Machado et al., "Detection of Lung Cancer by Sensor Array Analyses of Exhaled Breath"; American Journal of Respiratory and Critical Care Medicine; bearing a date of 2005; pp. 1286-1291; vol. 171.

Marcu et al.; "In vivo detection of macrophages in a rabbit atherosclerotic model by time-resolved laser-induced fluorescence spectroscopy"; Atherosclerosis; bearing a date of 2005, pp. 295-303; vol. 181; Elsevier Ireland Ltd.

Martel, Sylvain; "Fundamental Principles and Issues of High-speed Piezoactuated Three-legged Motion for Miniature Robots Designed for Nanometer-scale Operations"; The International Journal of Robotics Research; bearing dates of Jul. 2005 and 2005; pp. 575-588; vol. 24, No. 7; Sage Publications.

Mataric, Maja J.; "Integration of Representation into Goal-Driven Behavior-Based Robots"; IEEE Transactions on Robotics and Automation; bearing dates of Jun. 1992 and 1992; pp. 304-312; vol. 8, No. 3; IEEE.

Mattley et al.; "Blood Characterization using uv/vis Spectroscopy"; Advances in Fluorescence Sensing Technology II (Proceedings Volume); bearing a date of 1995; pp. 462-470; vol. 2388; SPIE.

Mehmood et al.; "Autonomous Navigation of Mobile Agents Using RFID-Enabled Space Partitions"; ACMGIS '08; bearing dates of Nov. 5-7, 2008 and 2008; pp. 1-10; ACM.

Menciassi et al.; "Towards Active Capsular Endoscopy: Preliminary Results on a Legged Platform"; Proceedings of the 28th IEEE EMBS Annual International Conference; bearing dates Aug. 30, 2006-Sep. 3, 2006 and 2006; pp. 2215-2218; IEEE.

Meyer et al.; "Map-Based Navigation in Mobile Robots: II. A Review of Map-Learning and Path-Learning Strategies"; Science Direct-Cognitive Systems Research; bearing dates of Feb. 12, 2003 and Dec. 4, 2003; pp. 1-51; vol. 4, No. 4; Elsevier Science.

Mohan et al., "Bokode: Imperceptible Visual tags for Camera Based Interaction from a Distance"; ACM Transactions on Graphics (Proceedings of SIGGRAPH 2009); bearing dates of Aug. 3-7, 2009; pp. 1-8.

Mok et al.; "Recent Progress in Nucleic Acid Aptamer-Based Biosensors and Bioassays"; Sensors; bearing a date of 2008; pp. 7050-7084; vol. 8.

Morrison et al., "Clinical Applications of Micro- and Nanoscale Biosensors"; Biomedical Nanostructures; bearing a date of 2008; Chapter 17; pp. 433-454; John Wiley & Sons, Inc.

Motomiya et al.; "Flow Patterns in the Human Carotid Artery Bifurcation"; Stroke; bearing dates of Jan.-Feb. 1984; pp. 50-56; vol. 15, No. 1.

Nehmzow et al.; "Robot Navigation in the Real World: Experiments with Manchester's *FortyTwo* in Unmodified, Large Environments"; Robotics and Autonomous Systems; bearing a date of 2000; pp. 223-242; vol. 33; Elsevier Science B.V.

Nguyen, Clark T.-C.; "MEMS Technology for Timing and Frequency Control"; IEEE Transactions on Ultrasonics, Ferroelectrics, and Frequency Controls; bearing dates of Feb. 2007 and 2007; pp. 251-270; vol. 54, No. 2; IEEE.

Nordstrom et al.; "Identification of Cervical Intraepithelial Neoplasia (CIN) Using UV-Excited Fluorescence and Diffuse-Reflectance Tissue Spectroscopy"; Lasers in Surgery and Medicine; bearing a date of 2001; pp. 118-127; vol. 29; Wiley-Liss, Inc.

Nowinski et al.; "Three-dimensional Atlas of the Brain Anatomy and Vasculature[1]"; RadioGraphics; bearing dates of Jan.-Feb. 2005 and 2005; pp. 263-271; vol. 25, No. 1; RSNA.

Pan et al.; "A magnetically driven PDMS micropump with ball checkvalves"; Journal of Micromechanics and Microengineering; bearing a date of 2005, pp. 1021-1026; vol. 15; IOP Publishing Ltd.

Pavlidis, N.; "The diagnostic and therapeutic management of leptomeningeal carcinomatosis"; Annals of Oncology; bearing a date of 2004; pp. iv285-iv291; vol. 15 (Supp. 4); European Society for Medical Oncology.

Peng et al.; "Ultraviolet light-emitting diodes operating in the 340 nm wavelength range and application to time-resolved fluorescence spectroscopy"; Applied Physics Letters; bearing dates of Aug. 23, 2004 and 2004; pp. 1436-1438; vol. 85, No. 8; American Institute of Physics.

Pfister et al.; "Weighted Line Fitting Algorithms for Mobile Robot Map Building and Efficient Data Representation"; Proceedings of the 2003 IEEE International Conference on Robotics and Automation; bearing a date of Sep. 14-19, 2003; pp. 1-8.

"Philips develops "intelligent pill""; Reuters; bearing a date of Nov. 11, 2008; p. 1; Thomson Reuters.

"Philips' intelligent pill targets drug development and treatment for digestive tract diseases"; PhysOrg.com; bearing a date of Nov. 11, 2008; pp. 1-3; located at http://www.physorg.com/news145640874.html.

Phillips et al.; "Detection of Lung Cancer With Volatile Markers in the Breath*"; Chest; bearing dates of Jun. 2003 and 2003; pp. 2115-2123; vol. 123, No. 6; American College of Chest Physicians.

Pisupati et al.; "A Central Axis Algorithm for 3D Bronchial Tree Structures"; Proceedings of the International Symposium on Computer Vision; bearing a date of 1995; pp. 259-264; IEEE.

Psathakis et al.; "8-Isoprostane, a Marker of Oxidative Stress, Is Increased in the Expired Breath Condensate of Patients With Pulmonary Sarcoidosis*"; Chest; bearing dates of Mar. 2004 and 2004, pp. 1005-1011; vol. 125, No. 3; American College of Chest Physicians.

Quaglia et al.; "An endoscopic capsule robot: a meso-scale engineering case study"; Journal of Micromechanics and Microengineering; bearing a date of 2009; pp. 1-11; vol. 19; IOP Publishing Ltd.

Quirini et al.; "Design of a Pill-Sized 12-legged Endoscopic Capsule Robot"; 2007 IEEE International Conference on Robotics and Automation; bearing dates of Apr. 10-14, 2007 and 2007; pp. 1856-1862; IEEE.

Raman et al.; "In Vivo Atherosclerotic Plaque Characterization Using Magnetic Susceptibility Distinguishes Symptom-Producing Plaques"; JACC: Cardiovascular Imaging; bearing dates of Jan. 2008 and 2008; pp. 49-57; vol. 1, No. 1; Elsevier.

Rasmussen et al.; "Proximity-based Access Control for Implantable Medical Devices"; CCS '09, Proceedings of the 16th ACM Conference on Computer and Communications Security; bearing dates of Nov. 9-13, 2009 and 2009; pp. 1-10.

"Remote-controlled capsule endoscope safely examines the stomach"; PhysOrg.com; bearing a date of Jan. 18, 2011; pp. 1-2; located at http://www.physorg.com/news-2011-01-remote-controlled-capsule-endoscope-safely-stomach.html.

"Researchers Create Tiny, Self-Propelled Devices"; PhysOrg.com; printed on Feb. 12, 2007; pp. 1-3; located at: http://www.physorg.com/printnews.php?newsid—90521279.

Roh et al.; "Strategy for Navigation Inside Pipelines With Differential-Driveinpipe Robot"; IEEE Xplore; 2002 and 2005; pp. 2575-2580 (Only the Abstract is being provided); vol. 3; IEEE; located at: http://ieeexplore.ieee.org/xpls/abs_all.jsp?arnumber=1013619; printed on Apr. 23, 2007.

Roh et al.; "Actively Steerable In-Pipe Inspection Robots for Underground Urban Gas Pipelines"; IEEE Xplore; bearing dates of 2001 and 2005; pp. 761-766 (Only the Abstract is being provided); vol. 1; IEEE; located at: http://ieeexplore.ieee.org/xpls/abs_all.jsp?arnumber=932642; printed on Apr. 23, 2007.

Rolfe, Brigitte; "Toward Nanometer-Scale Sensing Systems: Natural and Artificial Noses as Models for Ultra-Small, Ultra-Dense Sensing Systems"; Advances in Computers; bearing dates of Nov. 2004, 2004, and 2007; pp. 11-46; vol. 71; Elsevier, B.V.

Schertler et al.; "Effects of ECG Gating and Postprocessing Techniques on 3D MDCT of the Bronchial Tree"; AJR; bearing a date of Jul. 2004; pp. 83-89; vol. 183; American Roentgen Ray Society.

Schnakenberg et al.; "Intravascular pressure monitoring system"; Sensors and Actuators A: Physical; bearing a date of 2004; pp. 61-67; vol. 110; Elsevier B.V.

Schwartz, John; "In the Lab: Robots That Slink and Squirm"; The New York Times: Science; bearing a date of Mar. 27, 2007; pp. 1-4; The New York Times Company; located at: http://www.nytimes.com/2007/03/27/science/27robo.html?ex=1332648000&en=d4541141c174b454&ei=5124&partner=digg&exprod=digg; printed on Mar. 27, 2007.

"Spider pill to seek out diseases"; PhysOrg.com; bearing a date of Oct. 16, 2009 and 2009; p. 1; located at http://www.physorg.com/news174893082.html.

Sun et al.; "A Miniature RF Communication System for Micro Gastrointestinal Robots"; Journal of Medical Engineering & Technology; bearing a date of 2003; pp. 160-163; vol. 27.

Suzumori et al.; "Micro Inspection Robot for 1-in Pipes"; IEEE/ASME Transactions on Mechatronics; bearing dates of Sep. 1999 and 1999; pp. 286-292; vol. 4, No. 3; IEEE.

Tang et al.; "Cerebral Vascular Tree Matching of 3D-RA Data Based on Tree Edit Distance"; Medical Imaging and Augmented Reality; bearing a date of 2006; pp. 116-123.

The Biomedical Engineering Handbook, Second Edition; bearing a date of 2000; pp. IV-1-43-31; vol. I; CRC Press LLC.

The Biomedical Engineering Handbook, Second Edition; bearing a date of 2000; pp. V-1-51-9; vol. I; CRC Press LLC.

Thrun, Sebastian; "Learning Metric-Topological Maps for Indoor Mobile Robot Navigation"; Artificial Intelligence; bearing a date of 1998; pp. 21-71; vol. 99; Elsevier Science B.V.

Thrun, Sebastian; "Probabilistic Algorithms in Robotics"; AI Magazine; bearing dates of Winter 2000 and 2000; pp. 93-109; vol. 21, No. 4; American Association for Artificial Intelligence.

Thrun, Sebastian; "Robotic Mapping: A Survey"; Exploring Artificial Intelligence in the New Millenium; bearing a date of Feb. 2002; pp. 1-29 (31 total pages); Morgan Kaufmann.

Thrun et al.; "A Real-Time Algorithm for Mobile Robot Mapping With Applications to Multi-Robot and 3D Mapping"; IEEE International Conference on Robotics and Automation; bearing a date of Apr. 2000; pp. 1-8.

Thrun et al.; "Integrating Topological and Metric Maps for Mobile Robot Navigation: A Statistical Approach"; pp. 1-7.

Tomatis et al.; "Simultaneous Localization and Map Building: A Global Topological Model with Local Metric Maps"; Robotics Autonomous Systems; bearing a date of 2003; pp. 1-6; vol. 44.

Tsuruta et al.; "Control Circuit in an In-Pipe Wireless Micro Inspection Robot"; IEEE Xplore; bearing dates of 2000 and 2005; pp. 59-64 (Only the Abstract is being provided); IEEE; located at: http://ieeexplore.ieee.org/xpls/abs_all.jsp?arnumber=903290; printed on Apr. 23, 2007.

Ulrich et al.; "Appearance-Based Place Recognition for Topological Localization"; IEEE International Conference on Robotics and Automation; bearing a date of Apr. 2000; pp. 1023-1029.

Verheye et al.; "Selective Clearance of Macrophages in Atherosclerotic Plaques by Autophagy"; Journal of the American College of Cardiology; bearing dates of Feb. 13, 2007 and 2007; pp. 706-715; vol. 49, No. 6; Elsevier Inc.

Wacharasindhu et al.; "Radioisotope microbattery based on liquid semiconductor"; Applied Physics Letters; bearing dates of Dec. 11, 2008, Jun. 9, 2009, Jul. 6, 2009, Dec. 8, 2009 and 2009; pp. 014103-1-014103-3; vol. 95; American Institute of Physics.

Wakimoto et al.; "A Micro Snake-Like Robot for Small Pipe Inspection"; International Symposium on Micromechatronics and Human Science; bearing a date of 2003; pp. 303-308; IEEE.

Wang et al.; "A MEMS-based Air Flow Sensor with a Free-standing Micro-cantilever Structure"; Sensors; bearing dates of Aug. 27, 2007, Oct. 10, 2007, Oct. 17, 2007, and 2007; pp. 2389-2401; vol. 7; MDPI.

Watson et al.; "Piezoelectric ultrasonic resonant motor with stator diameter less than 250 μm: the Proteus motor"; Journal of Micromechanics and Microengineering; bearing dates of Sep. 25, 2008, Nov. 18, 2008, Jan. 20, 2009, and 2009; pp. 1-5; vol. 19; IOP Publishing Ltd.

Weingandt et al.; "Autofluorescence spectroscopy for the diagnosis of cervical intraepithelial neoplasia"; BJOG: an International Journal of Obstetrics and Gynaecology; bearing dates of Aug. 2002 and 2002; pp. 947-951; vol. 109; RCOG.

Xi et al.; "Self-assembled microdevices driven by muscle"; Nature Materials; bearing dates of Feb. 2005 and 2005; pp. 180-184 (10 pages total); vol. 4; Nature Publishing Group.

Yang et al.; "Power generation with laterally packaged piezoelectric fine wires"; Nature Nanotechnology; bearing dates of Nov. 9, 2008, Jan. 2009, and 2009; pp. 34-39; vol. 4; Macmillan Publishers Limited.

Yang et al.; "Converting Biomechanical Energy into Electricity by a Muscle-Movement-Driven Nanogenerator"; Nano Letters; bearing dates of Dec. 25, 2008, Jan. 31, 2009, and 2009; pp. 1201-1205; vol. 9, No. 3; American Chemical Society.

Yu et al.; "System for the analysis and visualization of large 3D anatomical trees"; Computers in Biology and Medicine; bearing dates of Oct. 6, 2006, May 31, 2007, Jun. 4, 2007, and 2007; pp. 1802-1820; vol. 37; Elsevier Ltd.

Zhao et al.; "Physicist Develops Natural Motor Technique"; PhysOrg.com; bearing dates of Apr. 21, 2007 and 2007; 1 page;

United Press International; located at: http://www.physorg.com/news96357975.html; printed on Apr. 23, 2007.

Zheng et al.; "Design and Fabrication of a Micro Coulter Counter with Thin Film Electronics"; Proceedings of 2006 International Conference on Microtechnologies in Medicine and Biology; bearing dates of May 9-12, 2006 and 2006; pp. 16-19; IEEE.

Zhu et al.; "Flattening Maps for the Visualization of Multibranched Vessels"; IEEE Transactions on Medical Imaging; bearing dates of Feb. 10, 2004, Sep. 27, 2004, Feb. 2005, and 2005; pp. 191-198; vol. 24, No. 2; IEEE.

Zrimec et al.; "3D Modelling and Visualization of the Human Lung"; Proceedings of the 2nd International Symposium on 3D Data Processing, Visualization, and Transmission (3DPVT'04); bearing a date of 2004; pp. 110-115; IEEE.

Zyga, Lisa; "Microswimmer Propels Itself With Near-Zero Friction"; PhysOrg.com; bearing dates of Jun. 4, 2007 and 2007; pp. 1-2; PhyOrg.com; located at: http://www.physorg.com/news100176842.html; printed on Jun. 6, 2007.

UK Intellectual Property Office Examination Report under Section 18(3); App. No. GB0821521.2; Jan. 12, 2011 (received by our agent on Jan. 13, 2011); pp. 1-4.

UK Intellectual Property Office Examination Report Under Section 18(3); App. No. GB0821524.6; Aug. 9, 2010 (received by our Agent on Aug. 10, 2010); pp. 1-2.

UK Intellectual Property Office Examination Report Under Section 18(3); App. No. GB0821519.6; Aug. 9, 2010 (received by our Agent on Aug. 10, 2010); pp. 1-3.

Mosby's Dictionary of Medicine, Nursing & Health Professions; "endoscopy"; 2009; Credo Reference. Web. Jun. 29, 2011; 1 page; Elsevier Health Sciences.

U.S. Appl. No. 13/135,696, filed Jul. 12, 2011, Ferren et al.
U.S. Appl. No. 13/135,694, filed Jul. 12, 2011, Ferren et al.
U.S. Appl. No. 12/928,455, Wood, Jr., Lowell L.
U.S. Appl. No. 12/930,916, Wood, Jr., Lowell.

UK Intellectual Property Office Examination Report Under Section 18(3); App. No. GB0821526.1; bearing a date of Jul. 15, 2010; received by our agent Jul. 16, 2010; pp. 1-2.

U.S. Appl. No. 13/136,680, Ferren et al.
U.S. Appl. No. 13/136,679, Ferren et al.
U.S. Appl. No. 13/136,677, Ferren et al.
U.S. Appl. No. 13/136,676, Ferren et al.
U.S. Appl. No. 13/136,675, Ferren et al.
U.S. Appl. No. 13/136,678, Ferren et al.
U.S. Appl. No. 13/136,674, Ferren et al.

"A Hydrogel-based CO2 sensor"; BIOS—The lab on a chip group; bearing a date of Aug. 29, 2005; pp. 1-2; located at: http://bios.ewi.utwente.nl/research/analysissystemssenors/ahydrogelbased.doc/index.html; printed on Apr. 25, 2006; University of Twente; The Netherlands.

Agarwal, Abhishek K.; Atencia, Javier; Beebe, David J.; Jiang, Hongrui; "Magnetically-driven temperature-controlled microfluidic actuators"; pp. 1-5; located at: http://www.unl.im.dendai.ac.jp/INSS2004/INSS2004_papers/OralPresentations/C2.pdf.

Bezrouk, A.; Hanuš, J.; Záhora, J.; "Temperature Characteristics of Nitinol Spiral Stents"; Scripta Medica (BRNO); bearing dates of Aug. 2005, Oct. 2005; pp. 219-226; vol. 78, No. 4.

Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; Collaborative Investigators for Applied Nanotechnology in Medicine; pp. 1; Chicago, Illinois.

Chen, Ting; Barton, Scott Calabrese, Binyamin, Gary; Gao, Zhiqiang; Zhang, Yongchao, Kim, Hyug-Han; Heller, Adam; "A Miniature Biofuel Cell"; Journal of the American Chemical Society; Aug. 11, 2001; pp. 8630-8631; vol. 123; 2001 American Chemical Society.

Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.

Hanna, Darrin M.; Oakley, Barbara A.; Stryker, Gabrielle A.; "Using a System-on-Chip Implantable Device to Filter Circulating Infected Cells in Blood or Lymph"; IEEE Transactions on Nanobioscience; bearing dates of Jan. 25, 2003, Mar. 2003; pp. 6-13; vol. 2, No. 1; IEEE.

Langer, Robert; Peppas, Nicholas A.; "Advances in Biomaterials, Drug Delivery, and Bionanotechnology"; AIChE Journal—Bioengineering, Food, and Natural Products; Dec. 2003; pp. 2990-3006; vol. 49, No. 12.

Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabililzation That Self-Regulates the Temperature"; IEEE Transactions on Biomedical Engineering; bearing dates of Jun. 2002 and 2002; pp. 621-623; vol. 49, No. 6; IEEE.

Murthy, S. Narasimha; Hiremath, Shobha Rani R.; "Physical and Chemical Permeation Enhancers in Transdermal Delivery of Terbutaline Sulphate"; AAPS PharmSciTech; bearing dates of 2001, Aug. 7, 2000, and Feb. 12, 2001; pp. 1-5; vol. 2 (1) Technical Note 1; located at: http://www.pharmscitech.com/.

Nakayama, Yasuhide; Ji-Youn, Kim; Nishi, Shogo; Ueno, Hikaru; Matsuda, Takehisa; "Development of high-performance stent: gelatinous photogel-coated stent that permits drug delivery and gene transfer"; J Biomed Mater Res; bearing dates of Nov. 13, 2000, Apr. 23, 2001, May 10, 2001 and 2001; pp. 559-566; vol. 57; John Wiley & Sons, Inc.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"New Medical Device Combines Wireless and MEMS Technology"; Georgia Institute of Technology; pp. 1-4; PhysOrg.com; located at: http://www.physorg.com/printnews.php?newsid=10533; printed on Feb. 20, 2006.

Nieuwenhuizen-Berkovits, P.; "lubrelastic medical appliances"; Lubrelastic Medical Appliances; pp. 1-4; located at: http://www.xs4all.nl/~plien070/caeng.html; printed on Feb. 20, 2006.

Schmidt, W.; Behrens, P.; Behrend, D.; Schmitz, K.-P.; Andresen, R.; "Experimental Study of Peripheral, Balloon-expandable Stent Systems"; Progress in Biomedical Research; bearing a date of May 2001; pp. 246-255.

Senel, S.; Hincal, A. A.; "Drug permeation enhancement via buccal route: possibilities and limitations."; J Control Release; bearing a date of May 14, 2001; pp. 1-2; vol. 72 (1-3); located at: http://www.ncbi.nlm.nih.gov/entrez/query.fcgi?cmd=Retrieve&db=PubMed&list_uids=11389992&dopt=Abstract; and at: www.pubmed.gov ; printed on Apr. 28, 2006.

Serruys, Patrick W.; Kutryk, Michael J.B.; Ong, Andrew T.L.; "Coronary-Artery Stents"; The New England Journal of Medicine; bearing dates of Feb. 2, 2006 and Feb. 15, 2006; pp. 483-495; vol. 354;5; Massachusetts Medical Society.

Shabalovskaya, Svetlana, A.; "Surface, corrosion and biocompatibility aspects of Nitinol as an implant material"; Bio-Medical Materials and Engineering; bearing dates of Apr. 4, 2001, and 2002; pp. 69-109; vol. 12; IOS Press.

Smith, Michael; "PAS: Nasal Spray Flu Vaccine Seems Safe and Effective in Young"; May 2, 2006; pp. 1-2; MedPage Today, LLC; bearing dates of 2004-2006; printed on May 4, 2006; located at http://www.medpagetoday.com/tbprint.cfm?tbid=3213.

Snow, E.S.; Perkins, F.K.; Houser, E.J.; Badescu, S.C.; Reinecke, T. L.; "Chemical Detection with a Single-Walled Carbon Nanotube Capacitor"; Science; Mar. 25, 2005; pp. 1942-1945; vol. 307; www.sciencemag.org.

Stoeckel, Dieter; Pelton, Alan; Duerig, Tom; "Self-expanding nitinol stents: material and design considerations"; European Radiology; bearing dates of Jan. 28, 2003, May 22, 2003, Jul. 1, 2003, Sep. 3, 2003, Feb. 2004 and 2004; pp. 292-301(1-2); vol. 14, No. 2; Springer-Verlag GmbH-SpringerLink—Article; located at: http://www.springerlink.com/(lbegg455gtgifseqqptyb43m)/app/home/contribution.asp?referrer=parent&backto=issue,17,26;journal,27,147;browsepublicationsresults,444,1551; printed on Feb. 22, 2006.

Strauss, Bradley H., M.D., Ph.D.; Li, Chris, M.D.; Whittingham, Heather A., M.Sc; Tio, Fermin O., M.D.; Kutryk, Michael J.B., M.D., Ph.D.; Janicki, Christian, Ph.D.; Sparkes, John, D., M.Sc.; Turnlund, Todd, B.Sc.; Sweet, William L., M.D.; "Late Effects of Low-Energy Gamma-Emitting Stents in a Rabbit Iliac Artery Model"; Int. J. Radiation Oncology Biol. Phys.; bearing dates of Oct. 23, 2001, May 13, 2002 and May 15, 2002 and 2002; pp. 551-561; vol. 54, No. 2; Elsevier Science Inc.

Yusa, Go; Muraki, Koji; Takashina, Kei; Hashimoto, Katsushi; Hirayama, Yoshiro; "Controlled multiple quantum coherences of nuclear spins in a nanometre-scale device"; Nature; Apr. 21, 2005; pp. 1001-1005; vol. 434; 2005 Nature Publishing Group; www.nature.com/nature.

* cited by examiner

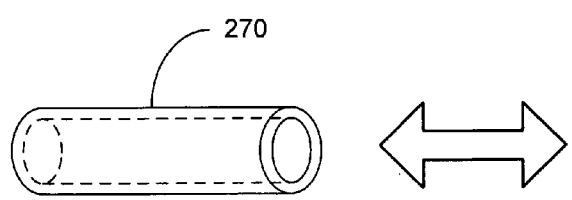
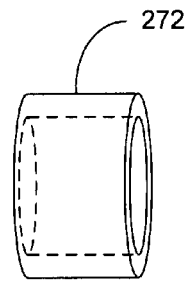
FIG. 19A          FIG. 19B
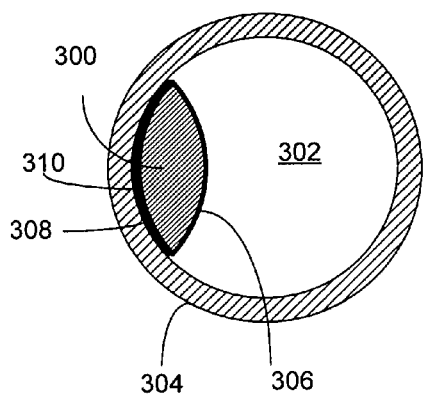
FIG. 20
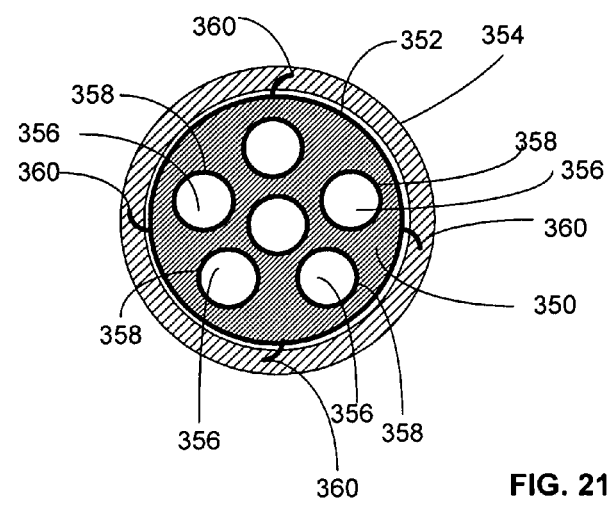
FIG. 21

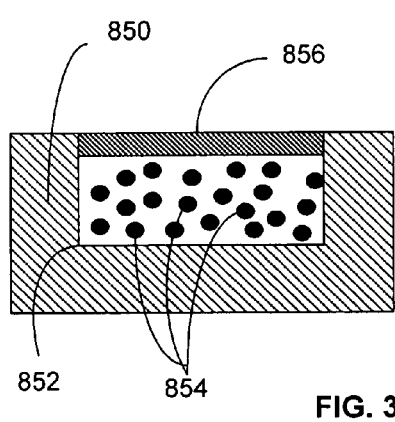
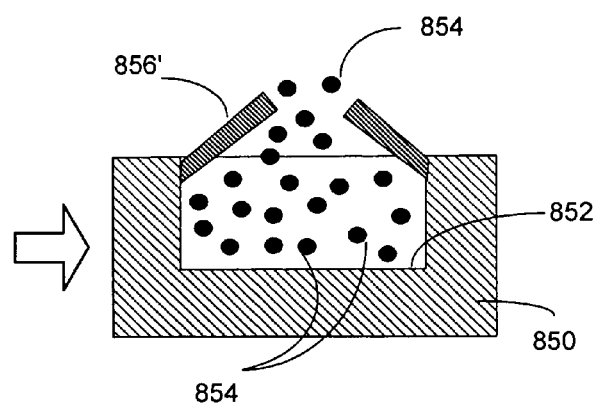
FIG. 34A     FIG. 34B
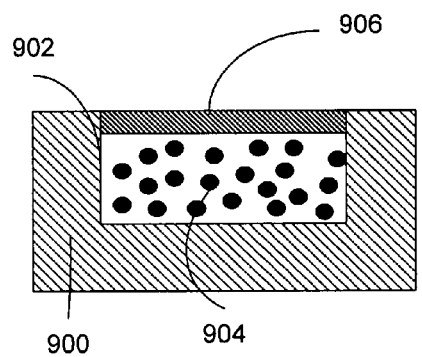
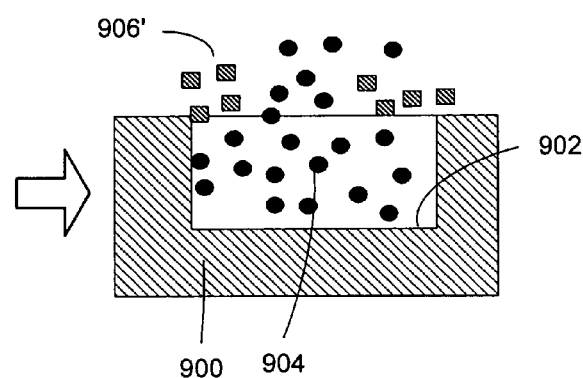
FIG. 35A     FIG. 35B
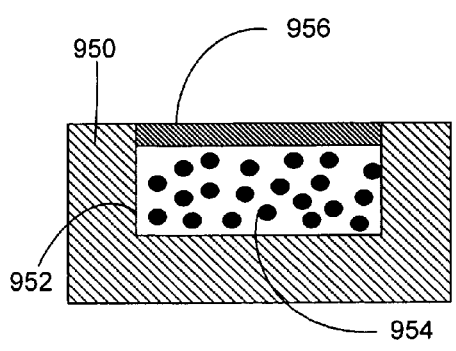
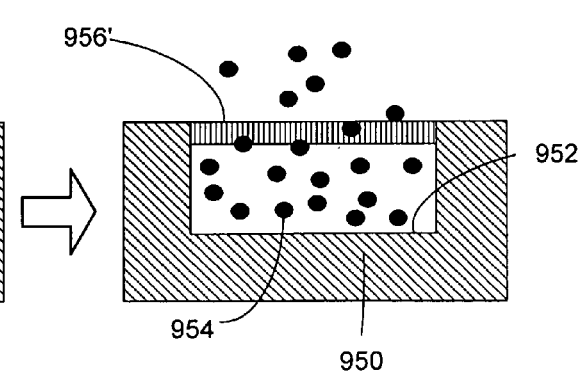
FIG. 36A     FIG. 36B

```
                              ┌─ 1700
                         ( Start )
                              │
                              ▼
┌─────────────────────────────────────────────────────────────────────────────┐
│ ┌──────────────────────┐  ┌──────────────────────┐  ┌──────────────────────┐│
│ │generate the delivery │  │                      │  │generate the delivery ││
│ │control signal with a │  │generate the delivery │  │control signal with   ││
│ │control signal        │  │control signal with   │  │control signal        ││
│ │generation circuitry  │  │control signal        │  │generation circuitry  ││
│ │in a remote device    │  │generation circuitry  │  │located at least in   ││
│ │and transmitting the  │  │in the delivery device│  │part at a location    ││
│ │delivery control      │  │ 1704                 │  │remote from the       ││
│ │signal to the         │  │                      │  │delivery portion of   ││
│ │delivery device       │  │                      │  │the delivery device   ││
│ │ 1702                 │  │                      │  │ 1706                 ││
│ └──────────────────────┘  └──────────────────────┘  └──────────────────────┘│
└─────────────────────────────────────────────────────────────────────────────┘
                              │                           ┌─ 1708
                              ▼
┌─────────────────────────────────────────────────────────────────────────────┐
│ release at least one material from a delivery portion of a delivery device  │
│ resident in a nasal region of a subject in response to a delivery control   │
│ signal corresponding to a desired release pattern                           │
└─────────────────────────────────────────────────────────────────────────────┘
                              │
                              ▼          ┌─ 1710
                           ( End )
```

FIG. 58

CONTROLLABLE RELEASE NASAL SYSTEM

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 10/949,186, entitled A CILIATED STENT-LIKE SYSTEM, naming Richa Wilson, Victoria Y. H. Wood, W. Daniel Hillis, Clarence T. Tegreene, Muriel Y. Ishikawa, and Lowell L. Wood, Jr. as inventors, filed 24 Sep. 2004, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 10/827,576, entitled A SYSTEM FOR PERFUSION MANAGEMENT, naming Lowell L. Wood, Jr. as inventor, filed 19 Apr. 2004, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 10/827,578, entitled A SYSTEM WITH A SENSOR FOR PERFUSION MANAGEMENT, naming Lowell L. Wood, Jr. as inventor, filed 19 Apr. 2004, which is currently co-pending, or is an application of which a currently co-pending application is entitled to the benefit of the filing date. For purposes of the USPTO extra-statutory requirements, the present application constitutes a continuation-in-part of U.S. patent application Ser. No. 10/827,572, entitled A SYSTEM WITH A RESERVOIR FOR PERFUSION MANAGEMENT, naming Lowell L. Wood, Jr. as inventor, filed 19 Apr. 2004, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 10/827,390, entitled A TELESCOPING PERFUSION MANAGEMENT SYSTEM, naming Lowell L. Wood, Jr. as inventor, filed 19 Apr. 2004, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/403,230, entitled LUMENALLY-ACTIVE DEVICE, naming Bran Ferren, W. Daniel Hillis, Roderick A. Hyde, Muriel Y. Ishikawa, Edward K. Y. Jung, Nathan P. Myhrvold, Elizabeth A. Sweeney, Clarence T. Tegreene, Richa Wilson, Lowell L. Wood, Jr. and Victoria Y. H. Wood as inventors, filed 12 Apr. 2006, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Devices and systems have been developed for use in various body lumens, particularly in the cardiovascular system, digestive, and urogenital tract. Catheters are used for performing a variety of sensing and material delivery tasks. Stents are implanted in blood vessels for the purpose of preventing stenosis or restenosis of blood vessels. Capsules containing sensing and imaging instrumentation, that may be swallowed by a subject and which travel passively through the digestive tract have also been developed. Robotic devices intended to move through the lower portion of the digestive tract under their own power are also under development.

SUMMARY

The present application describes devices, systems, and related methods for delivery of a material to a nasal region of a subject. Embodiments of delivery devices and systems for placement within a nasal region are disclosed. In one aspect, a system includes but is not limited to a structural element including a positioning portion configured for contacting an interior surface of a nasal region and mounting the structure element within the nasal region of a subject, a delivery portion mounted relative to the structural element and configured to release at least one material responsive to a delivery control signal, and control signal generation circuitry configured to generate a delivery control signal corresponding to a desired pattern of release of the at least one material into the nasal region. In addition to the foregoing, other system aspects are described in the claims, drawings, and text forming a part of the present disclosure.

In one aspect, a method includes but is not limited to releasing at least one material from a delivery portion of a delivery device mounted within a nasal region of a subject in response to a delivery control signal corresponding to a desired release pattern. The method may include sensing a parameter of interest in the nasal region with a sensor in the delivery device and controlling the release of the at least one material based upon the value of the parameter of interest. In some aspects, the method may include generating the delivery control signal. In addition to the foregoing, other method aspects are described in the claims, drawings, and text forming a part of the present disclosure.

Various aspects of the operation of such delivery devices may be performed under the control of hardware, software, firmware, or a combination thereof. In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. Software for operating a delivery device according to various embodiments is also described.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 19A and 19B depicted changes in dimension of an embodiment;

FIG. 20 is a cross-sectional view of an embodiment of a structural element;

FIG. 21 is a cross-sectional view of another embodiment of a structural element;

FIGS. 34A and 34B are depictions of the release of a stored deliverable material from a reservoir via a rupturable barrier;

FIGS. 35A and 35B are depictions of the release of a stored deliverable material from a reservoir via a degradable barrier;

FIGS. 36A and 36B are depictions of the release of a stored deliverable material from a reservoir via a barrier having controllable permeability;

FIG. 58 is a flow diagram of a method of delivering a material to a nasal region of a subject;

DETAILED DESCRIPTION

Figure 1:
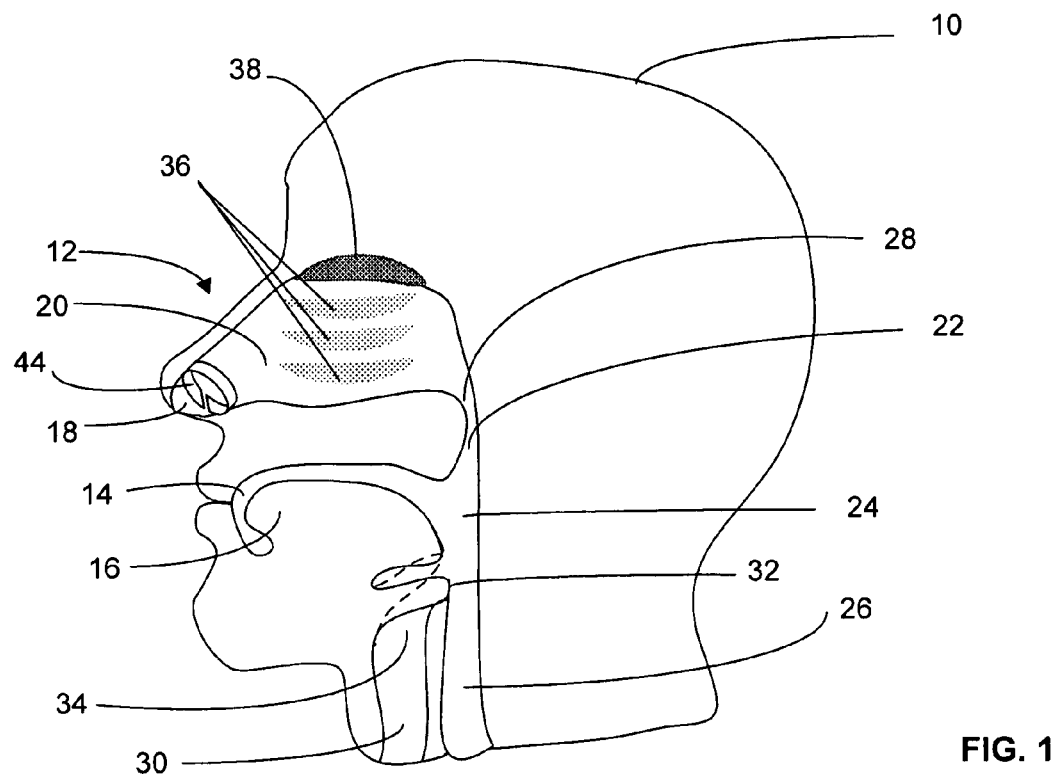
FIG. 1 is a side cross-sectional view of an embodiment of controllable release nasal device emplaced in a nostril.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 2:
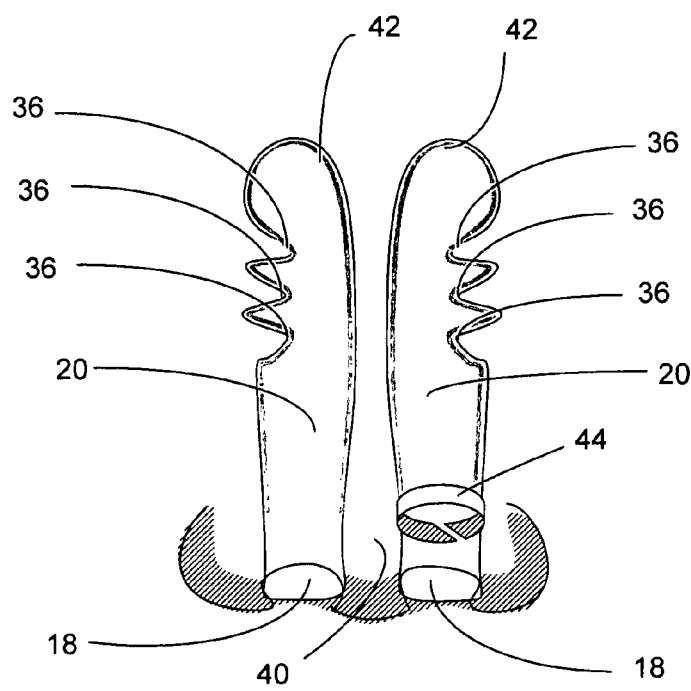
FIG. 2 is a front cross-sectional illustration of the controllable release nasal device depicted in FIG. 1.

FIG. 1 is a cross-sectional illustration of a head 10 of a person, showing the basic anatomy of nasal region 12. The mouth 14 and tongue 16 are also indicated in FIG. 1. Nasal region 12 includes nostril 18 and nasal cavity 20. Nasopharynx 22 is the uppermost portion of the pharynx (throat) 24, which connects to esophagus 26. Nasopharynx 22 connects to nasal cavity 20 via internal naris 28. Trachea (windpipe) 30 lies anterior to esophagus 26. Epiglottis 32 closes off the opening of larynx 34 leading to trachea 30 (shown with a solid line) during eating and drinking, and opens (shown with a dashed line) to permit the flow of air between pharynx 24 and trachea 30 during breathing. Nasal conchae 36 form shelf-like projections which may be seen more clearly in the front cross-sectional view of FIG. 2. The olfactory region 38 is located in the uppermost portion of nasal cavity 20. The nasal cavity 20 is divided into right side and left sides by nasal septum 40, as shown in FIG. 2. Nasal mucosa 42 lines the interior of the nasal cavity 20, as shown by a gray line in FIG. 2. (The nasal mucosa will not be indicated in other figures, but may be expected to be present within the nasal cavity under normal circumstances.)

In the example depicted in FIGS. 1 and 2, a delivery device 44 forming at least a portion of a controllable release nasal system is positioned within nostril 18 of nasal region 12. Delivery device 44 may be a self-expanding device that may be positioned within the nostril, for example by a care provider or by the person using the delivery device, and then may expand intrinsically or be made to expand under control to provide a snug fit sufficient to retain delivery device 40 within the nostril for as long as is desired.

Figure 3:
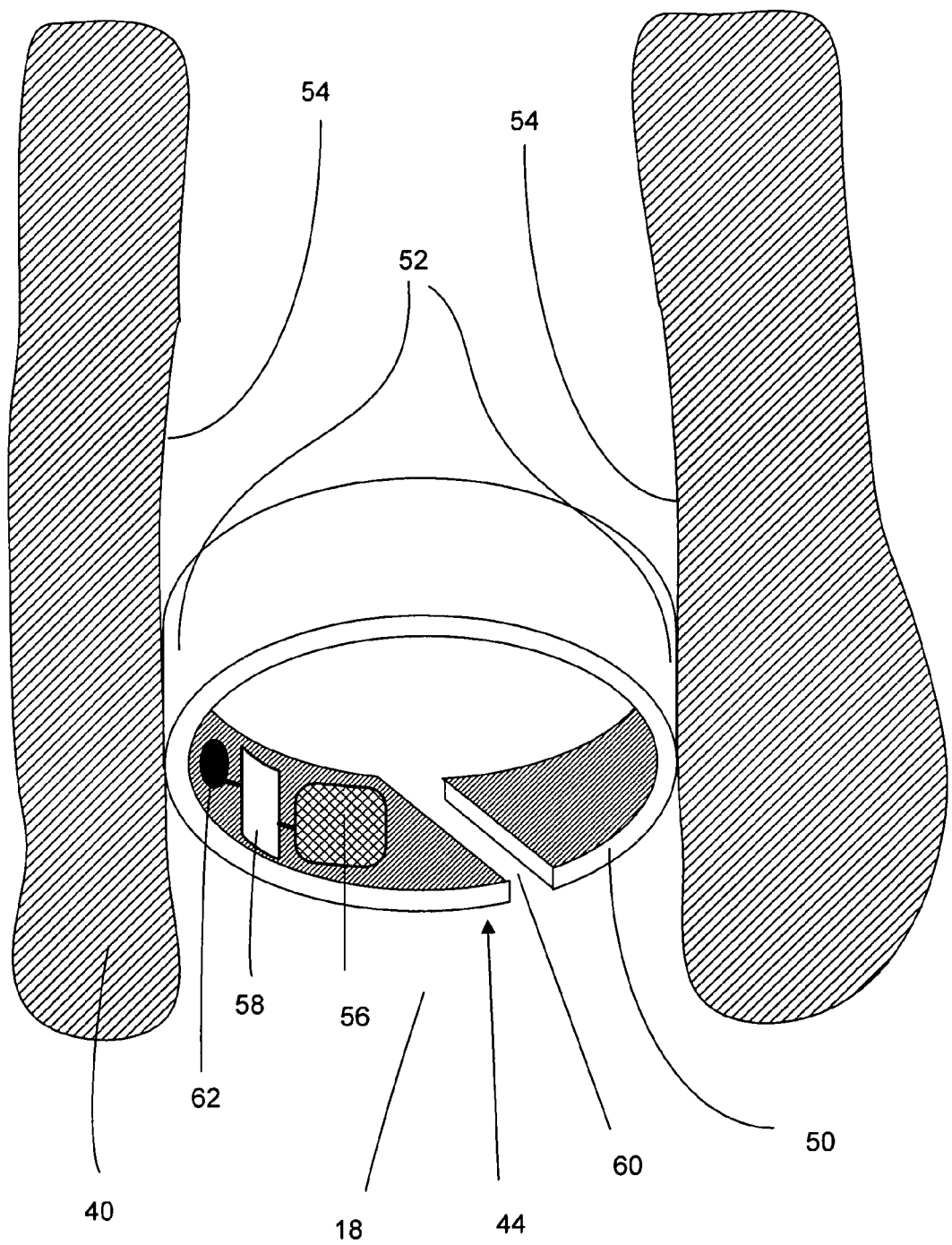
FIG. 3 is a detailed view of the controllable release nasal device shown in FIGS. 1 and 2.

FIG. 3 illustrates further aspects of delivery device 44. As shown in FIG. 3, in one aspect, an embodiment of a controllable release nasal system may include a structural element 50 including at least one positioning portion 52 configured for contacting an interior surface 54 of a nasal region (in this example, nostril 18) and mounting the structural element 50 within the nasal region of a subject; a delivery portion 56 mounted relative to the structural element 50 and configured to release at least one material responsive to a delivery control signal; and control signal generation circuitry 58 configured to generate a delivery control signal corresponding to a desired pattern of release of the at least one material into the nasal region. In the example of FIG. 3, positioning portion 52 is the exterior surface of structural element 50, which mounts structural element 50 within the nasal region (i.e., nostril 18 in this example) by a pressure and/or frictional fit. In other embodiments, other types of positioning portions may be used, as will be discussed herein. Delivery device 44 may include one or more sensor 62, which may be capable of detecting a physiological or environmental condition. Control signal generation circuitry 58 may receive as input a signal from sensor 62, which may be used in the calculation of the control signal for controlling the release of material from delivery portion 56.

A delivery portion of a controllable release nasal system (for example, delivery portion 56 of delivery device 44 in FIG. 3) may be designed to release material into different portions of the nasal region depending on various considerations, including the specific material being delivered, the intended effect of the material, sensed ambient physiological and/or environmental conditions, and, in some applications, the mechanism of absorption or uptake of the material by the body. In some embodiments, the material may be released directly into the nasal mucosa for absorption by local tissue or by blood circulating through local fine capillaries, while in other embodiments, the material may be released into the nasal cavity in the form of a liquid, a gas, finely dispersed particles or droplets, or mixtures thereof, which may be carried by ambient airflow to more distant portions of the nasal mucosa or other portions of the respiratory tract, which may be exhaled along with exhaled gases, or which may be inhaled to various depths of the bronchial tree or within or into the gas-exchange portions of the lung, for example. In some embodiments, the finely dispersed particles or droplets may be controlled to be within the diameter-range of 0.01 to 0.00001 cm, for example.

Materials delivered to the nasal regions may have a number of effects or uses. In some cases, materials such as odorants or neurotransmitters may stimulate the olfactory region to produce a sensory effect, for example for an esthetic, recreational, or medical purpose (e.g., aromatherapy; blockade, modification or enhancement of the flavors of foods, drinks, or orally delivered medications; one-or-more scents or olfactory modulators delivered according to a pattern or script in order to provide an olfactory analog to a soundtrack of a motion picture; amplified delivery of scents or odorants or olfactory modulators to supplement deficiencies or enhance to supra-normal levels the innate sense of smell, etc.). In some embodiments, materials may be released for delivery to the nasal mucosa and/or to sites elsewhere in the respiratory tract for absorption into the blood to affect systemic delivery of the materials, which may be, for example, various types of drugs, medications, contraceptives, hormones, vaccines, tolerance-inducing allergens, or therapeutic compounds. In some embodiments, materials may be delivered to the nasal mucosa or elsewhere in the respiratory tract to produce a local effect (e.g., to reduce inflammation or swelling of tissues, or for anti-pathogenic action) or inhaled into the lungs either to produce a local effect or for systemic uptake. In some embodiments, the material may form a functional coating on the surface of the nasal region, respiratory tract portion or lung, rather than be absorbed, e.g. to function as a surfactant, a protective layer, or a barrier. In some embodiments, one or more materials delivered into the nasal region may act on exhaled gases to act on or in cooperation with substances in the exhaled gases, for example to remove undesired materials from the exhaled gases, or to enhance, amplify or modify the effect of substances of interest in the exhaled gases.

Figure 4:
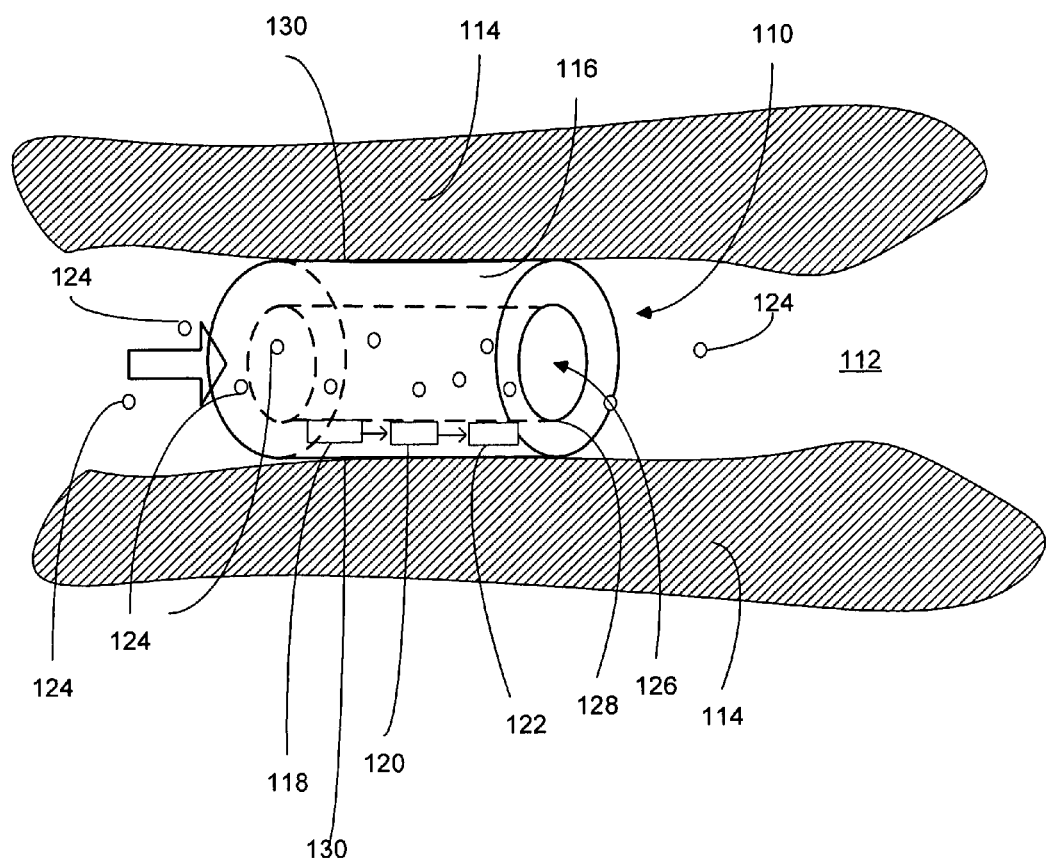
FIG. 4 is an illustration of a lumenally active device.

Some embodiments of controllable release nasal systems may be considered to be lumenally active devices. Lumenally active devices in general are described in commonly owned U.S. patent application Ser. No. 11/403,230, entitled "Lumenally Active Device" and filed Apr. 12, 2006, which is incorporated herein by reference. In some aspects, as described herein, controllable release nasal systems may release materials into a body lumen (e.g., a nasal cavity or nostril), while in other aspects, controllable release nasal systems may release materials into tissue surrounding the lumen and not into the lumen per se. The "Lumenally Active Device" patent application describes a lumenally active device which may include a structural element configured to fit within at least a portion of a body lumen, the structural element including a lumen-wall-engaging portion and a fluid-contacting portion configured to contact fluid within the body lumen; a sensor capable of detecting a condition of interest in the fluid; response initiation circuitry operatively connected to the sensor and configured to generate a response initiation signal upon detection of the condition of interest in the fluid by the sensor; and an active portion operatively connected to the response initiation circuitry and capable of producing a response upon receipt of the response initiation signal. Such a system is depicted in FIG. 4, which shows a delivery device 110 positioned in a body lumen 112. Body lumen 112 is defined by wall portions 114, which may be the walls of lumen-containing structure within the body of an organism, e.g., a nasal region or, in other embodiments and applications, a blood vessel or other lumen containing structure. Delivery device 110 includes structural element 116, sensor 118, response initiation circuitry 120, and active portion 122. A fluid may flow through lumen 112. The term fluid, as used herein, may refer to liquids, gases, and other compositions, mixtures, or materials exhibiting fluid behavior. The fluid within the body lumen may include a liquid, or a gas or gaseous mixtures. As used herein, the term fluid may encompass liquids, gases, or mixtures thereof that also include solid particles in a fluid carrier. Liquids may include mixtures of two or more different liquids, solutions, slurries, or suspensions. Examples of liquids present within body lumens include blood, lymph, serum, urine, semen, digestive fluids, tears, saliva, mucus, cerebro-spinal fluid, intestinal contents, bile, epithelial exudate, or esophageal contents. Liquids present within body lumens may include synthetic or introduced liquids, such as blood, substitutes or drug, nutrient, or (possibly buffered) saline or electrolyte solutions. Fluids may include liquids containing dissolved gases or gas bubbles, or gases containing fine liquid droplets or solid particles. Gases or gaseous mixtures found within body lumens may include inhaled and exhaled air, e.g. in the nasal or respiratory tract, or intestinal gases. According to this definition, fluids within the nasal region will typically include gases and mixtures of gases. Fluid may flow through the central openings 126 of structural element 116, with the interior surface of structural element 116 forming fluid-contacting surface 128. In the embodiment of FIG. 4, sensor 118 and active portion 122 may be located at a fluid-contacting surface 128. Outer surface 130 of structural element 116 may function as a lumen-wall engaging portion, providing a frictional fit with wall portions 114. In other embodiments of delivery devices, other structures and methods for engaging the lumen wall may be employed. Structural elements may include two or more openings or lumens passing through the structural element, rather than a single central opening as depicted in FIG. 4, and the lumen-wall-engaging portion of the structural element is not limited to embodiments having a substantially smooth outer surface that conforms to the interior cross-section of a nasal lumen, but may have a variety of surface shapes, textures, and contours, some of which may conform or contact only a portion or portions of the interior cross section of a nasal lumen.

Embodiments of the lumenally-active system may be configured for use in various different body lumens of an organism including, for example, a nostril or nasal cavity, one or more portions of the respiratory tract, the cardiovascular system (e.g., a blood vessel), the lymphatic system, the biliary tract, the urogenital tract, the oral cavity, the digestive tract, the tear ducts, a glandular system, a reproductive tract or portion thereof, the cerebral ventricles, spinal canal, and other fluid-containing structure of the nervous system of an organism. Other fluid-containing lumens within the body may be found in the auditory or visual systems, or in interconnections thereof, e.g., the Eustachian tubes.

Wherever a controllable release nasal system is to be used, the dimensions and mechanical properties (e.g., rigidity) of the delivery device, and particularly of the structural element of the delivery device, may be selected for compatibility with the location of use, in order to provide for reliable positioning of the device and to prevent damage to the lumen-containing structure.

The structural element may include a self-expanding structure configured to expand to mount the structural element within the nasal region of the subject. For example, structural element 50 of the delivery device depicted in FIGS. 1 through 3 is a generally spring-like structure that may be formed of a loop of resilient, springy, or self-expanding material which may be compressed slightly by virtue of slit 60, as shown in FIG. 3, to permit insertion into the nostril and which may then expand sufficiently to cause the structural element to be retained within the nostril until it is to be removed. In such embodiments, the resilient, springy or self-expanding portion of the structural element may function as the positioning portion of the delivery device.

Figure 5:
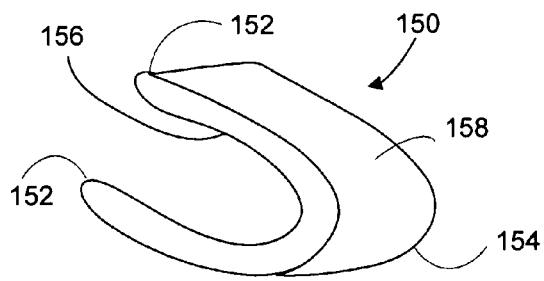
FIG. 5 is an illustration of another embodiment of a controllable release nasal device.
Figure 6:
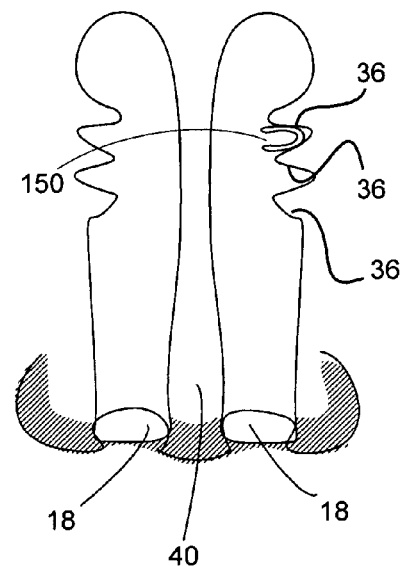
FIG. 6 is a front cross-section view of the device of FIG. 5.
Figure 7:
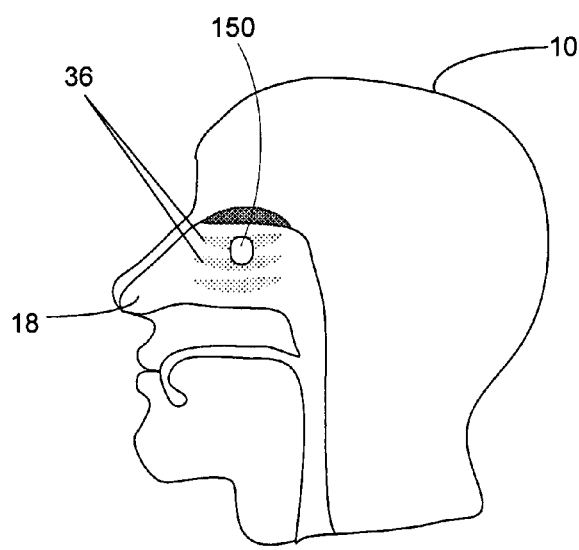
FIG. 7 is a further depiction of the device of FIG. 6.

FIGS. 5 through 7 depict a further spring-like structural element which may be placed between the nasal conchae and which may expand slightly to secure it in place. FIG. 5 depicts structural element 150. Structural element 150 includes end regions 152, curved portion 154, inner surface 156 and outer surface 158. Structural element 150 may also include a delivery portion and control signal generation circuitry (not shown). Structural element 150 may be compressed by pressing together end regions 152. As shown in FIG. 6, structural element 150 may be inserted between two nasal conchae 36, and allowed to expand to hold it in place. The position of structural element 150 relative to nostrils 18, nasal septum 40, and nasal conchae 36, can be seen in both FIG. 6 and FIG. 7.

The self-expanding structure may permit the structural element to be placed within a nasal region (e.g., a nostril, or a portion of a nasal cavity) while in a first, contracted, state and then transformed into a second, expanded, state of a nature such that the structural element contacts opposing interior walls of a portion of the nasal region in order to satisfactorily position and mount the structural element at least temporarily within the nasal region.

Figure 8:
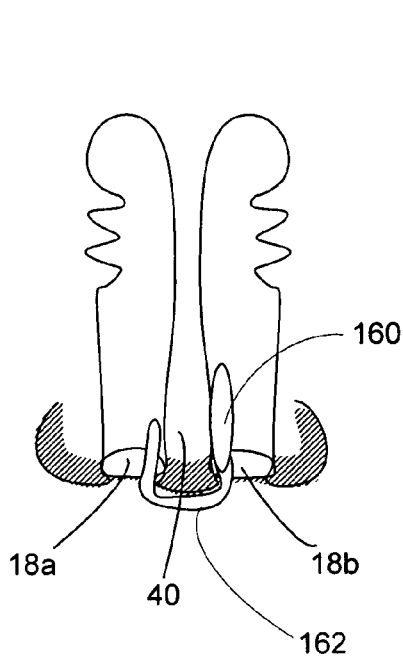
FIG. 8 is a front cross-sectional view of an embodiment of a controllable release nasal device including a clip.
Figure 9:
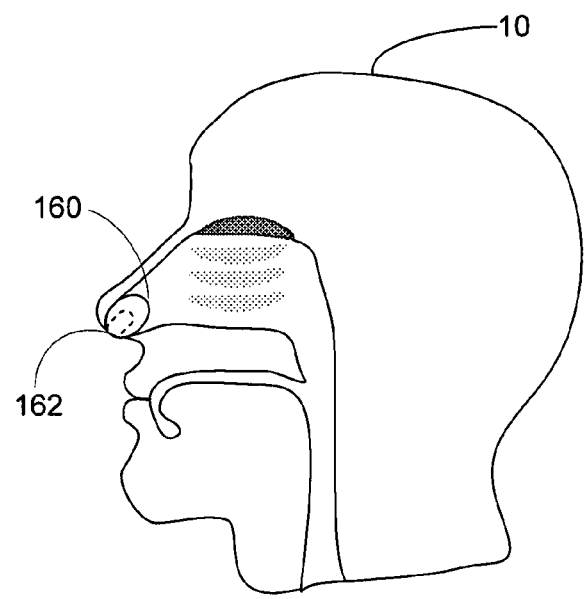
FIG. 9 is a side cross-sectional view of the embodiment of FIG. 8.

In some embodiments, as depicted in FIGS. 8 and 9, a structural element 160 may include a clip structure 162, at least a portion of which is configured to extend outside the nasal region of the subject. In FIG. 8, clip structure 162 clamps onto nasal septum 40, with a portion projecting into a first nostril 18*a*, with structural element 160 residing within second nostril 18*b*. Construction of clip structures of this general type may be as described, for example, in U.S. Pat. No. 5,947,119, which is incorporated herein by reference. In the embodiment shown in FIG. 8, a single structural element 160 is shown. In other embodiments (not shown), a clip structure may have associated with it two or more structural elements, with one residing in each nostril. In still other embodiments, two or more structural elements may reside in an individual nostril, or in both nostrils. FIG. 9 is a side view of structural element 160 with clip structure 162.

In some embodiments, a controllable release nasal system may be configured to reside entirely within the nasal region of the subject. In other embodiments of a controllable release nasal system, a first portion of the controllable release nasal system may be configured to reside within the nasal region of the subject and a second portion of the controllable release nasal system may be configured to reside external to the nasal region of the subject. The second portion may be simply structural, like the extra-nasal portion depicted in FIG. 8. However, in some embodiments, the second portion of the controllable release nasal system may include components such as the control signal generation circuitry or a source of the material delivered by the device (or a component thereof).

Figure 10:
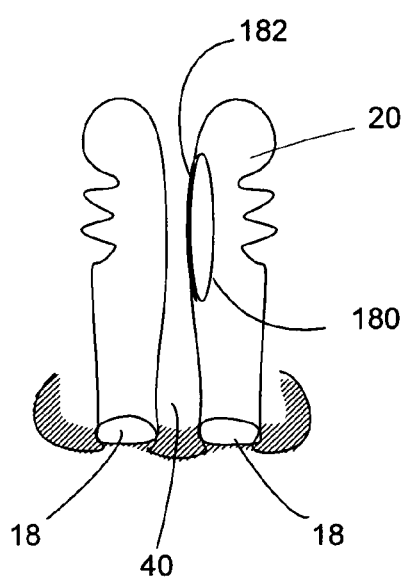
FIG. 10 is a front cross-sectional view of another embodiment of a controllable release nasal device.
Figure 11:
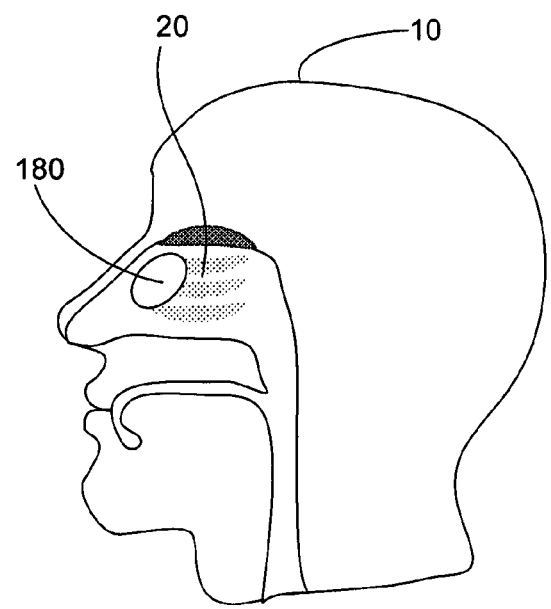
FIG. 11 is a side cross-sectional view of the embodiment of FIG. 10.

FIGS. 10 and 11 depict an embodiment of a structural element 180 in which the positioning portion may include an adhesive 182. As shown in the front sectional view of FIG. 10, structural element 180 is located in nasal cavity 20 and positioned against nasal septum 40 with a layer of adhesive 182. The side sectional view of FIG. 11 illustrates the position of structural element 180 within nasal cavity 20. In other embodiments, the positioning portion may include a remotely guidable section and/or a means for facilitating extraction when it is desired to remove the structural element or device from the nasal region. In some embodiments, the positioning portion may include other structures for mounting or positioning the structural element within at least a part of a nasal region. The positioning portion may include one or more barb-like structures (e.g., as depicted in FIG. 21), at least one vacuum-generating device capable of mounting the structural element within a nasal region by producing sufficient vacuum (or suction) to cause the structural element to stick to at least a portion of the nasal region, or at least one hair-engaging structure (which may be, for example, a clip, clasp, grip or coil-like structure capable of reversibly engaging one or more hairs within the nasal region to mount the structural element within the nasal region).

In the various embodiments disclosed herein, the positioning portion may be used to mount the structural element of the delivery device within a nasal region for a use period that may be brief (e.g. on the order of minutes) or extended (weeks, months, or longer). Following placement of the structural element in the desired location for use, which may be done manually or with the use of an insertion device, the delivery device may be held in place without further intervention. The positioning portion may include any fastening structure or mechanism that is capable of mounting (securing, retaining and/or supporting) the structural element within the nasal region for the duration of its use without the need for the person using the device (or another party) to hold or otherwise maintain the structural element in place.

As shown variously in FIGS. 1 through 11, in some embodiments, at least a part of the structural element may be configured for mounting within a nostril of the subject, and in some embodiments at least a part of the structural element may be configured for mounting within a nasal cavity of the subject.

Figure 12:
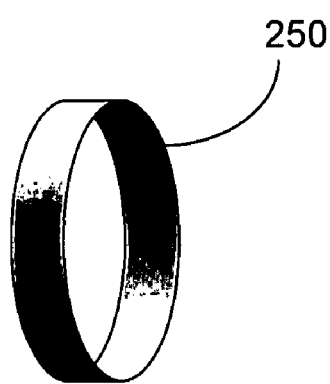
FIG. 12 is an illustration of an embodiment of a structural element.
Figure 13:
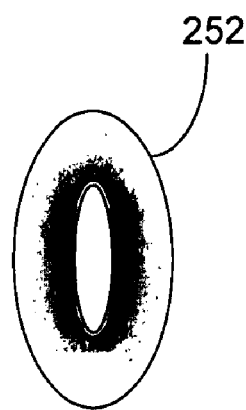
FIG. 13 is an illustration of another embodiment of a structural element.
Figure 14:
FIG. 14 is an illustration of another embodiment of a structural element.
Figure 15:
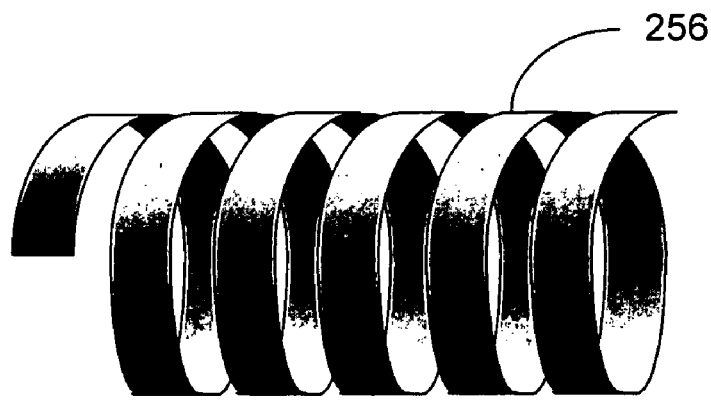
FIG. 15 is an illustration of another embodiment of a structural element.

FIGS. 12 through 15 depict a number of possible configurations for structural elements of delivery devices for use in body lumens. Structural elements may have the form of a short cylinder 250, as shown in FIG. 12; an annulus 252, as shown in FIG. 13; a cylinder 254, as shown in FIG. 14; or a spiral 256, as shown in FIG. 15. Elongated forms such as cylinder 254 or spiral 256 may be suitable for use in generally tubular portions of lumen-containing structures such as the nostrils, possibly with a significant taper over their length (not shown in FIGS. 14-15). Structural elements may be formed from various materials, including metals, polymers, fabrics, and various composite materials, including ones of either inorganic or organic character, the latter including materials of both biologic and abiologic origin, selected to provide suitable biocompatibility and mechanical properties.

Figure 16:
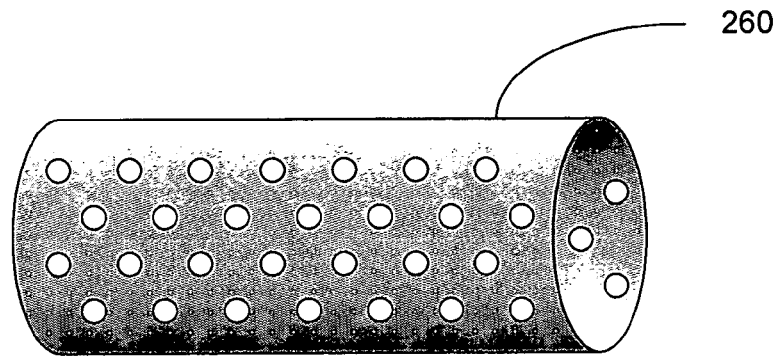
FIG. 16 is an illustration of a further embodiment of a structural element.
Figure 17:
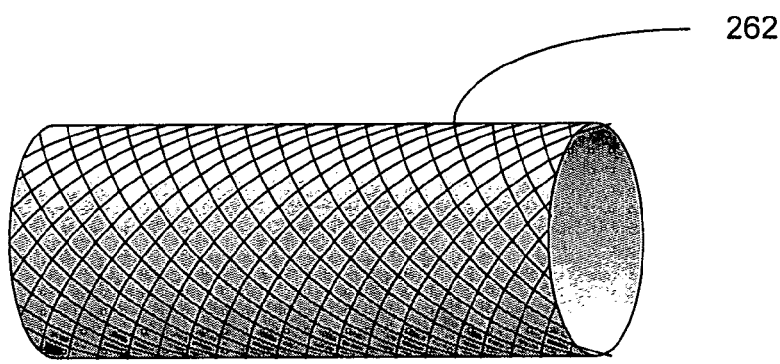
FIG. 17 is an illustration of another embodiment of a structural element.
Figure 18:
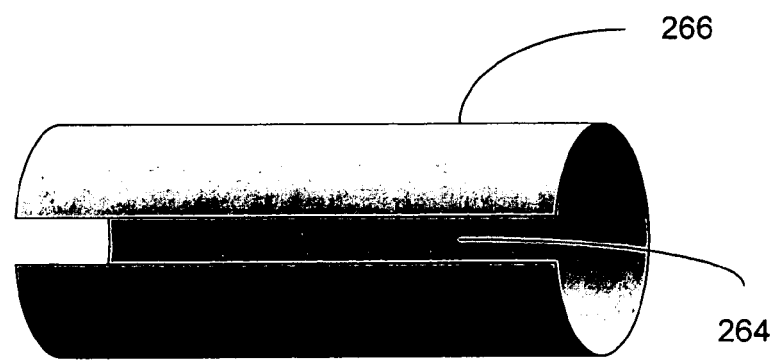
FIG. 18 is an illustration of another embodiment of a structural element.

As shown in FIGS. 16-18, the basic form of a structural element may be subject to different variations, e.g., by perforations, as shown in structural element 260 in FIG. 16; a mesh structure, as shown in structural element 262 in FIG. 16; or the inclusion of one or more slots 264 in structural element 266 in FIG. 18. Slot 264 runs along the entire length of structural element 266; in other embodiments, one or more slots (or mesh or perforations) may be present in only a portion of the structural element. By using spiral, mesh, or slotted structural elements (as in FIGS. 15, 17, and 18) formed from resilient, elastic, springy or self-expanding/self-contracting materials or substrates, suitable structural elements may be formed. Spiral, mesh, or slotted elements need not be elongated tubular structures as depicted in FIGS. 15, 17, and 18, but may be shorter, generally ring-like structures similar in profile to the structural element shown in FIGS. 1 through 3, which is essentially a spring having only a single loop.

A self-expanding or contracting structural element may facilitate positioning or secure emplacement of the structural element within a body lumen of an organism, such as a nasal structure. In some embodiments, flexible material having adjustable diameter, taper, and length properties may be used. For example, some materials may change from a longer, narrower configuration 270 as shown in FIG. 19A, to a shorter, wider configuration 272 as shown in FIG. 19B, or may taper over their length. Structural elements that may exhibit this type of expansion/contraction property may include mesh structures formed of various metals or plastics, and some polymeric materials, for example.

The exemplary embodiments depicted in FIGS. 1-4 and 12-19B either are substantially cylindrical, and hollow and tubular in configuration, or ring-like, with a single central opening. Thus, the exterior of the cylindrical or ring-like structural element may contact and engage the wall of the body lumen, and the interior of the structural element (within the single central opening) may form a fluid-contacting portion of the structural element. Structural elements are not limited to cylindrical or ring-like structural elements having a single central opening, however.

FIGS. 20 through 25 depict a variety of cross-sectional configurations for structural elements of delivery devices. Note that the illustrated cross-sectional configurations are suitable to be fit into a lumen having a roughly circular cross-section, as would be the case, for example, with a nostril viewed from above or below. Analogous structures may be designed to fit within lumens having non-circular cross-sections. In FIG. 20, a delivery device 300 is positioned in lumen 302 of lumen-containing structure 304. In this embodiment, fluid-contacting portion 306 may be the surface of structural element 300 that faces lumen 302, while the lumen-wall engaging portion 308 may be a layer of tissue adhesive on surface 310 of structural element 300. An example of a device having a cross-section similar to that shown in FIG. 20, is the embodiment shown in FIGS. 10 and 11.

FIG. 21 depicts in cross-section a further embodiment of a structural element 350 in lumen 352 of lumen-containing structure 354. Structural element 350 includes multiple openings 356, each of which includes an interior surface 358 that forms a fluid-contacting portion. Structural element 350 may include one or more barb-like structures 360 that serve as lumen-wall engaging portions that maintain structural element 350 in position with respect to lumen-containing structure 354. Barb like structures may be fixed in some embodiments, or retractable or moveable in other embodiments.

Figure 22:
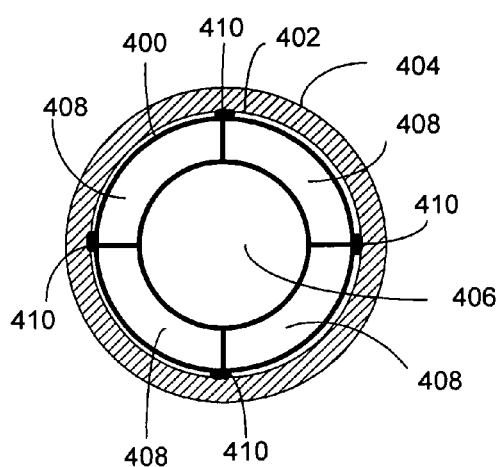
FIG. 22 is a cross-sectional view of another embodiment of a structural element.

FIG. 22 depicts in cross-section an embodiment of a structural element 400 in lumen 402 of lumen-containing structure 404. Structural element 400 includes a large central opening 406 and multiple surrounding openings 408. The interior surface of each opening 406 or 408 serves as a fluid-contacting portion, while projections 410 function as lumen-wall engaging portions, which may engage frictionally or may project slightly into the interior of the wall of lumen-containing structure 404.

Figure 23:
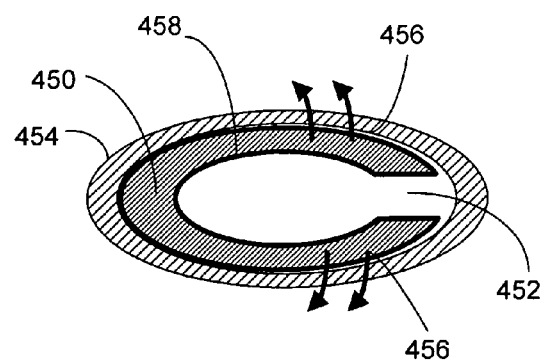
FIG. 23 is a cross-sectional view of another embodiment of a structural element.

FIG. 23 depicts a further embodiment in which structural element 450 has a substantially oval cross-section and includes a slot 452. Lumen-containing structure 454 may be generally oval in cross section, or may be flexible enough to be deformed to the shape of structural element 450. Structural element 450 may be a compressed spring-like structure that produces outward forces as indicated by the black arrows, so that end portions 456 of structural element 450 thus press against and engage the lumen wall. Interior surface 458 of structural element 450 serves as the fluid-contacting portion of structural element 450.

Figure 24:
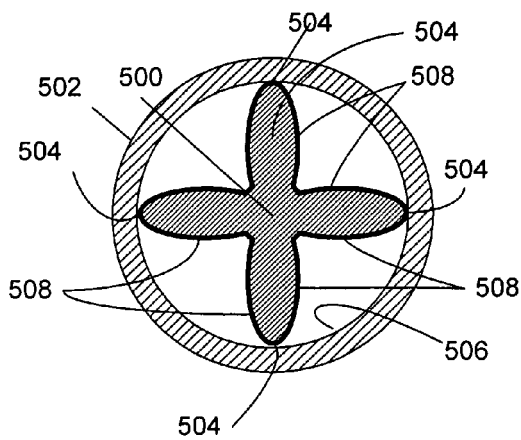
FIG. 24 is a cross-sectional view of another embodiment of a structural element.

FIG. 24 is a cross-sectional view of a structural element 500 in a lumen-containing structure 502. Structural element 500 includes multiple projecting arms 504 which contact lumen wall 506 of lumen-containing structure 502, and function as lumen-wall engaging portions. Inner surfaces 508 of arms 504 function as fluid-contacting portions of structural element 500.

Figure 25:
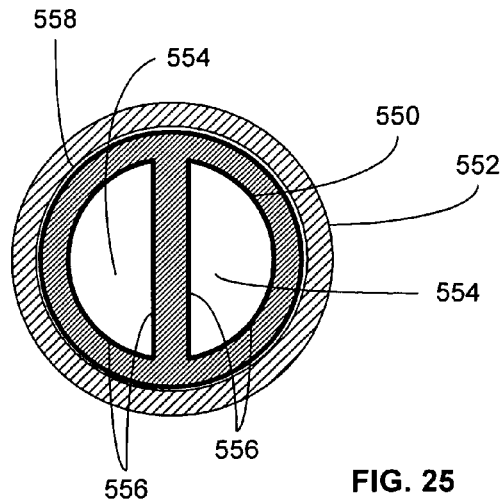
FIG. 25 is a cross-sectional view of yet another embodiment of a structural element.

FIG. 25 depicts (in cross-section) another example of a structural element 550 positioned within a lumen-containing structure 552. Structural element 550 includes two openings 554. The interior surfaces 556 of openings 554 function as fluid-contacting portions, while the outer surface 558 of structural element 550 serves as a lumen-wall engaging portion.

The structural elements depicted in FIGS. 1-25 are intended to serve as examples, and are in no way limiting. The choice of structural element size and configuration appropriate for a particular body lumen may be selected by a person of skill in the art. Structural elements may be constructed by a variety of manufacturing methods, from a variety of materials. Appropriate materials may include metals, ceramics, polymers, and composite materials having suitable biocompatibility, sterilizability, mechanical, and physical properties, as will be known to those of skill in the art. Examples of materials and selection criteria are described, for example, in *The Biomedical Engineering Handbook*, Second Edition, Volume I, J. D. Bronzino, Ed., Copyright 2000, CRC Press LLC, pp. IV-1-43-31. Manufacturing techniques may include injection molding, extrusion, die-cutting, rapid-prototyping, or self-assembly, for example, and will depend on the choice of material and device size and configuration. Sensing and active portions of the delivery device as well as associated electrical circuitry may be fabricated on the structural element using various microfabrication and/or MEMS techniques, or may be constructed separately and subsequently assembled to the structural element, as one or more distinct components.

In a controllable release nasal device or system, a fluid contacting portion typically contacts inspired or expired air/gases moving through the nasal region, while a lumen wall engaging portion may contact the tissue lining the wall of the nostril or the nasal cavity. In some embodiments, the lumen wall-engaging portion may closely contact the nasal mucosa, and/or may be in proximity to capillary beds in the nasal mucosa. In some embodiments of a controllable release nasal device or system, a lumen wall engaging portion may be in proximity to neural tissue in the olfactory region. Contact with or proximity to mucosa, capillaries, and/or neural tissue by the lumen wall engaging portion of a controllable release nasal device or system may facilitate the release or transfer of material to some or all of these tissues by a delivery portion located on the lumen wall engaging portion, or the sensing of various parameters regarding or pertinent to these tissues by a sensing portion. Similarly, contact or proximity of a fluid-contacting portion of a controllable release nasal device or system to a fluid mixture (i.e., gases, fine particles, liquid droplets, etc.) within the nostrils or nasal cavity may facilitate the release of materials into the fluid mixture by a delivery portion located on the fluid-contacting portion, or the sensing of various parameters pertinent to the fluid mixture by a sensing function.

Figure 26:
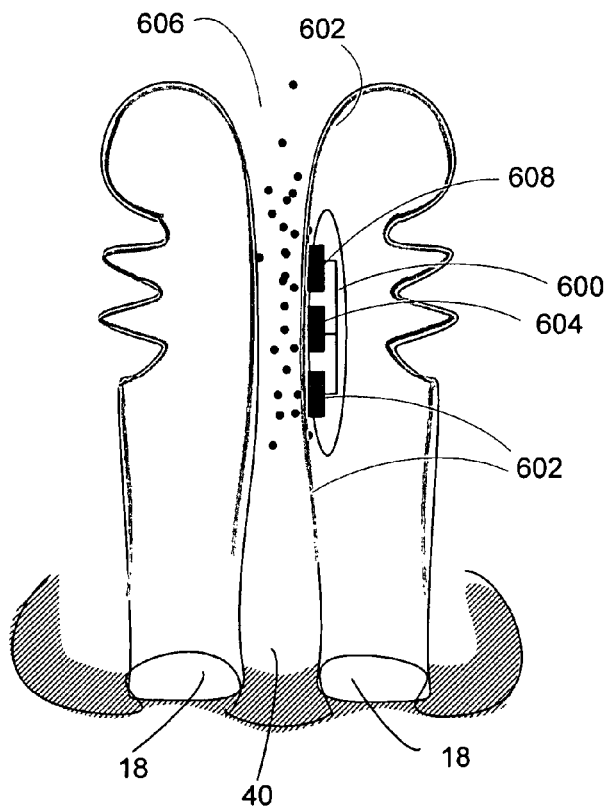
FIG. 26 is a front cross-sectional depiction of release of material from a controllable release nasal device.

The delivery portion may be configured to release the at least one material directly into the nasal mucosa for absorption in some embodiment, as illustrated in FIG. 26. Structural element 600, which is similar to that depicted in FIGS. 10 and 11, may be positioned against nasal mucosa 602 on the surface of nasal septum 40, so that delivery portion 604 is positioned adjacent to nasal mucosa 602. Material 606 released from delivery portion 604 may then be absorbed into nasal mucosa 602. Control signal generation circuitry 608 on structural element 600 may generate a control signal that stimulates release of material 606 from delivery portion 604. In some such embodiments, the delivery portion may include a permeation enhancer (that may be released in association with the material being delivered, for example) that is capable of increasing the permeation of the at least one material into the nasal mucosa. Permeation enhancers may include chemical permeation enhancers such as isopropyl myristate, bile salts, surfactants, fatty acids and derivatives, chelators, cyclodextrins or chitosan, as described in Murthy, S. N. Hiremath, S. R. R. "*Physical and Chemical Permeation Enhancers in Transdermal Delivery of Terbutaline Sulphate,*" AAPS PharmSciTech., 2001, 2(1) or Senel, S. Hincal, A. A. "*Drug*

*permeation enhancement via buccal route: possibilities and limitations,"* J. Control Release, 2001 May 14, 72(1-3):133-44, both of which are incorporated herein by reference. Permeation may also be enhanced by including a magnetic component, as described in Murthy, S. N., Hiremath, S. R. R. *"Physical and Chemical Permeation Enhancers in Transdermal Delivery of Terbutaline Sulphate,"* AAPS PharmSciTech., 2001, 2(1), or by the use of microprotrusions of the type described in U.S. Pat. No. 6,953,589, or other microneedles or microfine lances. The foregoing references are incorporated herein by reference. Other technologies that may used for enhancing permeability of materials include, but are not limited to, iontophoresis, microdialysis, ultrafiltration, electromagnetic, osmotic, electroosmosis, sonophoresis, microdialysis, suction, electroporation, thermal poration, microporation, microfine cannulas, skin permeabilization, or a laser.

Figure 27:
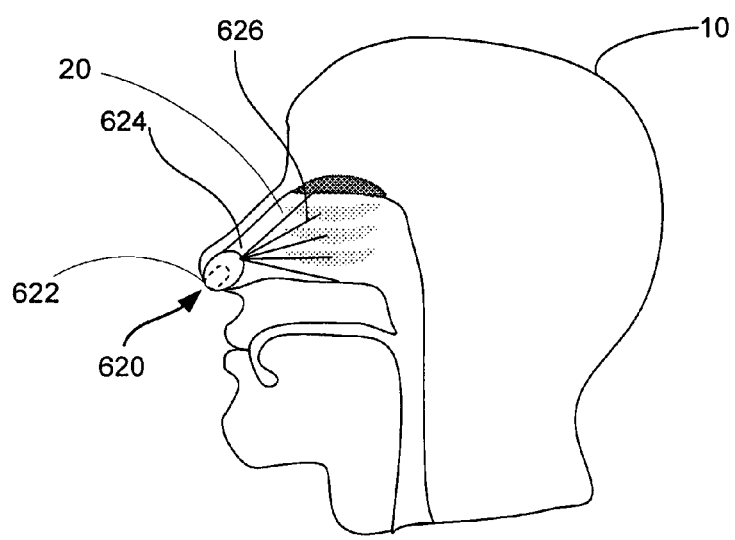
FIG. 27 is a side cross-sectional view of delivery of material to the nasal mucosa from a controllable release nasal device.
Figure 28:
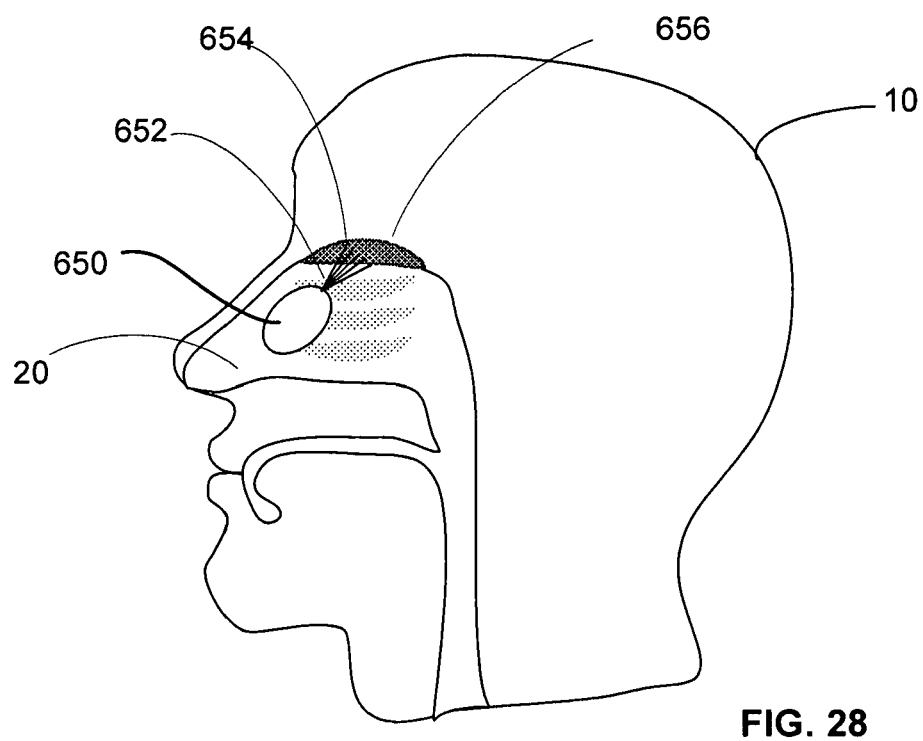
FIG. 28 is a side cross-sectional view of delivery of material to the olfactory region from a controllable release nasal device.
Figure 29:
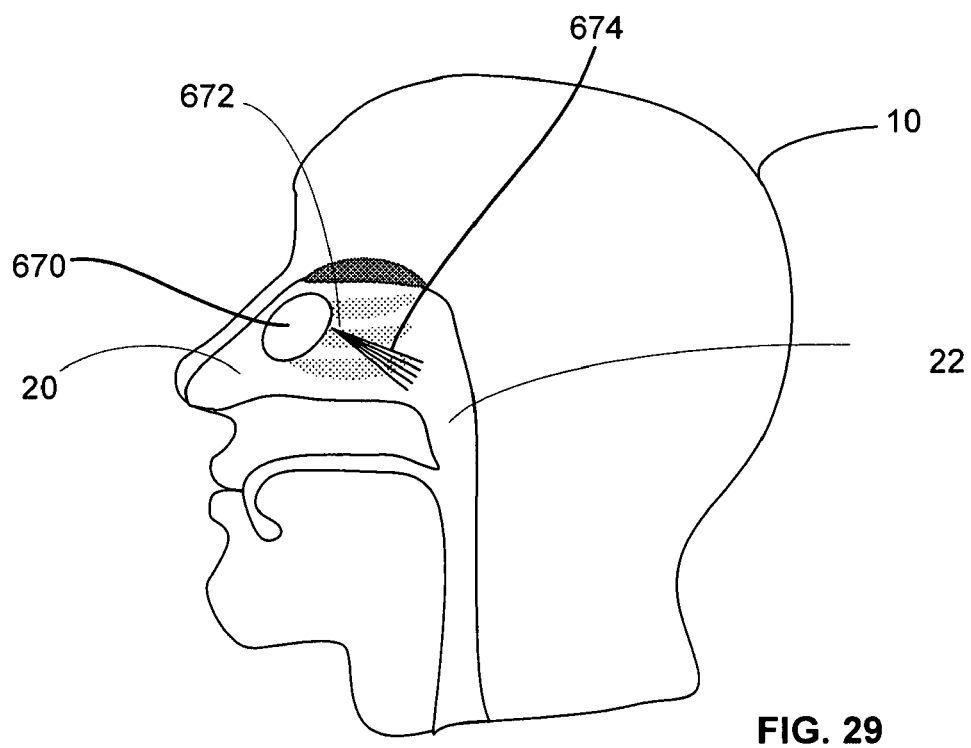
FIG. 29 is a side cross-sectional view of delivery of material toward the nasopharynx from a controllable release nasal device.

As illustrated in FIG. 27, in other embodiments, the delivery portion may be configured to release the at least one material into the nasal cavity in the form of a spray or similar aero-suspension of finely dispersed particles, powders or droplets. In FIG. 27, delivery device 620 includes structural element 622 similar to structural element 160 in FIGS. 8 and 9. Delivery portion 624 of delivery device 620 is configured to direct the release of the at least one material 626 toward the nasal mucosa, e.g. in the interior of nasal cavity 20. In other embodiments, as shown in FIG. 28, delivery device 650 may include delivery portion 652 configured to direct the release of the at least one material 654 toward the olfactory portion 656 of the nasal mucosa. In still other embodiments, as shown in FIG. 29, a delivery device 670 may include a delivery portion 672 configured to direct the release of the at least one material 674 toward the nasopharynx 22. Material directed toward nasopharynx may subsequently be inhaled into the other portions of the respiratory tract, including the lungs, of the person in which delivery device 670 is emplaced, and it may be configured for preferential delivery to or deposition onto one or more surfaces of particular portions thereof.

In other embodiments, the active portion of a delivery device may include a material release structure operatively coupled to the response initiation circuitry and configured to release a material in response to detection of a condition of interest. A condition of interest may be detected by a sensor, which may be located in or on the release delivery device.

Figure 30:
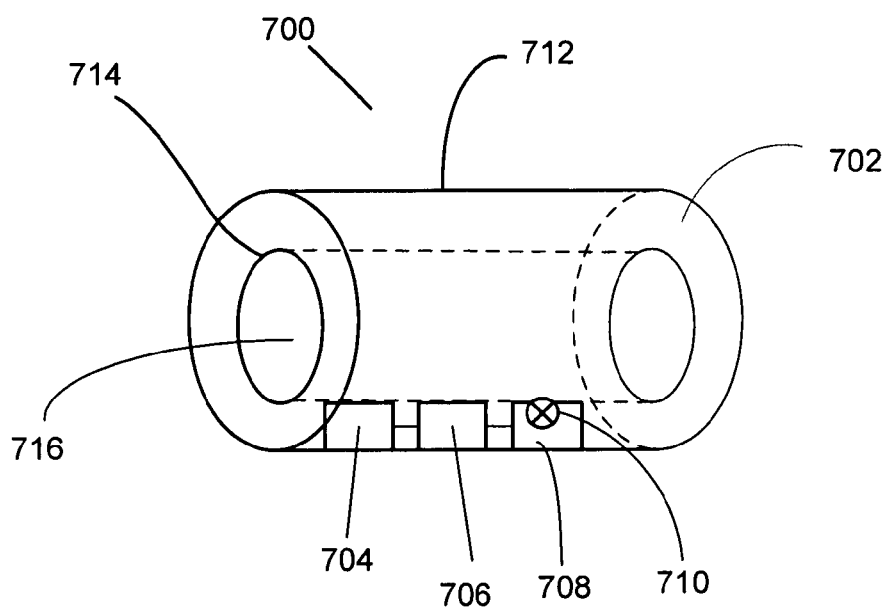
FIG. 30 is an illustration of a device including stored deliverable material.

FIG. 30 depicts a delivery device 700 including a structural element 702, sensor 704, control signal generation circuitry 706, and release structure 708 including release mechanism 710. Structural element 702 includes external surface 712, configured to fit within a body lumen, and internal surface 714 defining central opening 716, through which a fluid may flow. Upon sensing of a condition of interest in the fluid by sensor 704, control signal generation circuitry 706 may cause release of material from material release structure 708 by activating release mechanism 710. Release mechanism 710 may include a variety of different types of release mechanisms, including, for example a controllable valve as depicted in FIG. 30. Various types of valves and microvalves are known to those of skill in the art, and may be used to regulate the release of material from material release structure 708 in response to a control signal from control signal generation circuitry 706. Control signal generation circuitry 706 may activate release mechanism 710 by supplying a delivery control signal, which may be an electrical signal, for example. In some embodiments, other types of delivery control signals, including magnetic signals, optical signals, acoustic signals, or other types of signals may be used. Combinations of several types of signals may be used in some embodiments. In some embodiments, control signal generation circuitry 706 may cause release of material from material release structure in response to passage of a certain amount of time, as monitored, for example, by a timekeeping device. In some embodiments, material release structure 708 may include a pressurized reservoir of material. In still other embodiments, the material (or materials) to be released may be generated within the material release structure. In other embodiments, the material(s) may diffuse away from the release structure along a concentration gradient.

Figure 31:
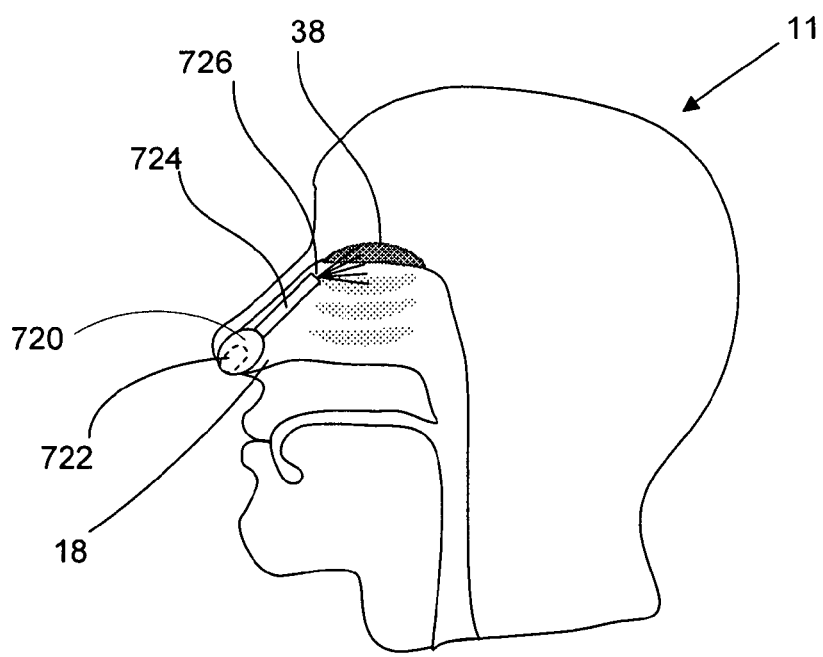
FIG. 31 is an illustration a delivery device including an extension.

In some embodiments, the system may include an extension connected to the structural element, wherein the structural element is mounted with a first portion of the nasal region of the subject, and wherein the extension extends from the structural element to a second portion of the nasal region to deliver the at least one material to the second portion of the nasal region. FIG. 31 illustrates an embodiment of a delivery device including a structural element 720 mounted in a nostril 18 of a person 11 by means of clip 722. Structural element 720 also includes extension 724 that project toward a more internal portion of the nasal region, which in this example is olfactory mucosa 38, where it releases material from end portion 726. End portion 726 may be the opening of a tubular structure connected to a material source in structural element 720, or end portion 726 may be a release location for a material source located at end portion 726. Other embodiments of delivery devices may include extensions configured to deliver material(s) to other portions of the nasal region, while the main part of the delivery device resides in a relatively accessible location, for example, the nostril.

Figure 32:
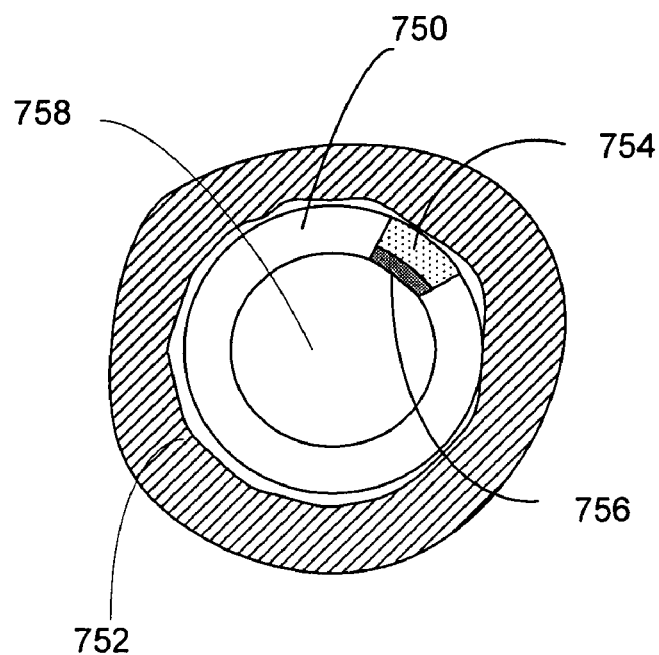
FIG. 32 is a cross-sectional view of an embodiment of a device including a stored deliverable material and a barrier release mechanism.

FIG. 32 illustrates, in cross sectional view, a structural element 750 of a delivery device positioned in a lumen-containing structure 752. A reservoir 754 contains stored deliverable material. Barrier 756 is a controllable barrier that controls the release of the stored deliverable material into central opening 758, and thus into a fluid that fills and/or flows through lumen-containing structure 752. Various types of barriers may be used to control the release of material from the delivery portion of the controllable release nasal system. For example, the delivery portion may include a rupturable barrier, a barrier having a controllable permeability, a stimulus-responsive gel or polymer, or a pressurized fluid source.

Figure 33:
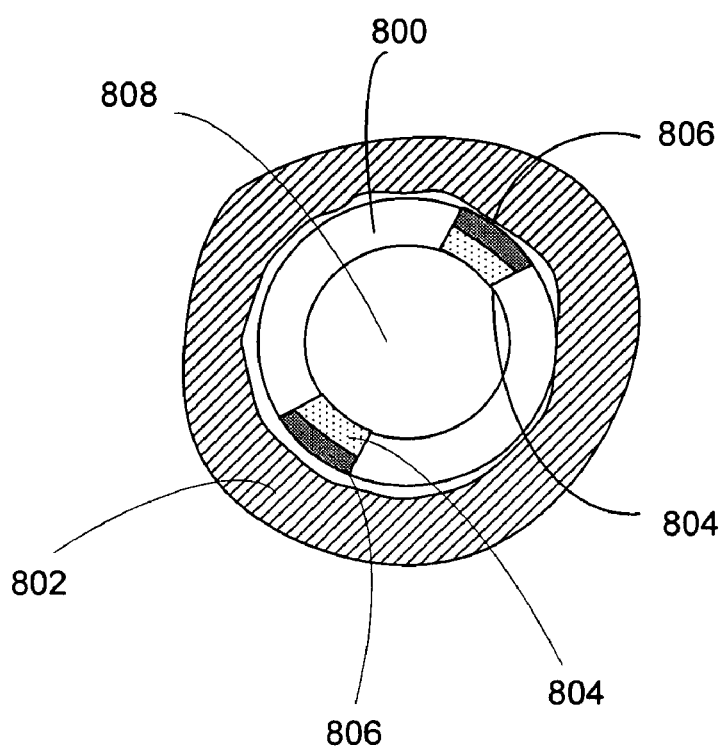
FIG. 33 is a cross-sectional view of another embodiment of a device including a stored deliverable material and a barrier release mechanism.

FIG. 33 illustrates an embodiment including a structural element 800 of a delivery device positioned in a lumen-containing structure 802. Two reservoirs 804 contain stored deliverable material(s). Each reservoir 804 includes a controllable barrier 806 that controls release of the at least one stored deliverable material. In the embodiment of FIG. 33, activation of barrier 806 causes release of the at least one stored deliverable material toward the lumen wall of lumen-containing structure 802, rather than into central opening 808. FIG. 33 also illustrates that delivery devices may include more than one reservoir.

FIGS. 34A, 34B, 35A, 35B, 36A and 36B, illustrate several alternative embodiments of material release structures that include controllable barriers. In FIGS. 34A and 34B, release structure 850 includes reservoir 852 containing stored deliverable material 854. As shown in FIG. 34A, while rupturable barrier 856 is intact, stored deliverable material 854 is contained within reservoir 852. As shown in FIG. 34B, when rupturable barrier 856 has been ruptured (as indicated by reference number 856'), deliverable material 854 may be released from reservoir 852. Rupturable barrier 856 may be ruptured by an increase of pressure in reservoir 852 caused by heating, for example, which may be controlled by response initiation circuitry. In another alternative shown in FIGS. 35A and 35B, release structure 900 includes reservoir 902 containing stored deliverable material 904. As shown in FIG. 35A, while degradable barrier 906 is intact, stored deliverable material 904 is contained within reservoir 902. As shown in FIG. 35B, degradation of degradable barrier 906 to degraded form 906' causes stored deliverable material 904 to be released from reservoir 902. FIGS. 36A and 36B depict release structure 950 including reservoir 952 containing stored deliverable material 954. FIG. 36A, shows barrier 956, which has a controllable permeability, in a first, impermeable state, while FIG. 36B shows barrier 956 in a second, permeable state (indicated by reference number 956'). Stored deliverable material 954 passes through barrier 956', when it is in its permeable state, and is released. Rupturable barriers as described above may be formed from a variety of materials, including, but not limited to, metals, polymers, crystalline materials, glasses, ceramics, semiconductors, etc. Release of materials through rupture or degradation of a barrier is also described in U.S. Pat. No. 6,773,429, which is incorporated herein by reference. Semipermable barriers having variable permeability are described, for example, in U.S. Pat. No. 6,669,683, which is incorporated herein by reference. Those of skill in the art will appreciate that barriers can be formed and operated reversibly through multiple release cycles, in addition to the single-release functionality available from a rupturable barrier.

Figure 37A:
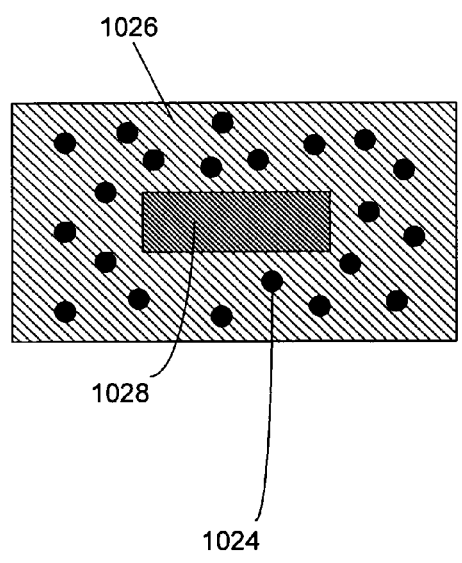
FIGS. 37A and 37B are depictions of the release of a stored deliverable material from a carrier material.
Figure 37B:
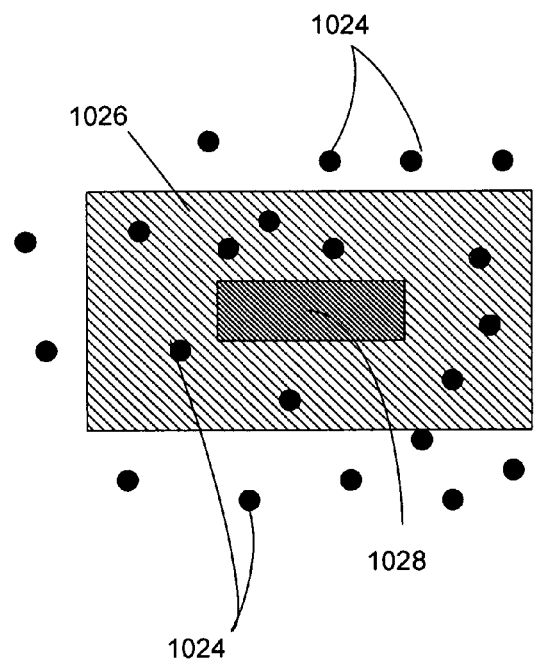

In some embodiments, a delivery device may include one or more stored deliverable materials dispersed in a carrier material. Stored deliverable material may be released from the carrier material by a release mechanism upon activation of the release mechanism. The released deliverable material may be released into a central opening of a delivery device and/or into the body lumen. FIGS. 37A and 37B depict in greater detail the release of stored deliverable material from the carrier material. In FIG. 37A, deliverable material 1024 is stored in carrier material 1026. Carrier material 1026 may be, for example, a polymeric material such as a hydrogel, and deliverable material is dispersed or dissolved within carrier material 1026. Release mechanism 1028 may be a heating element, for example a resistive element connected directly to response initiation circuitry, or an electrically or magnetically responsive material that may be caused to move, vibrate, heat, by an externally applied electromagnetic field, which in turn causes release of deliverable material 1024 from carrier material 1026, as shown in FIG. 29B. See, for example, U.S. Pat. Nos. 5,019,372 and 5,830,207, which are incorporated herein by reference. In some embodiments, an electrically or magnetically active component may be heatable by an electromagnetic control signal, and heating of the electrically or magnetically active component may cause the polymer to undergo a change in configuration. An example of a magnetically responsive polymer is described, for example, in Neto, et al, "Optical, Magnetic and Dielectric Properties of Non-Liquid Crystalline Elastomers Doped with Magnetic Colloids"; Brazilian Journal of Physics; bearing a date of March 2005; pp. 184-189; Volume 35, Number 1, which is incorporated herein by reference. Other exemplary materials and structures are described in Agarwal et al., "Magnetically-driven temperature-controlled microfluidic actuators"; pp. 1-5; located at: http://www.unl.im.dendai.acjp/INSS2004/INSS2004_papers/OralPresentations/C2.p df or U.S. Pat. No. 6,607,553, each of which is incorporated herein by reference. Other examples of stimulus-responsive gels or polymers are substance-responsive gels or polymers that swell, change shape, etc. in response to a change in pH, glucose, or other substance (as selected by embedded antibodies, for example). Examples of stimulus responsive gels or polymers are described in Langer, R. & Peppas, N., "Advances in Biomaterials, Drug Delivery, and Bionanotechnology," AIChE Journal, December 2003, Vol. 49, No. 12, pp. 2990-3006, which is incorporated herein by reference.

The controllable release nasal system may include a source of the material located in or on the structural element, as depicted generally in FIGS. 30-36B (e.g., either as a reservoir containing the material as shown in FIGS. 34A-36B, or as a portion of carrier material containing a dispersed or dissolved material, as shown in FIGS. 37A and 37B. Alternatively, a controllable release nasal system may include a source of material located external to the nasal region of the subject and connected to the delivery portion via a delivery tube that enters the nasal region of the subject via a nostril of the subject, as shown in FIG. 38

Figure 38:
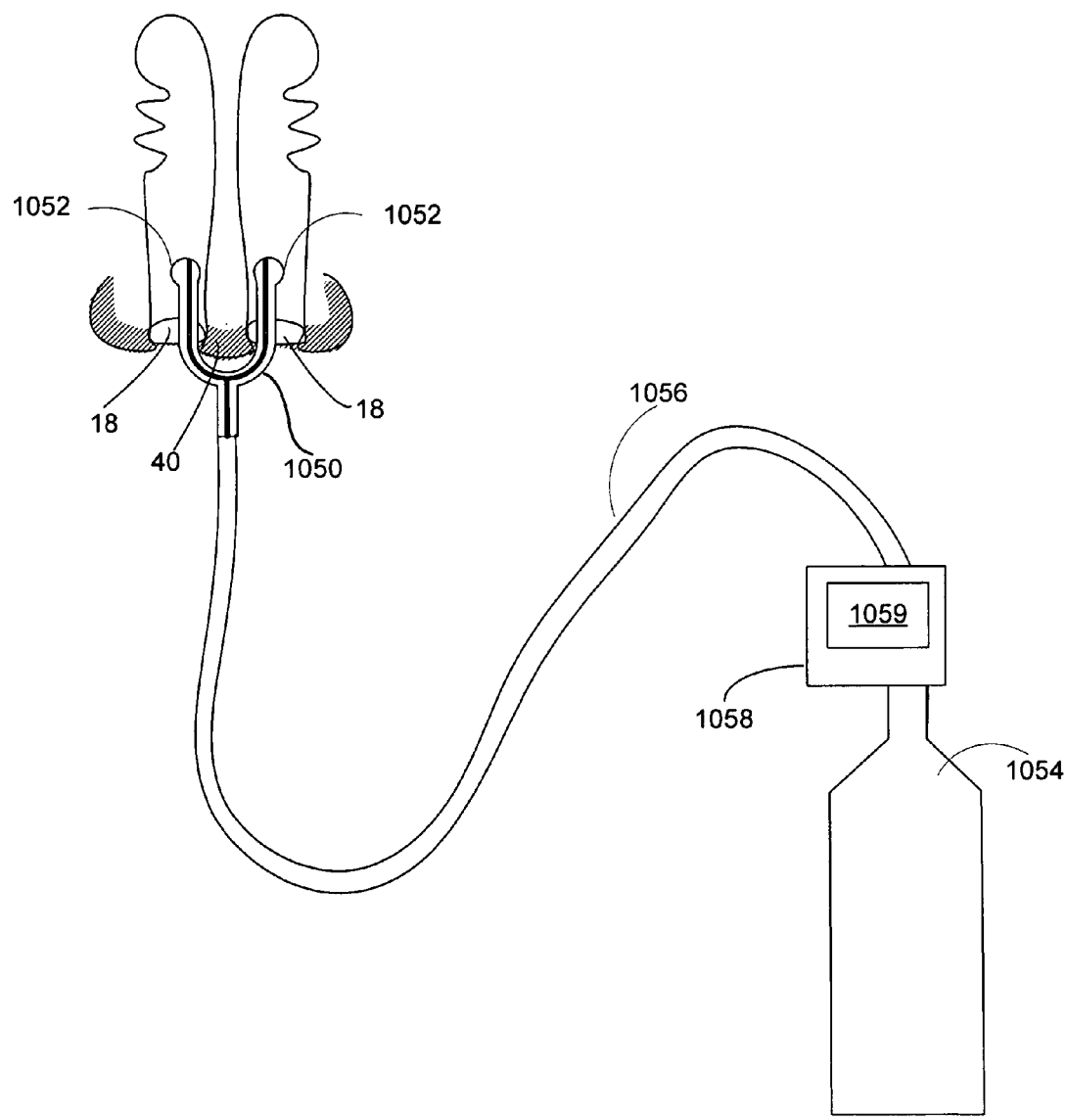
FIG. 38 is an illustration of an embodiment of a controllable release nasal system including an external material source.

In FIG. 38, structural element 1050 includes a clip-like structure that fits onto nasal septum 40, with end regions 1052 projecting into at least one nostril 18, which end-regions may include at-least-one sensor (not shown). Material to be delivered may be supplied from supply reservoir 1054 via supply tube 1056. A control device 1058 including control signal generation circuitry 1059 may control the flow of material (e.g., a gas or gaseous mixture, possibly carrying fluid droplets or fine solid particles) from supply reservoir 1054 to supply tube 1056 and thence into nostrils 18. Supply reservoir 1054 may be a tank capable of containing the material in liquid or gaseous form, or it may contain a solid source which releases material upon heating, change in pressure, or a chemical reaction, for example. In some embodiments, a carrier gas or liquid may be stored in supply reservoir 1054, and one or more active component of the material may be added from a secondary source that may be regulated by control device 1058, for example.

Figure 39:
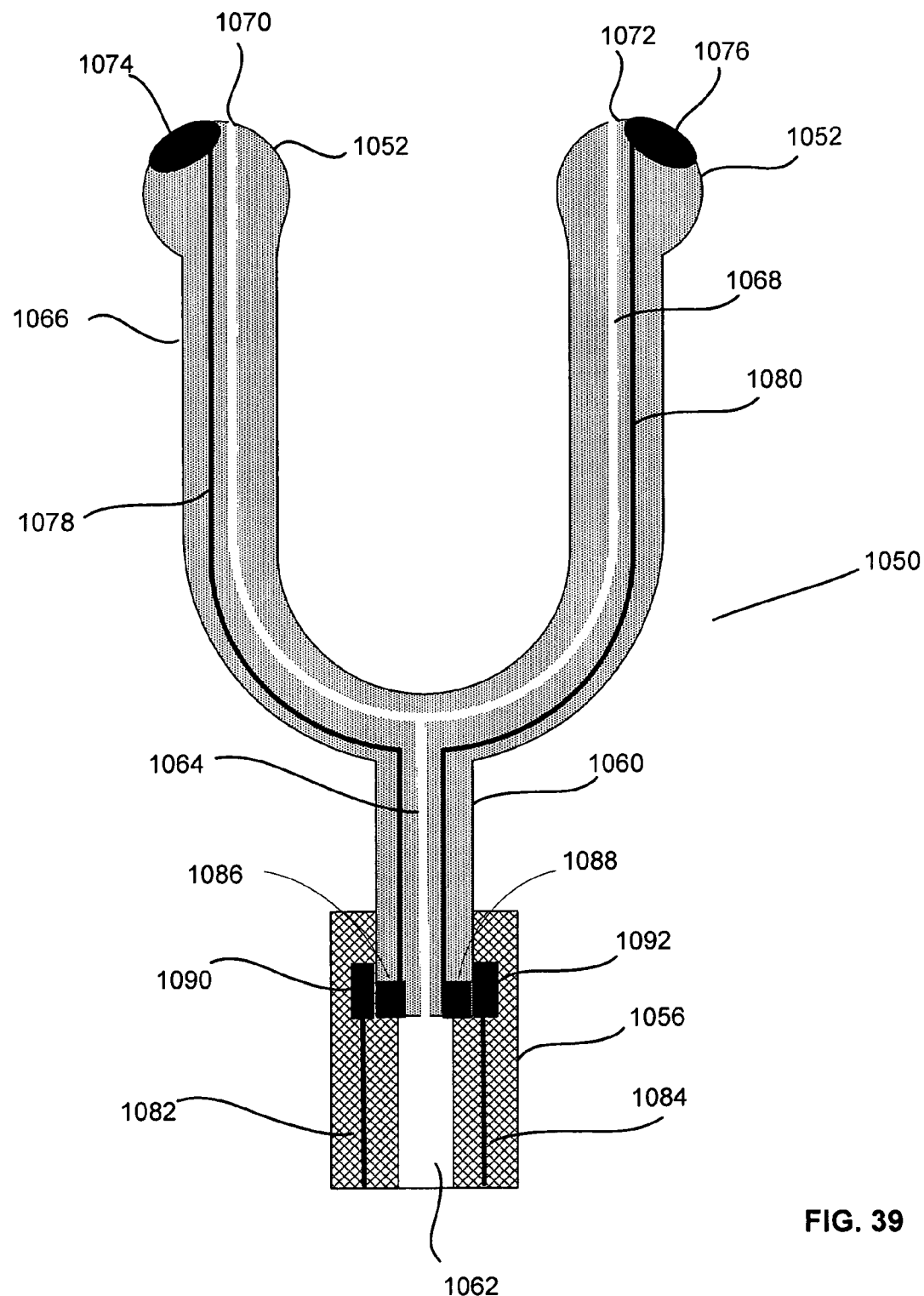
FIG. 39 is a close-up illustration of the nasal device portion of the system of FIG. 38.

FIG. 39 is a detailed cross-sectional view of structural element 1050 of the embodiment shown in FIG. 38. Supply tube 1056 fits over stem portion 1060 of structural element 1050. Channel 1062 in supply tube 1056 aligns with channel 1064 in structural element 1050. Channel 1064 connects to branch channels 1066 and 1068, which lead to openings 1070 and 1072, respectively. Material may be delivered to the one-or-both nostrils via openings 1070 and 1072. Structural element 1050 also includes sensors 1074 and 1076, which are connected to leads 1078 and 1080, respectively. Leads 1078 and 1080 are connected to leads 1082 and 1084, respectively in supply tube 1056 via contacts 1086 and 1088 in structural element 1050 and corresponding contacts 1090 and 1092 in supply tube 1056. Leads 1082 and 1084 connect sensors 1074 and 1076 to control signal generation circuitry (e.g., control signal generation circuitry 1059 as shown in FIG. 38), where they may serve to provide feedback signals which may be used in the determination of a delivery control signal for controlling the delivery of the material. Sensors 1074 and 1076 may be any of various types of sensors, as are known to those of skill in the art, for example, gas sensors, temperature sensors, flow sensors, pressure sensors, moisture sensors, strain sensors, acoustic sensors, chemical-composition or -concentration sensors, or other types of sensors as described elsewhere herein. Sensors 1074 and 1076 may be positioned on structural element 1050 in such a manner that they contact the nasal wall or septum, to sense a parameter of the nasal tissue, or they may be positioned on structural element 1050 in such a way that they sense a parameter from a fluid (gas and/or liquid) within the nostril or nasal cavity.

The delivery portion of the controllable release nasal device or system may deliver a material to a nasal region or a portion thereof by diffusion or low-speed dispersion of the material from the delivery portion (e.g., as depicted in FIG. 26) or it may deliver the material in a spray or jet, as depicted in FIGS. 27 through 29. In some embodiments, the system may rely upon fluid (air/liquid) movement or pressure changes associated with breathing activity to move or distribute the delivered material to the intended destination(s). FIG. 26 provides an example of an embodiment that relies upon diffusion or dispersion of the material into tissue. FIGS. 27 through 29 and 38 depict examples of embodiments in which the material may be delivered under pressure. For example, supply reservoir 1054 may be a pressurized tank. In other embodiments, the material may not be stored under pressure, but may have its pressure or speed-of-movement increased at the time of delivery by heating, for example.

Figure 40:
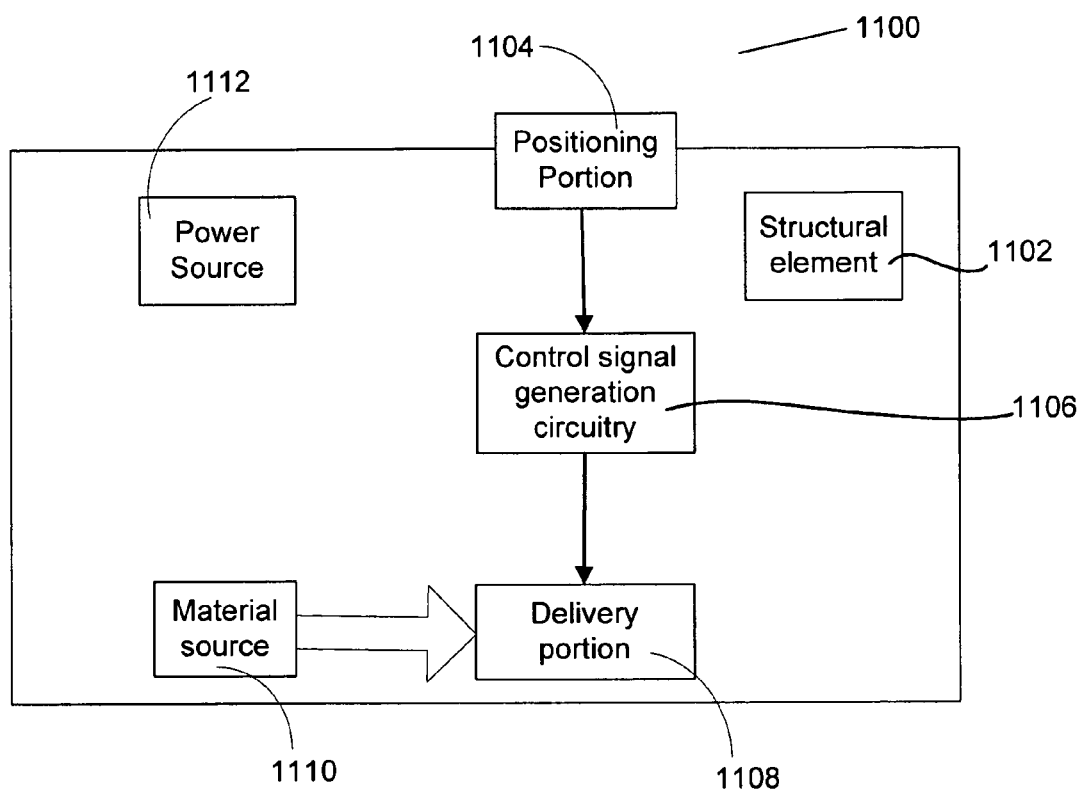
FIG. 40 is a block diagram of a controllable release nasal system.

FIG. 40 is a schematic diagram of a controllable release nasal system 1100 as described generally herein. Controllable release nasal system 1100 may include some or all of structural element 1102, positioning portion 1104, control signal generation circuitry 1106, delivery portion 1108, material source 1110, and power source 1112, as well as a sensing function (not shown explicitly).

Figure 41:
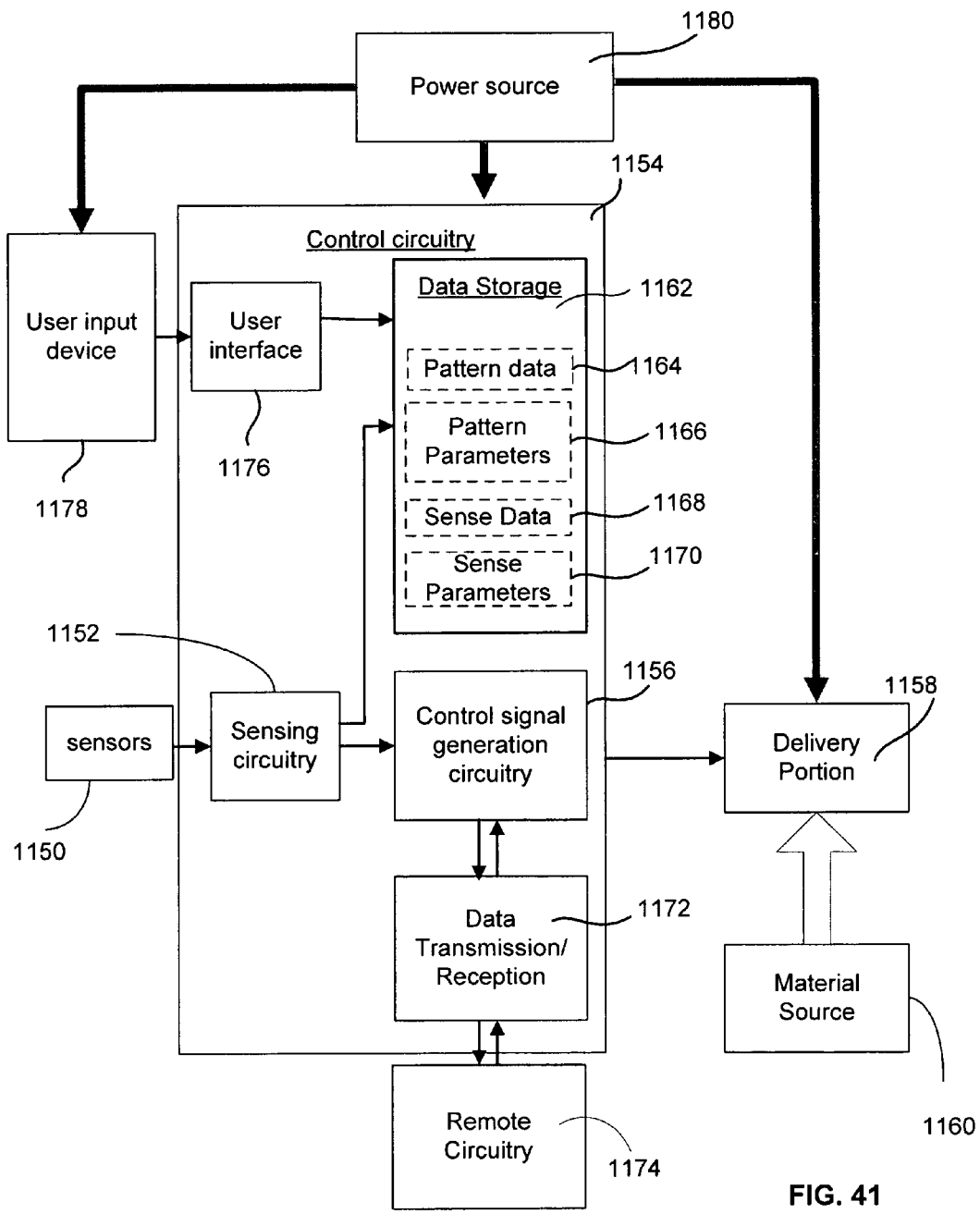
FIG. 41 is a schematic diagram illustrating components of control circuitry of a controllable release nasal system.

FIG. 41 is a block diagram illustrating in greater detail various circuitry components of a controllable release nasal system. Circuitry components may include electrical circuitry components, or, alternatively or in addition, fluid circuitry, optical circuitry, biological or chemical circuitry, chemo-mechanical circuitry, and/or other types of circuitry in which information is carried, transmitted, and/or manipulated by non-electronic means. The controllable release nasal system may include one or more sensors 1150 for measuring or detecting a condition of interest. Sensing circuitry 1152 may be associated with sensors 1150. The controllable release nasal system may include various control circuitry 1154, including control signal generation circuitry 1156. Control signal generation circuitry 1156 provides a delivery control signal to delivery portion 1158. Delivery portion may receive a material to be delivered from material source 1160. Control circuitry 1154 may also include data storage portion 1162, which may, for example, be used to store pattern data 1164 or pattern parameters 1166. Data storage portion 1162 may also be used to store sense data 1168 and/or sense parameters 1170, which may be derived from a sense signal, e.g. by sensing circuitry 1152. Control electronics may include data transmission/reception circuitry 1172, which provides for the transmission and reception of data and/or power signals between the delivery device and remote circuitry 1174. User interface circuitry 1176 may receive input signals from user input device 1178. User input device 1178 may provide for the input of user instruction, parameter, etc. to control circuitry 1154. Finally, one or more power sources 1180 may provide power to circuitry and other components of the controllable release nasal system.

The control signal generation circuitry, and control circuitry in general, may include a microprocessor and/or at least one of hardware, software, and firmware. The control signal generation circuitry may be configured to generate a delivery control signal based upon a pre-determined delivery pattern, in which case the system may also include a memory location for storing the pre-determined delivery pattern (e.g., pattern data 1164 stored in data storage portion 1162). In some embodiments, the control signal generation circuitry may be configured to calculate a delivery control signal based upon one or more stored parameters. Again, the system may include a memory location for storing the one or more parameters (e.g., pattern parameters 1166 or sense parameters 1170 stored in data storage portion 1162). For example, the control signal generation circuitry may be configured to generate a delivery control signal corresponding to a pattern of delivery of the at least one material expected to produce a therapeutic effect or a sensory effect. In some embodiments, the control signal generation circuitry may be configured to generate a delivery control signal corresponding to a pattern of delivery of the at least one material expected to produce a therapeutic effect tailored specifically to the subject. For example, the control signal generation circuitry may be configured to generate a delivery control signal taking into account parameters such as the size, weight, gender, age, as well as specifics relating to the subject's preferences, medical condition or other parameters.

Figure 42:
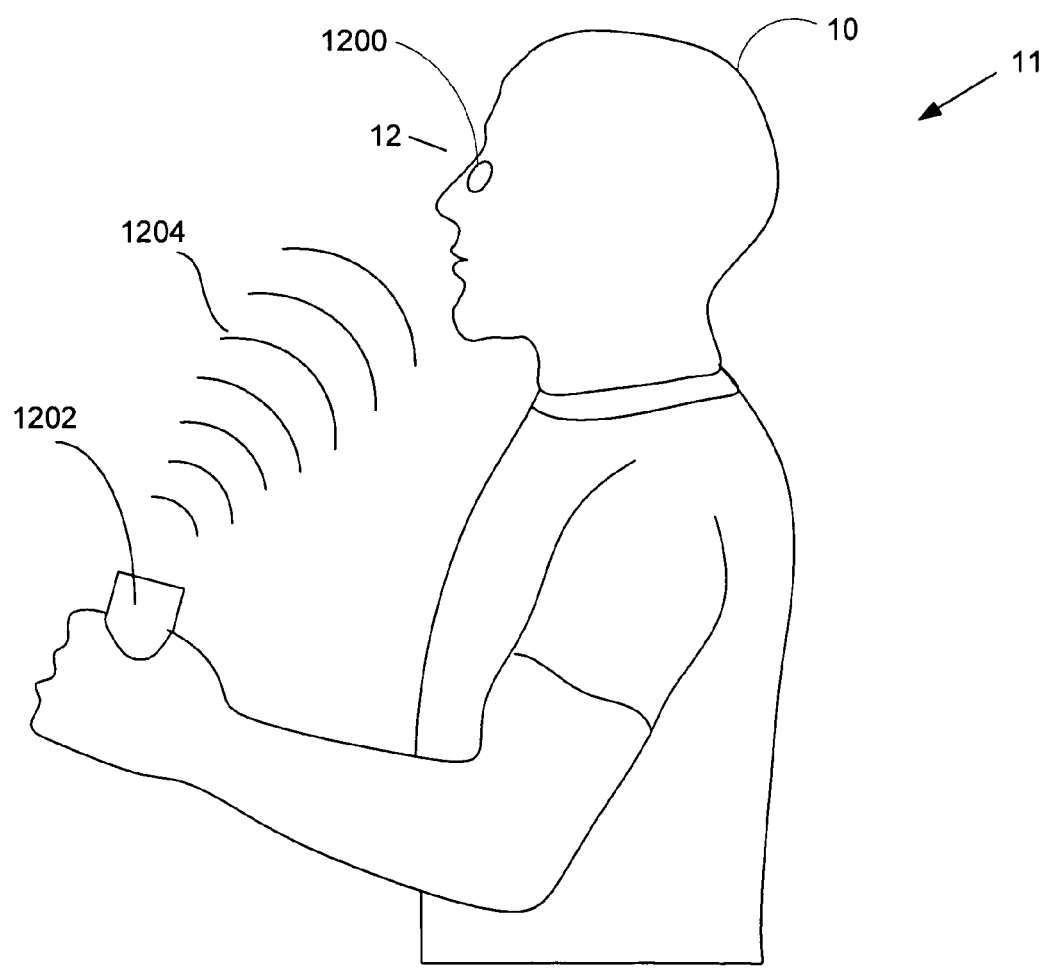
FIG. 42 is an illustration of a controllable release nasal system including an external control portion.

Circuitry components as discussed in connection with FIG. 41 may be located entirely on the structural element of a delivery device portion of a controllable release nasal system, or may be distributed between the delivery device and a remote portion as depicted in FIG. 42. In FIG. 42, a delivery device 1200 is positioned in nasal region 12 of head 10 of a person 11. Remote portion 1102 may be held by person 11, or otherwise positioned nearby person 11. For example, remote portion 1202 may be carried or attached to a wristband or necklace. Remote portion 1102 may transmit signal 1204 to delivery device 1200. Signal 1204 may be a one- or two-way signal, containing control, data, or power signals. In some embodiments, remote portion 1202 may permit person 11 to provide user input to specify delivery of material to nasal region 12 with delivery device 1200.

Figure 43:
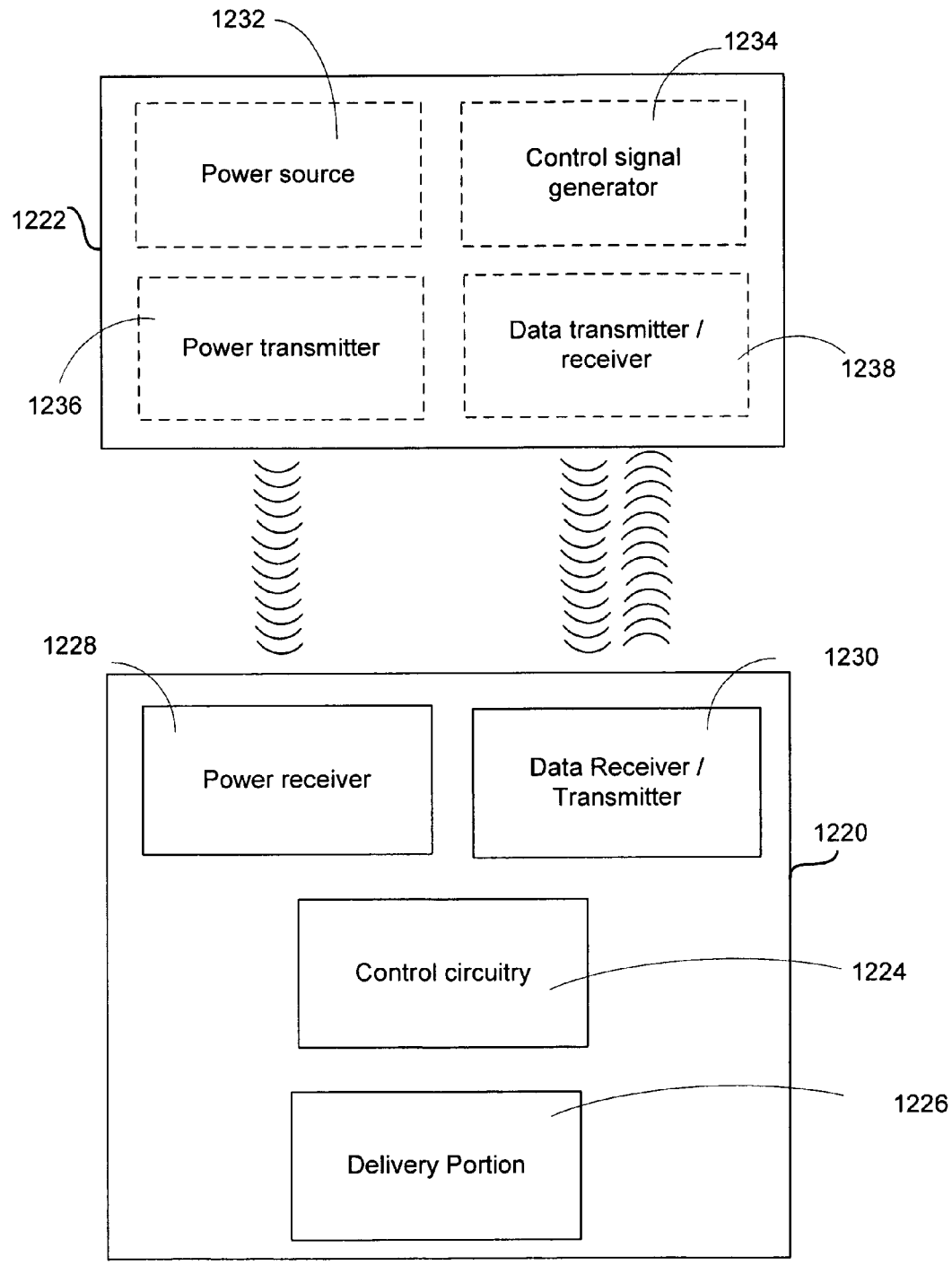
FIG. 43 is a block diagram of a controllable release nasal system including an external control portion.

Alternatively, in some embodiments, control signal generation circuitry may be located remote from the structural element and associated with a transmitting structure capable of transmitting the delivery control signal to the structural element, and wherein the delivery portion is associated with a receiving structure capable of receiving the delivery control signal. FIG. 43 is a block diagram of a controllable release nasal system including a delivery device 1220 and remote portion 1222. Delivery device 1220 may include various components as depicted in FIG. 41, including (but not limited to) control circuitry 1224, delivery portion 1226, and one or both of a power receiver 1228 and data receiver/transmitter 1230. In some embodiments, data receiver/transmitter 1230 may only receive data signals, while in other embodiments it may only transmit data signals, and in still other embodiments it may both transmit and receive data signals. Power receiver 1228 may receive power signals transmitted from remote portion 1222. Remote portion 1222 may include one or both of power source 1232 and control signal generator 1234. Power transmitter 1236 may be used in connection with power source 1232 in order to transmit power to power receiver 1228 in delivery device 1220. Data transmitter/receiver 1238 may transmit a delivery control signal from control signal generator 1234 to delivery device 1220, or receive sense or parameter data signals transmitted from delivery device 1220 by data receiver/transmitter 1230. In some embodiments of the system, the control signal generation circuitry may be a part of the delivery device, located in or on the structural element.

In some embodiments of delivery devices or systems, a delivery device may be a self-contained device that may be positioned in a body lumen and that includes all functionalities necessary for operation of the device. In other embodiments, as shown in FIGS. 42 and 43, a controllable release nasal system may include a delivery device that may be placed in a nasal region, and a remote portion that includes a portion of the functionalities of the controllable release nasal system. In some embodiments, all functionalities essential for the operation of the delivery device may be located on the delivery device, but certain auxiliary functions may be located in the remote portion. For example, the remote portion may provide for monitoring of the operation of the delivery device or data collection or analysis. The remote portion may be located within the body of the subject at a distance from the delivery device, or outside the body of the subject, as depicted in FIG. 42, either proximate to or distant from it. Data and/or power signals may be transmitted between delivery device and remote portion with the use of electromagnetic or acoustic signals, or, in some embodiments, may be carried over electrical or optical links. In general, the remote portion may be placed in a location where there is more space available than within the body lumen, that is more readily accessible, and so forth. It is contemplated that a portion of the circuitry portion of the controllable release nasal system (which may include hardware, firmware, software, or any combination thereof) may be located in a remote portion. Methods of distributing functionalities of a system between hardware, firmware, and software located at two or more sites are well known to those of skill in the art. The control circuitry portion of the controllable release nasal system may include, but is not limited to, electrical circuitry associated with the sensor, response initiation circuitry, and electronics associated with the active portion.

In various embodiments, the system may include a power source such as a battery. A power source may also be considered to include a power receiver capable of receiving inductively coupled power from an external power source, e.g., as depicted in FIG. 43. Delivery devices and systems according to various embodiments as described herein may include a power source, such as one or more batteries located on the delivery device, possibly a microbattery like those available from Quallion LLC (http://www.quallion.com) or designed as a film (U.S. Pat. Nos. 5,338,625 and 5,705,293), which are incorporated herein by reference. Batteries may include primary or secondary batteries, including various types of electrochemical energy storage devices. In some embodiments, the power source may be one or more fuel cell such as an enzymatic, microbial, or photosynthetic fuel cell or other biofuel cell (US20030152823A1; WO03106966A2, and "A Miniature Biofuel cell"; Chen, T. et al., J. Am. Chem. Soc., Vol. 123, pp. 8630-8631, 2001, all of which are incorporated herein by reference), and could be of any size, including the micro- or nano-scale. In some embodiments, the power source may be a nuclear battery. The power source may be any of various mechanical energy storage devices, including but not limited to pressurized bladders or reservoirs, wind-up and spring-loaded devices. The power source may be an energy-scavenging device such as a pressure-rectifying mechanism that utilizes pulsatile changes in blood pressure, for example, or an acceleration-rectifying mechanism as used in self-winding watches; it may derive energy from the cyclic flow of gas through the upper airway. In some embodiments, the power source may be an electrical power source located remote from the structural element and connected to the structural element by a wire, or an optical power source located remote from the structural element and connected to the structural element by a fiber-optic line or cable. In some embodiments, the power source may be a power receiver capable of receiving power from an external source, acoustic energy from an external source, a power receiver capable of receiving electromagnetic energy (e.g., microwave, infrared or optical electromagnetic energy) from an external source.

The control signal generation circuitry may include at least one of hardware, software, and firmware; in some embodiments the control signal generation circuitry may include a microprocessor or a (programmable) logic array. The control signal generation circuitry may be located in or on the structural element in some embodiments, while in other embodiments the response initiation circuitry may be at a location remote from the structural element.

Figure 44:
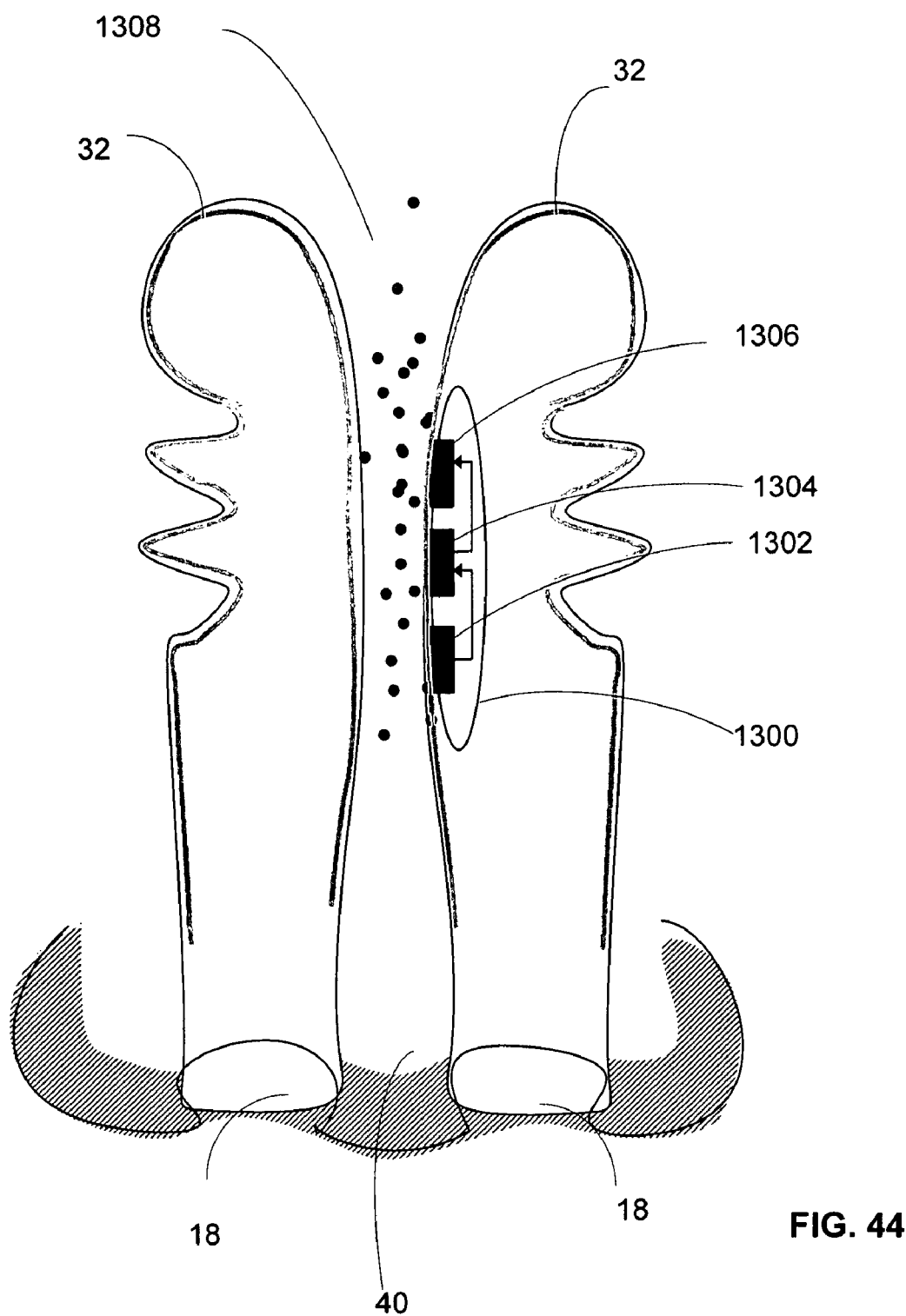
FIG. 44 is a front cross-sectional view of an embodiment of a controllable release nasal device.

FIG. 44 depicts a controllable release nasal device 1300 including a sensor 1302 capable of detecting a parameter of interest in the nasal region of the subject. Controllable release nasal device 1300, may include sensor 1302, control signal generation circuitry 1304, and delivery portion 1306. The control signal generation circuitry may be configured to modulate generation of the delivery control signal based upon at least one parameter of interest sensed by the sensor. Controllable release nasal device may be positioned on nasal septum 40, with delivery portion 1306 located against the nasal mucosa 32. Sensor 1302 may sense a parameter from the tissue (for example, a chemical parameter such as a glucose concentration, a heart rate or blood pressure parameter, or a temperature, among others). Control signal generation circuitry 1304 may generate a delivery control signal based upon a sense signal received from sensor 1302. The delivery control signal may be provided to delivery portion 1306, to drive delivery of material 1308.

Figure 45:
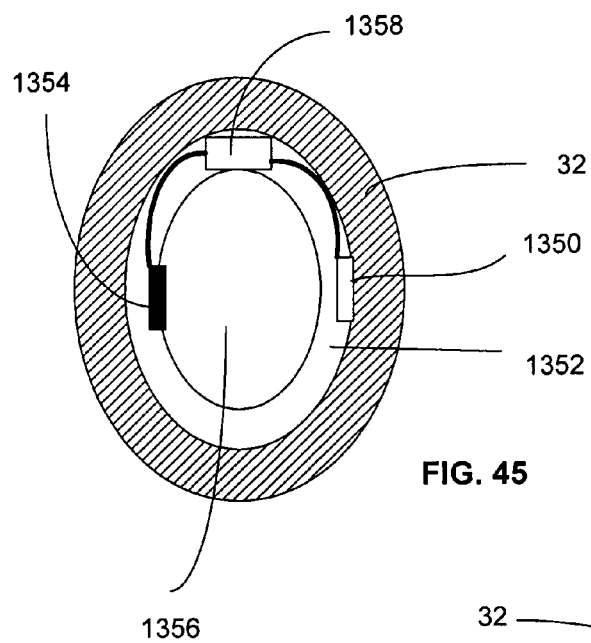
FIG. 45 is an illustration of an embodiment of controllable release nasal device including a delivery portion and a sensor.
Figure 46:
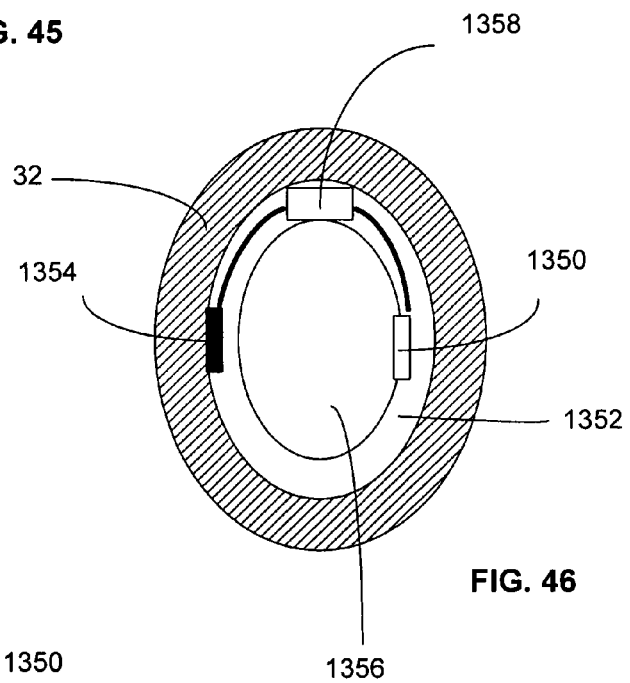
FIG. 46 is an illustration of another embodiment of controllable release nasal device including a delivery portion and a sensor.
Figure 47:
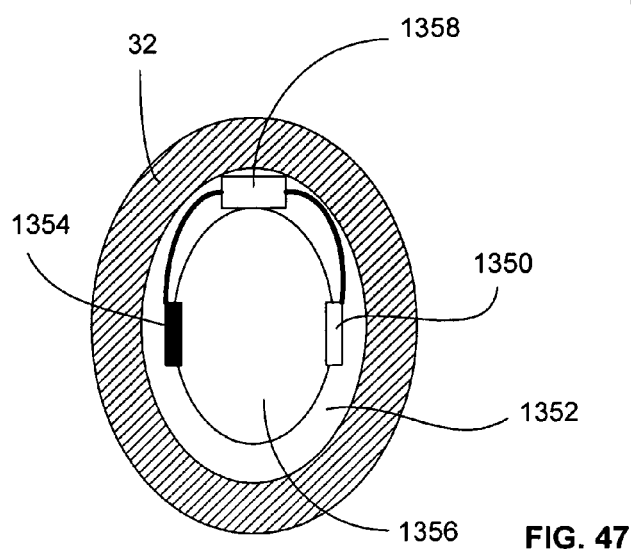
FIG. 47 is an illustration of another embodiment of controllable release nasal device including a delivery portion and a sensor.

In the controllable release nasal device depicted in FIG. 44, both sensor 1302 and delivery portion 1306 are positioned adjacent to nasal mucosa 32. FIGS. 45, 46 and 47 depict other possible configurations for sensors and delivery portions of controllable release nasal devices. FIGS. 45 through 47 are cross-sectional views of a controllable release nasal device in a nostril. In FIG. 45, sensor 1350 is positioned on structural element 1352 so as to be positioned adjacent to the nasal mucosa 32 when structural element 1352 is mounted within the nasal region of the subject. Delivery portion 1354 is positioned adjacent lumen 1356 of structural element 1352, away from nasal mucosa 32. Control signal generation circuitry 1358 is also indicated. Alternatively, as shown in FIG. 46, sensor 1350 may be positioned on structural element 1352 so as to be positioned adjacent to lumen 1356 when structural element 1352 is mounted within the nasal region of the subject. In still other embodiments, as illustrated in FIG. 47, both sensor 1350 and delivery portion 1354 may be positioned adjacent to lumen 1356 when structural element 1352 is mounted within the nasal region of the subject.

Sensors used in the various embodiments described herein (e.g., sensors 1074 and 1076 in FIG. 39, sensor 1302 in FIG. 44, or sensor 1350 in FIGS. 45-47) may be of various types, including, for example pressure sensors, temperature sensors, flow sensors, or chemical sensors, for example. Sensors may be used to detect a condition of interest in the fluid (e.g. gas and/or liquid droplets or small solid particles) within a lumen of the nasal cavity (or lumen of a delivery device continuous therewith), or in tissue surrounding the lumen, which may include, for example, detecting pressure, temperature, fluid flow, presence of a cell of interest, or concentration of a chemical or chemical species (including ionic species) of interest. A sensor may sense a wide variety of physical or chemical properties. In some embodiments, detecting a condition of interest may include detecting the presence (or absence) of a material or structure of interest in the fluid. A sensor may include one or more of an optical sensor, an imaging device, an acoustic sensor, a pressure sensor, a temperature sensor, a flow sensor, a viscosity sensor, or a shear sensor for measuring the effective shear modulus of the fluid at a frequency or strain-rate, a chemical sensor for determining the concentration of a chemical compound or species, a biosensor, or an electrical sensor, for example. An optical sensor may be configured to measure the absorption, emission, fluorescence, or phosphorescence of at least a portion of the fluid, for example. Such optical properties may be inherent optical properties of all or a portion of the fluid, or may be optical properties of materials added or introduced to the fluid, such as tags or markers for materials of interest within the fluid. A biosensor may detect materials including, but not limited to, a biological marker, an antibody, an antigen, a peptide, a polypeptide, a protein, a complex, a nucleic acid, a cell or cell fragment (and, in some cases, a cell of a particular type, e.g. by methods used in flow cytometry), a cellular component, an organelle, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, a pollutant, or a tag. A biosensor may include an antibody or other reasonably specific binding molecule such as a receptor or ligand. A sensor may include a single sensor or an array of sensors, and is not limited to a particular number or type of sensors. A sensor might comprise in part or whole, a gas sensor such as an acoustic wave, chemiresistant, or piezoelectric sensor, or perhaps an "electronic nose". A sensor may be very small, comprising a sensor or array that is a chemical sensor ("Chemical Detection with a Single-Walled Carbon Nanotube Capacitor", E. S. Snow, Science, Vol. 307, pp. 1942-1945, 2005), a gas sensor ("Smart single-chip gas sensor microsystem", Hagleitner, C. et al., Nature, Vol. 414 pp. 293-296, 2001), an electronic nose, a nuclear magnetic resonance imager ("Controlled multiple quantum coherences of nuclear spins in a nanometre-scale device", Go Yusa, Nature, Vol. 343: pp. 1001-1005, 2005). Further examples of sensors are provided in The Biomedical Engineering Handbook, Second Edition, Volume I, J. D. Bronzino, Ed., Copyright 2000, CRC Press LLC, pp. V-1-51-9, and U.S. Pat. No. 6,802,811, both of which are incorporated herein by reference. A sensor may be configured to measure various parameters, including, but not limited to, the electrical resistivity of the fluid, the density or sound speed of the fluid, the pH, the osmolality, or the index of refraction of the fluid at least one wavelength, as well as its temperature, water content and chemical composition. The selection of a suitable sensor for a particular application or use site is considered to be within the capability of a person having skill in the art. In some applications, detecting a condition of interest in the fluid may include detecting the presence of a material of interest in the fluid (gas and/or liquid) within a nasal lumen. A material of interest in a fluid may include, dust particle, a pollen particle, a pathogen, or parasite, or a cell, cellular component, or collection or aggregation of cells or components thereof.

A controllable release nasal device may include an active portion which may perform an action in the nasal cavity in addition to or instead of the material release function performed by the release portion described herein. A release portion is an exemplar of an active portion. A number of active portions are described, for example, in U.S. patent application Ser. No. 11/403,230, entitled "Lumenally Active Device" and filed Apr. 12, 2006, which is incorporated herein by reference above.

In connection with detection of the presence of a material of interest, for example, an active portion of the controllable release nasal system may be capable of removing, modifying, or destroying the material of interest. Modification or destruction of the material of interest may be accomplished by the release of a suitable material (e.g. an endopeptidase for killing bacteria, or an anti-inflammatory, biomimetic, or biologic to bind to and inactivate an inflammatory mediator such as histamine or an immunoglobulin), by the delivery of suitable energy (e.g., acoustic energy, electromagnetic energy such as light to cause a photoreaction, break bonds in a molecule, produce heating, etc., or by delivery of heat or cold or other chemo-physical change (e.g. ambient pressure, pH, osmolality, toxic material introduction/generation) for tissue modification or ablation.

Figure 48:
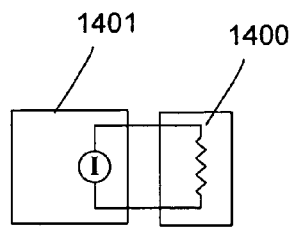
FIG. 48 depicts an embodiment of an active portion including a heating element.

FIGS. 48 through 55 illustrate examples of different active portions which may be included in a controllable release nasal device or system. The active portion may include a heating element 1400 as depicted in FIG. 48, operatively coupled to the response initiation circuitry 1401 and configured to produce heating in response to detection of the condition of interest. The heating element may be a resistive element that produces heat when current is passed through it, or it may be a magnetically active material that produces heat upon exposure to an electromagnetic field. Examples of magnetically active materials include permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as silicate or sulfide, and antiferromagnetic materials such as canted antiferromagnetic materials which behave similarly to ferromagnetic materials; examples of electrically active materials include ferroelectrics, piezoelectrics and dielectrics.

Figure 49:
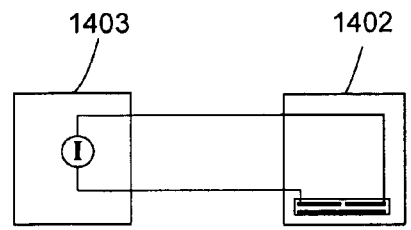
FIG. 49 depicts an embodiment of an active portion including a cooling element.

Alternatively, the active portion may include a cooling element 1402 as depicted in FIG. 49, operatively coupled to the response initiation circuitry 1403 and configured to produce cooling in response to detection of the condition of interest. Cooling may be produced by a number of mechanisms and/or structures. For example, cooling may be produced by an endothermic reaction (such as the mixing of ammonium nitrate and water) initiated by opening of a valve or actuation of a container in response to a control signal. Other methods and/or mechanisms of producing cooling may include, but are not limited to, thermoelectric (e.g., Peltier Effect) and liquid-gas-vaporization (e.g., Joule-Thomson) devices.

Figure 50:
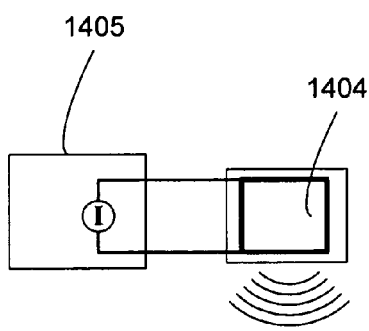
FIG. 50 depicts an embodiment of an active portion including an electromagnetic radiation source.

In some embodiments, the active portion may include an electromagnetic radiation source 1404 as depicted in FIG. 50, operatively coupled to the response initiation circuitry 1405 and configured to emit electromagnetic radiation in response to detection of the condition of interest. Electromagnetic radiation sources may include light sources, for example, such as light emitting diodes and laser diodes, or sources of other frequencies of electromagnetic energy or radiation, radio waves, microwaves, ultraviolet energy, infrared energy, optical energy, terahertz radiation, and the like. In some embodiments, the active portion may include an electric field source or a magnetic field source.

Figure 51:
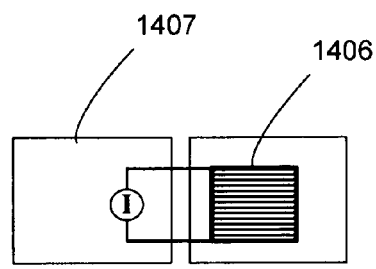
FIG. 51 depicts an embodiment of an active portion including an acoustic signal source.
Figure 52:
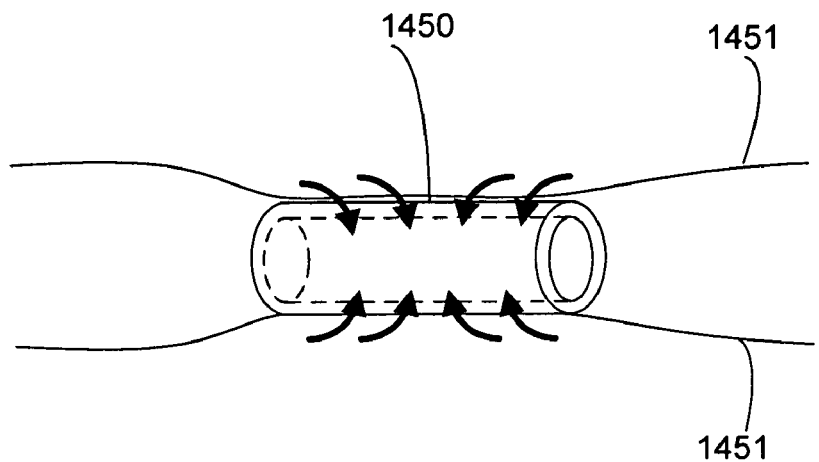
FIG. 52 depicts an embodiment of an active portion including a negative pressure source.
Figure 53:
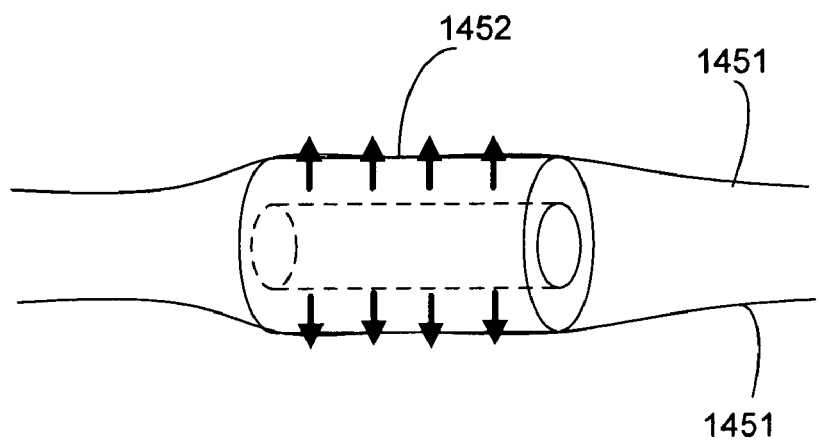
FIG. 53 depicts an embodiment of an active portion including a positive pressure source.

As another alternative, the active portion may include an acoustic energy source 1406 (e.g., a piezoelectric crystal) as depicted in FIG. 51, operatively coupled to the response initiation circuitry 1407 and configured to emit acoustic energy in response to detection of the condition of interest. The active portion may include a pressure source operatively coupled to the response initiation circuitry and configured to apply pressure to a portion of the body lumen in response to detection of the condition of interest. Pressure sources may include materials that expand through absorption of water, or expand or contract due to generation or consumption of gas or conformation change produced by chemical reactions or temperature changes, electrically-engendered Maxwell stresses, osmotic stress-generators, etc. FIG. 52 depicts a negative pressure source 1450 capable of applying negative pressure (in this example, substantially radially-inward force) to lumen walls 1451, while FIG. 53 depicts a positive pressure (expanding or expansion) source 1452, capable of applying positive pressure (in this example, a substantially radially-outward force) to lumen walls 1451.

Figure 54:
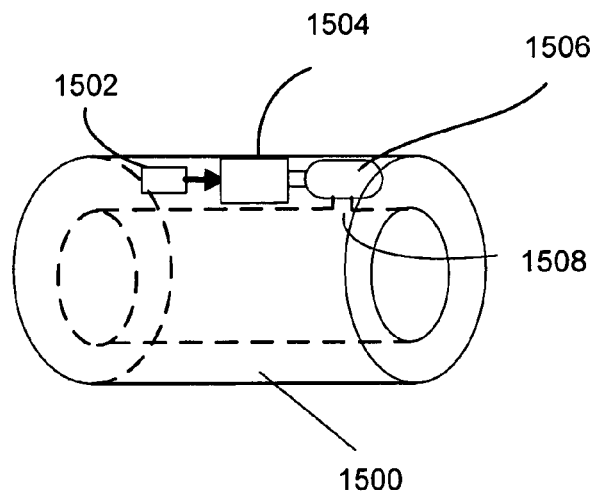
FIG. 54 is an illustration of another embodiment of a controllable release nasal device.

Alternatively, or in addition, in some embodiments the active portion may include a capture portion operatively coupled to the response initiation circuitry and configured to capture the detected material of interest. FIG. 54 depicts a device 1500 including a fluid capture portion 1506. Delivery device 1500 includes sensor 1502, response initiation circuitry 1504, and fluid capture portion 1506. Fluid enters fluid capture portion 1506 via inlet 1508. Fluid capture portion 1506 may be a reservoir, for example, into which fluid is drawn by capillary action. Alternatively, fluid may be pumped into capture portion 1506. Captured fluid may be treated and released, or simply stored. In some applications, stored fluid may be subjected to analysis.

Figure 55:
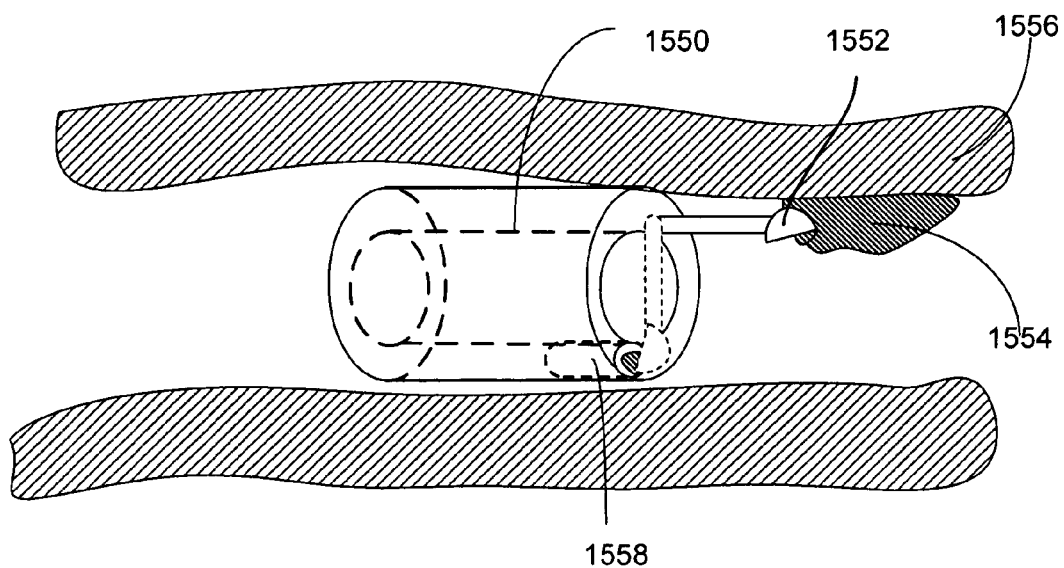
FIG. 55 is a depiction of an embodiment of a controllable release nasal device including a material collection structure.

FIG. 55 depicts delivery device 1550 including a sample collection structure 1552 capable of collecting a solid sample 1554. In the example depicted in FIG. 55, solid sample 1554 is a solid material found upon or immediately under the surface of the lumen-defining wall 1556 (a nasal polyp or inflamed tissue biopsy sample, for example). Solid sample 1554 placed in storage reservoir 1558 by sample collection structure 1552. In a related alternative embodiment, a delivery device may include a filter or selective binding region to remove materials from fluid moving past or through the delivery device.

Figure 56:
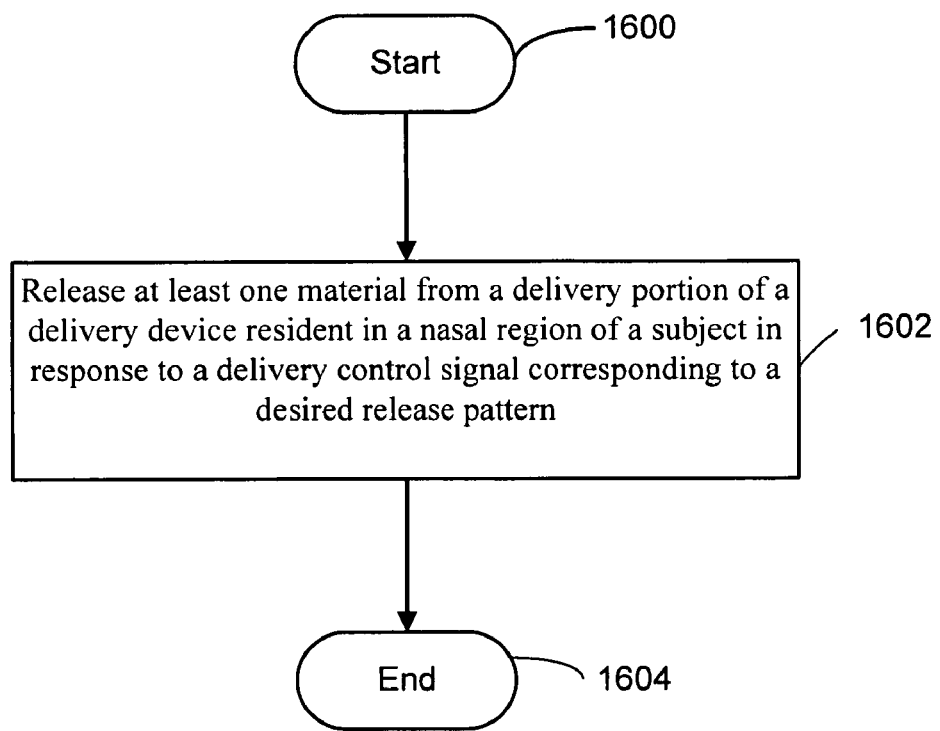
FIG. 56 is a flow diagram of a method of delivering a material to a nasal region of a subject.

FIG. 56 is a flow diagram of a method of delivering a material to the nasal region of a subject. As indicated at 1602, the method may include the step of releasing at least one material from a delivery portion of a delivery device mounted within a nasal region of a subject in response to a delivery control signal corresponding to a desired release pattern.

The method may include including transmitting information relating to the operation of the delivery device to a remote location, which may include, for example, information relating to the delivery of material by the delivery device. The method may include transmitting information relating to one or more sensed values of the parameter of interest to a remote location.

Figure 57:
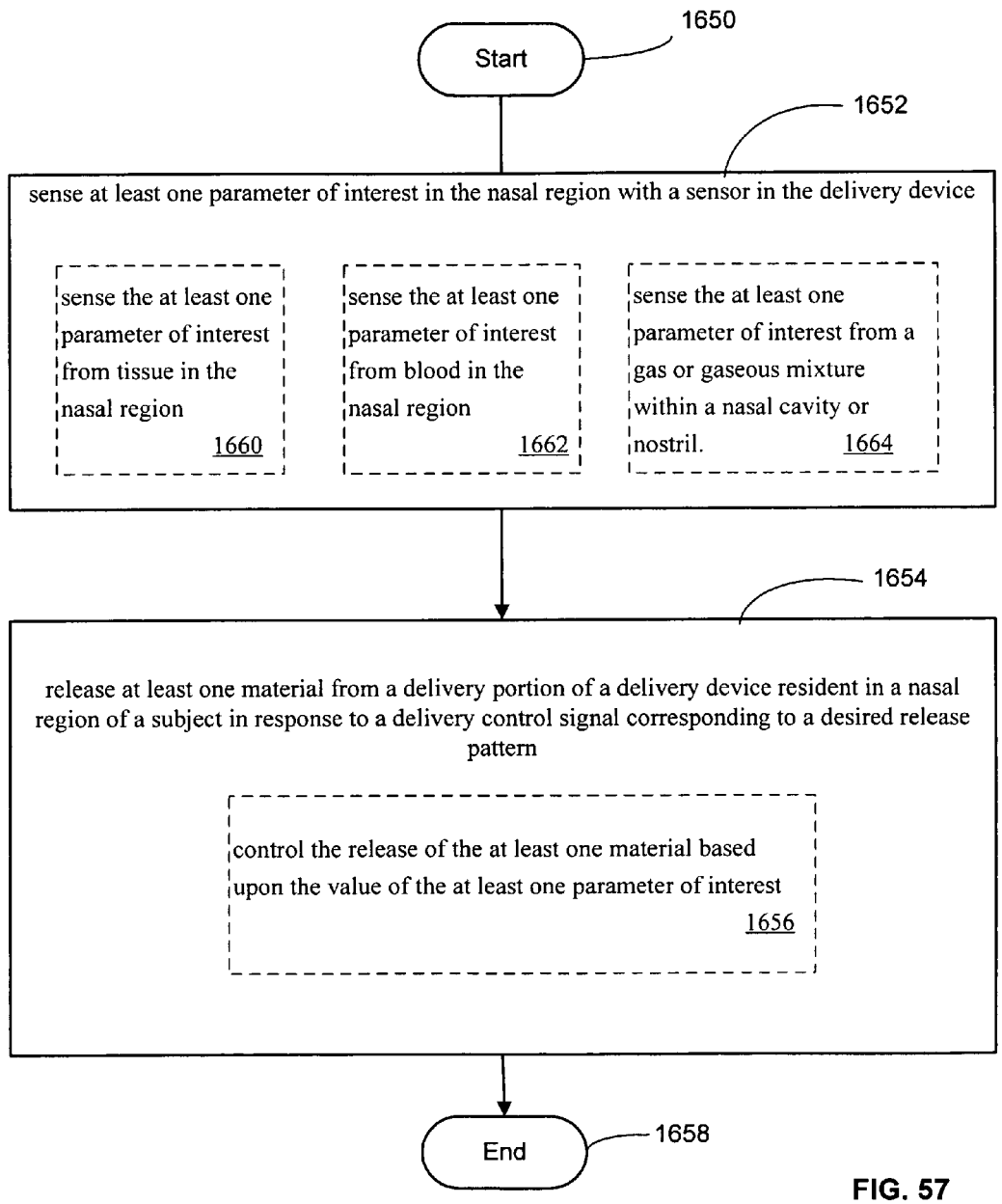
FIG. 57 is a flow diagram of a method of delivering a material to a nasal region of a subject.

As shown in FIG. 57, in addition to releasing at least one material from a delivery portion of a delivery device mounted within a nasal region of a subject in response to a delivery control signal corresponding to a desired release pattern at 1654, the method may include the additional steps of sensing at least one parameter of interest in the nasal region with a sensor in the delivery device at 1652, and controlling the release of the at least one material based upon the value of the at least one parameter of interest at 1656. The method may include sensing the at least one parameter of interest from tissue in the nasal region, as shown at 1660, sensing the at least one parameter of interest from blood in the nasal region, as shown at 1662, or sensing the at least one parameter of interest from a gas or gaseous mixture within a nasal cavity or nostril, as shown at 1664.

As shown in FIG. 58, other method steps may include a number of alternative method steps for generating a delivery control signal. As shown at step 1702, the method may include generating the delivery control signal with a control signal generation circuitry in a remote device and transmitting the delivery control signal to the delivery device. Alternatively, as shown at step 1704, the method may include generating the delivery control signal with control signal generation circuitry in the delivery device, or generating the delivery control signal with control signal generation circuitry located at least in part at a location remote from the delivery portion of the delivery device, shown at step 1706. Any of steps 1702 through 1706 may be followed by a step of releasing at least one material from a delivery portion of a delivery device mounted within a nasal region of a subject in response to a delivery control signal corresponding to a desired release pattern, as indicated at step 1708.

Figure 59:
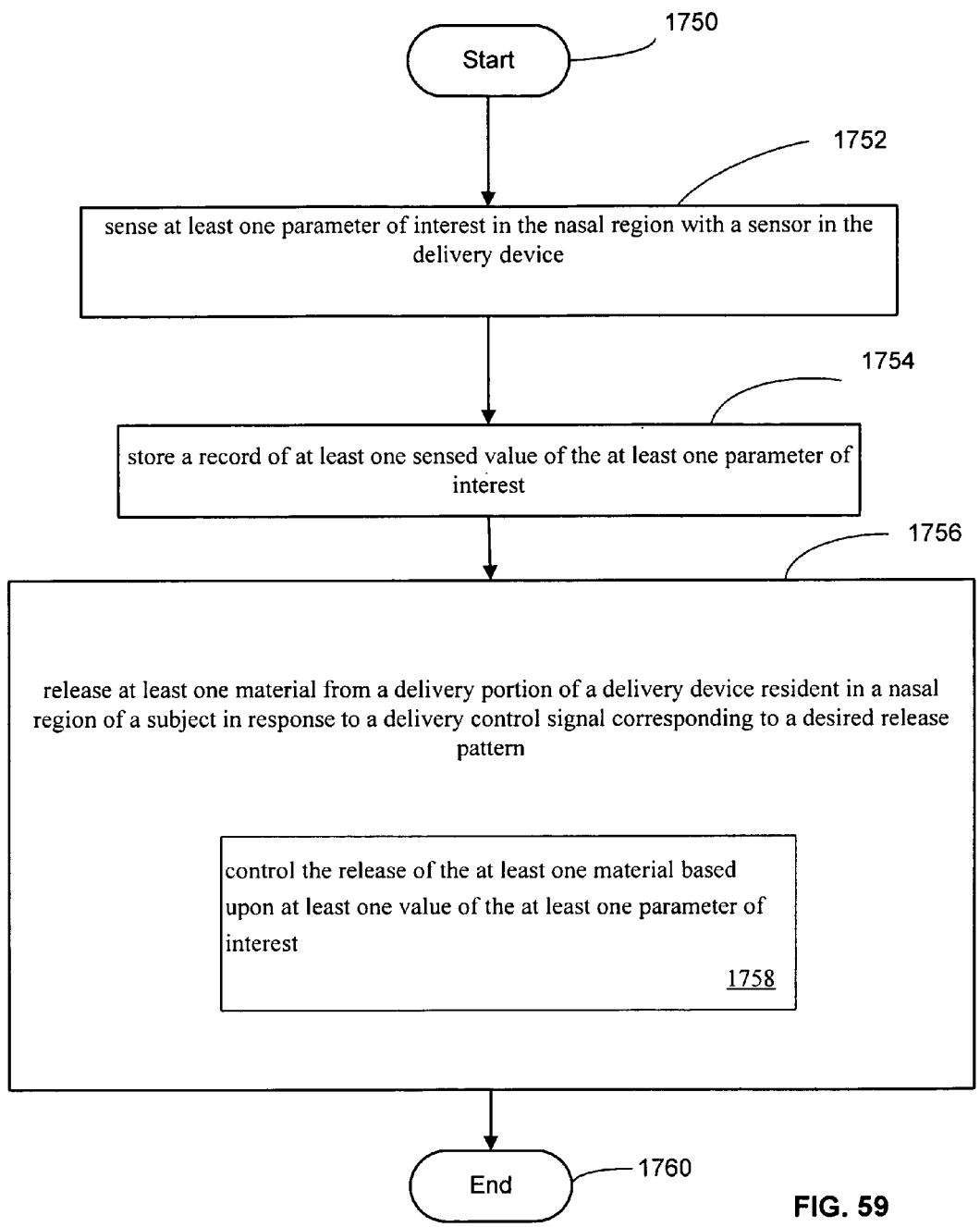
FIG. 59 is a flow diagram of a method of delivering a material to a nasal region of a subject.

As shown in FIG. 59, the method may include the steps of sensing at least one parameter of interest in the nasal region with a sensor in the delivery device at 1752, storing a record of at least one sensed value of the at least one parameter of interest at 1754, and releasing at least one material from a delivery portion of a delivery device mounted within a nasal region of a subject in response to a delivery control signal corresponding to a desired release pattern at 1756, including controlling the release of the at least one material based upon the value of the at least one parameter of interest at 1758.

Some embodiments of the method may include generating a delivery control signal at least in part as a function of the individual identity of the subject.

Figure 60:
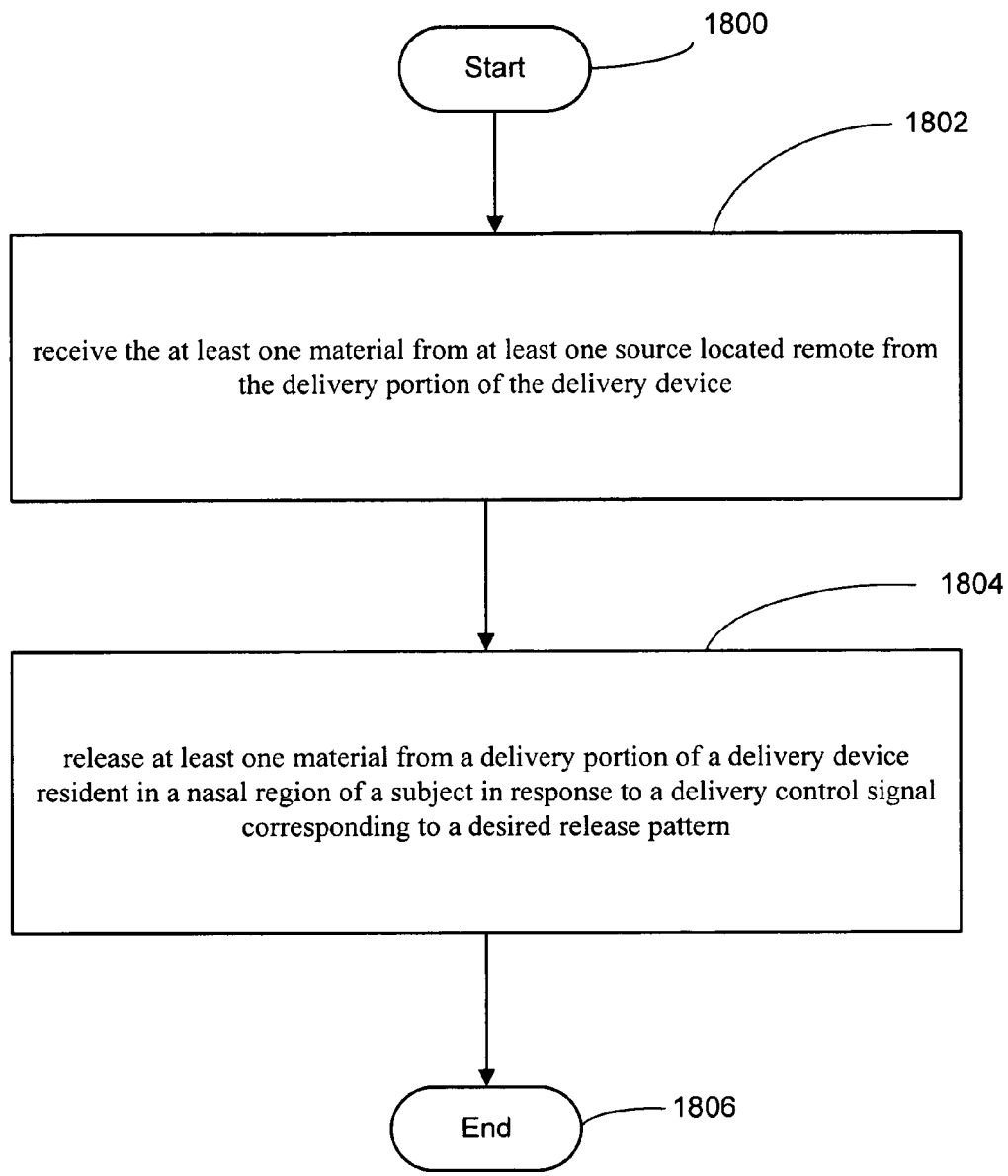
FIG. 60 is a flow diagram of a method of delivering a material to a nasal region of a subject.

As shown in FIG. 60, the method may include receiving the at least one material from at least one source located remote from the delivery portion of the delivery device at step 1802, and releasing at least one material from a delivery portion of a delivery device mounted within a nasal region of a subject in response to a delivery control signal corresponding to a desired release pattern at 1804.

Figure 61:
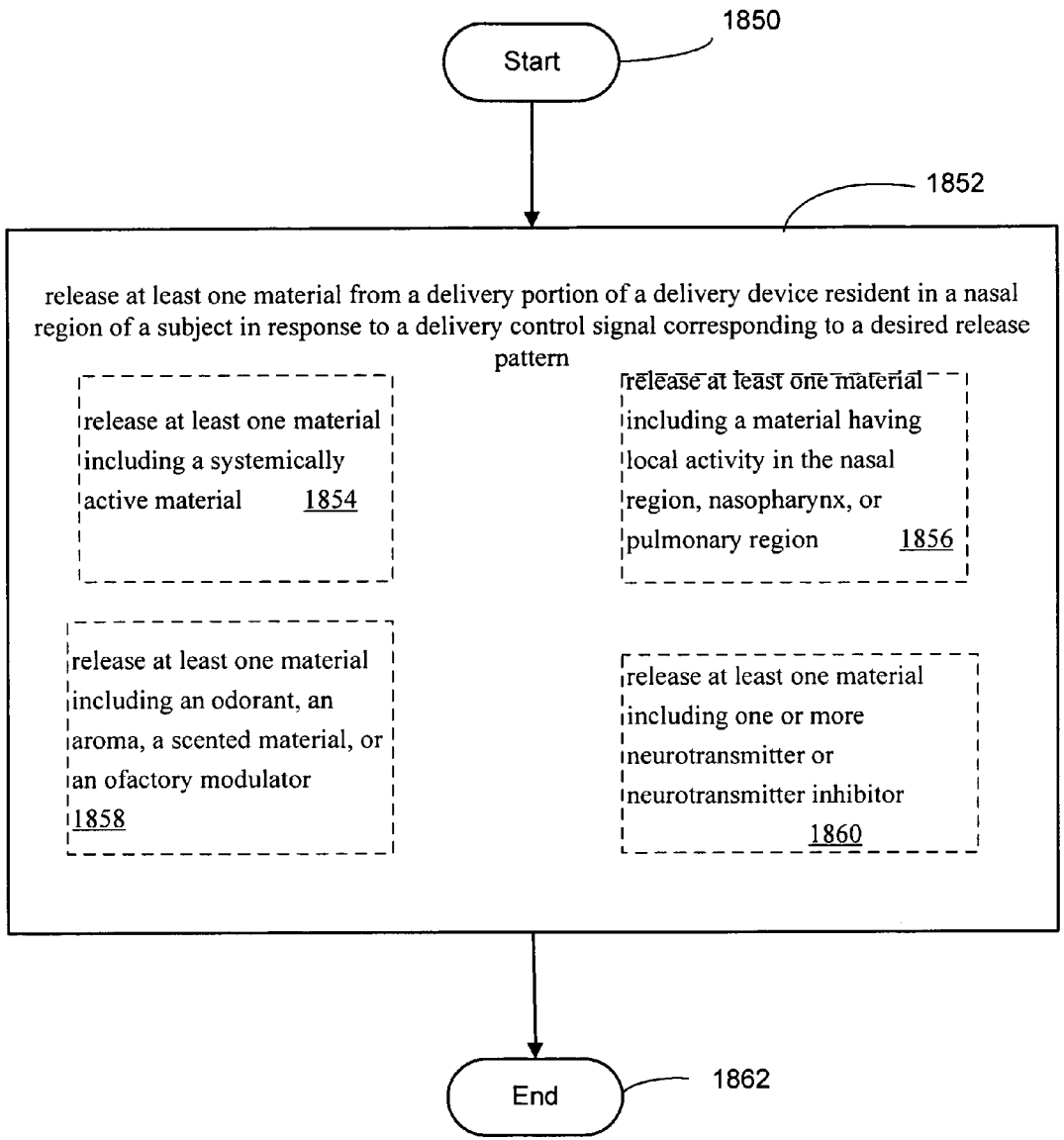
FIG. 61 is a flow diagram showing further aspects of a method of delivering a material to a nasal region of a subject.

A shown in FIG. 61, releasing at least one material from a delivery portion of a delivery device mounted within a nasal region of a subject in response to a delivery control signal corresponding to a desired release pattern at 1852 may include releasing at least one material including a systemically active material, as indicated at 1854, releasing at least one material include a material having local activity in the nasal region, nasopharynx, or pulmonary region, as indicated at 1856 releasing at least one material including an odorant, an aroma, an olfactory modulator or a scented material, as indicated at 1858, or releasing at least one material including one or more neurotransmitters or neurotransmitter inhibitors, as indicated at 1860.

Figure 62:
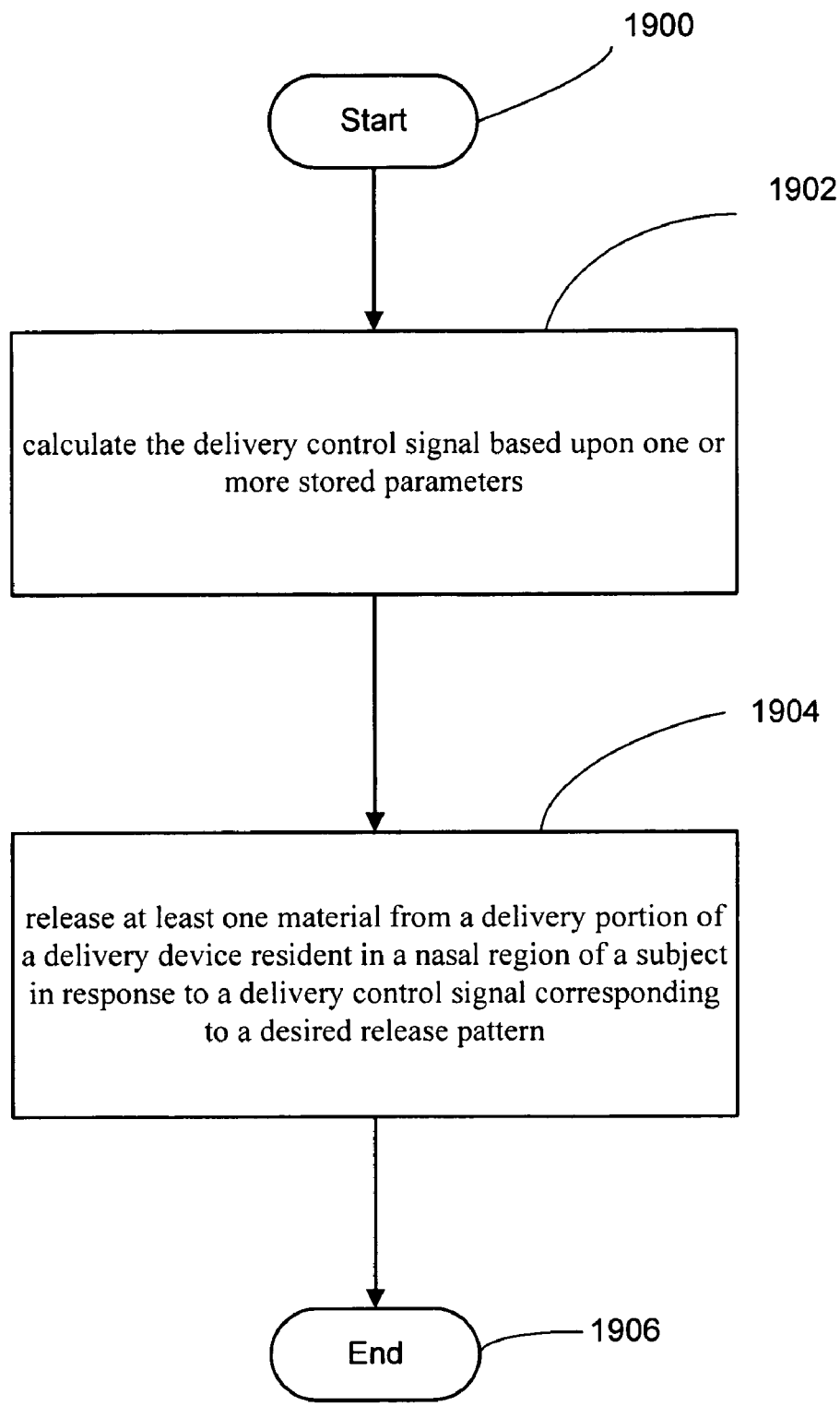
FIG. 62 is a flow diagram showing further aspects of a method of delivering a material to a nasal region of a subject.

In some embodiments, as shown in FIG. 62, the method may include calculating the delivery control signal based upon one or more stored parameters, at 1902, and releasing at least one material from a delivery portion of a delivery device mounted within a nasal region of a subject in response to the delivery control signal corresponding to a desired release pattern at 1904.

Figure 63:
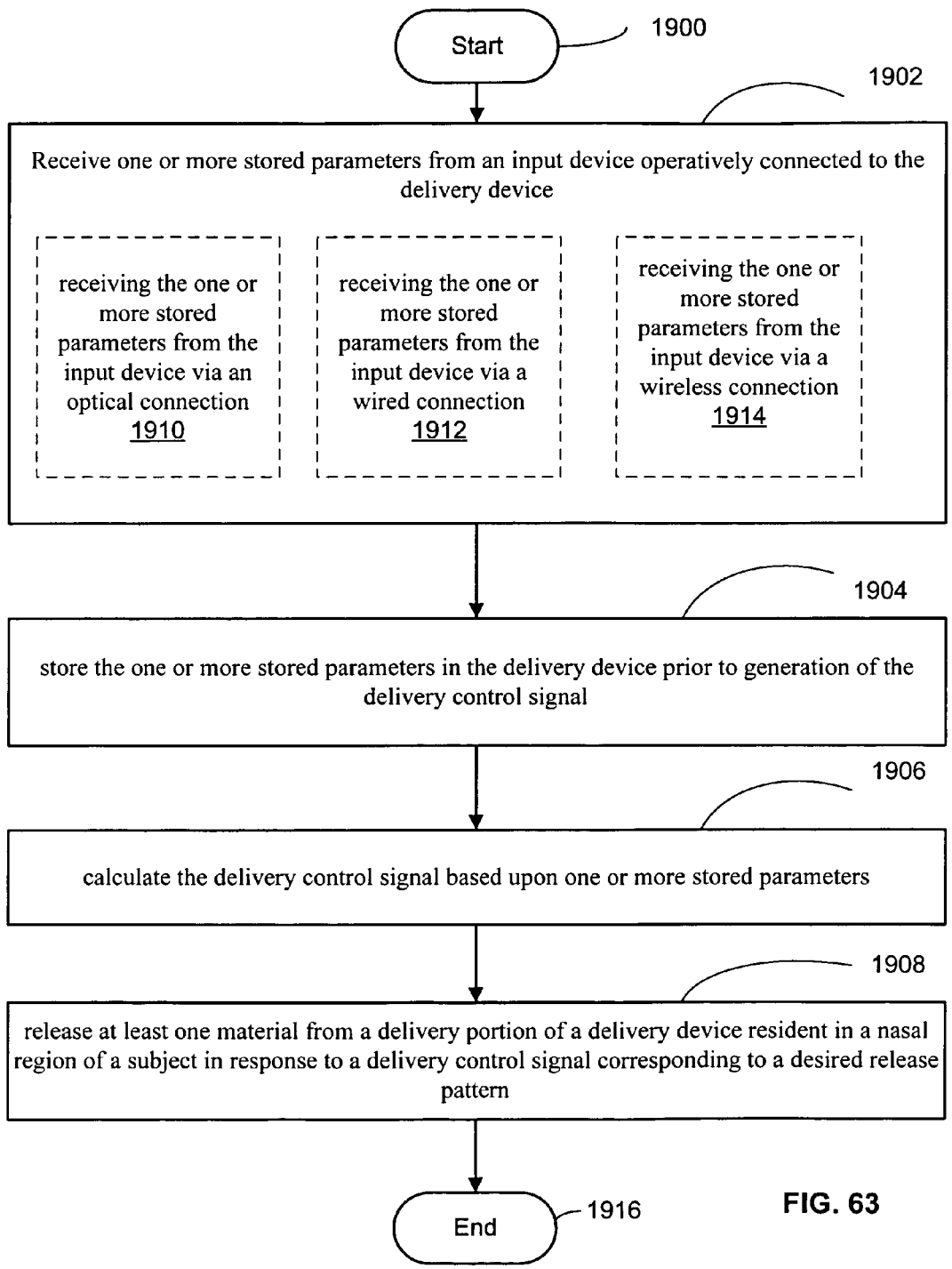
FIG. 63 is a flow diagram showing further aspects of a method of delivering a material to a nasal region of a subject.

In an embodiment as shown in FIG. 63, in addition to the steps of calculating the delivery control signal based upon one or more stored parameters, at 1906, and releasing at least one material from a delivery portion of a delivery device mounted within a nasal region of a subject in response to a delivery control signal corresponding to a desired release pattern at 1908, the method may include storing the one or more stored parameters in the delivery device prior to generation of the delivery control signal, as shown at step 1904. The one or more stored parameters may be received from an input device operatively connected to the delivery device, at step 1902. For example, the method may include receiving the one or more stored parameters from the input device via an optical connection, as shown at 1910, receiving the one or more stored parameters from the input device via a wired connection, as shown at 1912, or receiving the one or more stored parameters from the input device via a wireless connection, as shown at 1914. In other embodiments, the method may instead (or in addition) include calculating the delivery control signal based upon one or more prior values of the delivery control signal.

Figure 64:
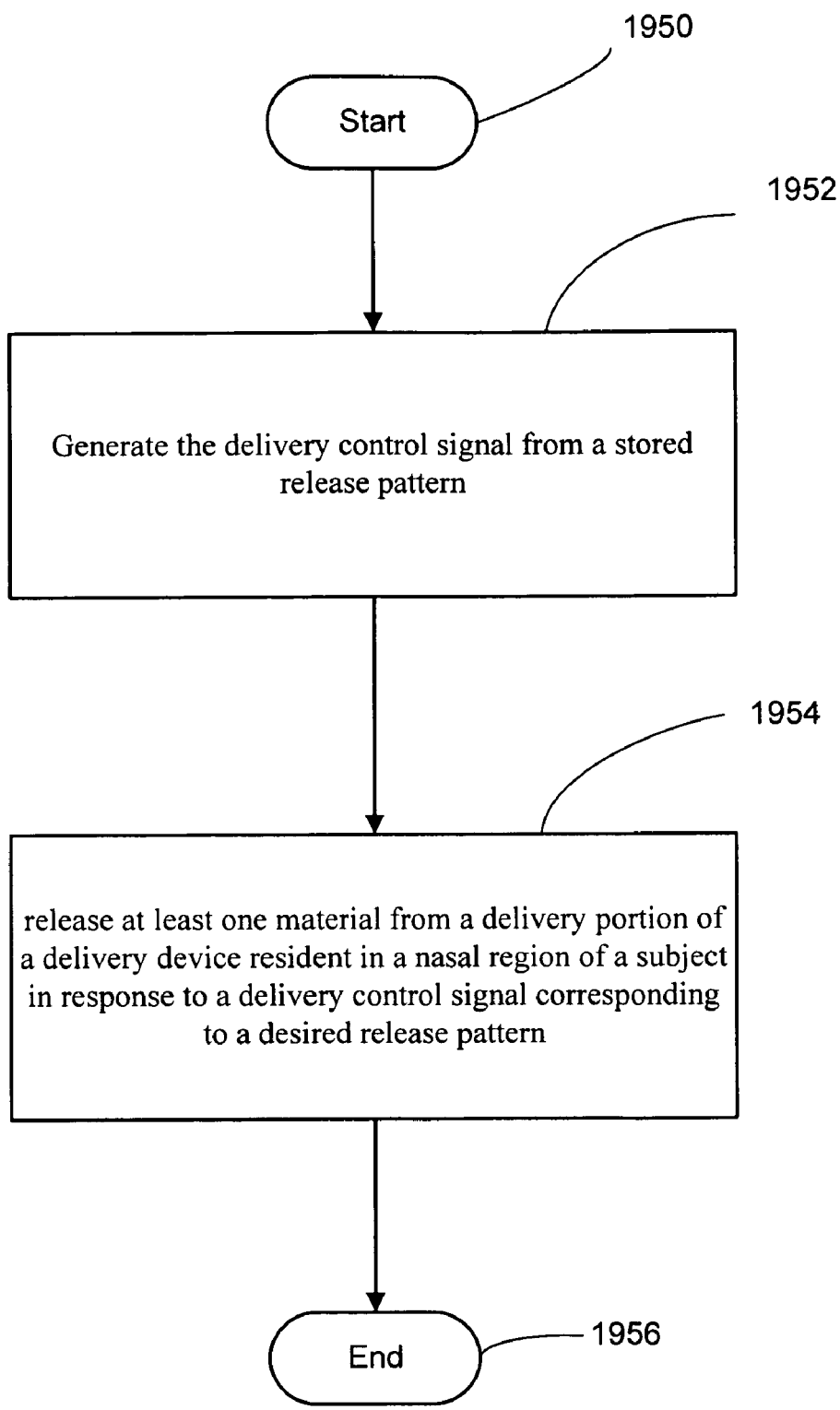
FIG. 64 is a flow diagram showing further aspects of a method of delivering a material to a nasal region of a subject.
Figure 65:
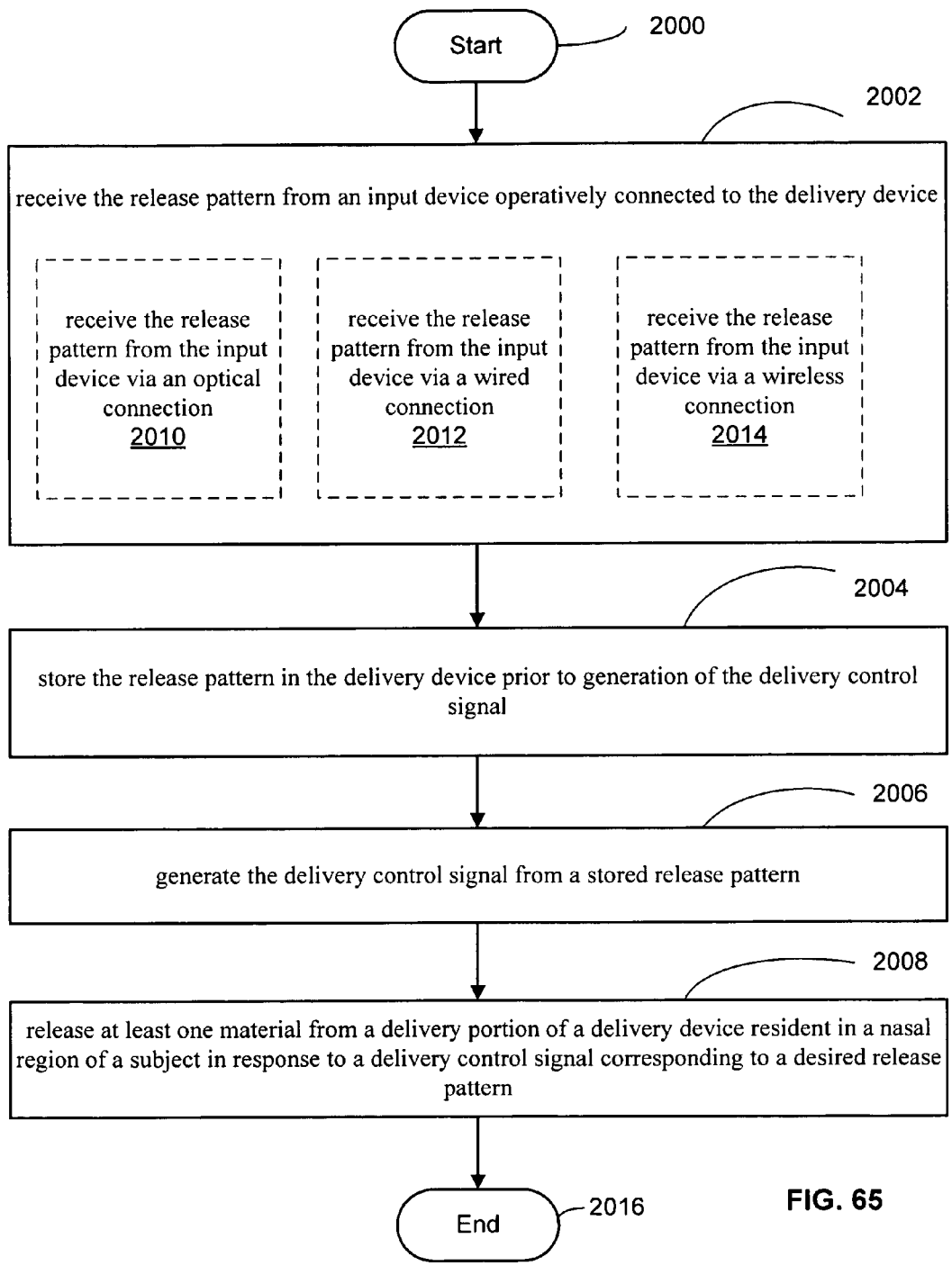
FIG. 65 is a flow diagram showing further aspects of a method of delivering a material to a nasal region of a subject.

As shown in FIG. 64, one embodiment of the method may include generating the delivery control signal from a stored release pattern, at step 1952, before releasing at least one material from a delivery portion of a delivery device mounted within a nasal region of a subject in response to a delivery control signal corresponding to a desired release pattern at step 1954. As shown in FIG. 65, in addition to generating the delivery control signal from a stored release pattern, at step 2006, and releasing at least one material from a delivery portion of a delivery device mounted within a nasal region of a subject in response to a delivery control signal corresponding to a desired release pattern at step 2008, the method may include a step of storing the release pattern in the delivery device prior to generation of the delivery control signal, at step 2004. The method may also include a step of receiving the release pattern from an input device operatively connected to the delivery device, at 2002, for example, by receiving the release pattern from the input device via an optical connection, as indicated at 2010, receiving the release pattern from the input device via a wired connection, as indicated at 2012, or receiving the release pattern from the input device via a wireless connection, as indicated at 2014.

Methods of using devices and systems as described herein may include not only the use of the device while it is mounted within the nasal region of a subject, but may also include steps of mounting at least a portion of the delivery device within the nasal region of the subject, and optionally, removing at least a portion of the delivery portion of the delivery device from the nasal region of the subject following a use period. It will be appreciated that for short use periods, a method may include mounting at least a portion of the delivery device within the nasal region of the subject prior to releasing the at least one material from the delivery portion of the delivery device and removing at least the delivery portion of the delivery device from the nasal region of the subject following a use period. On the other hand, in applications where the device is mounted in the nasal region of the subject substantially permanently, the device may be mounted in the nasal region, and no steps taken to remove the device. In some cases, the device may be mounted manually, by the subject, or by someone acting on behalf of the subject, for example a medical care provider. In some cases, the emplacement of the device within the nasal region may performed with the use of an installation device, such as a tool that will hold the device to allow it to be inserted into portions of the nasal region that would otherwise be inaccessible. Local or general anesthetic may be provided in certain cases, as appropriate to provide for the comfort of the subject.

Figure 66:
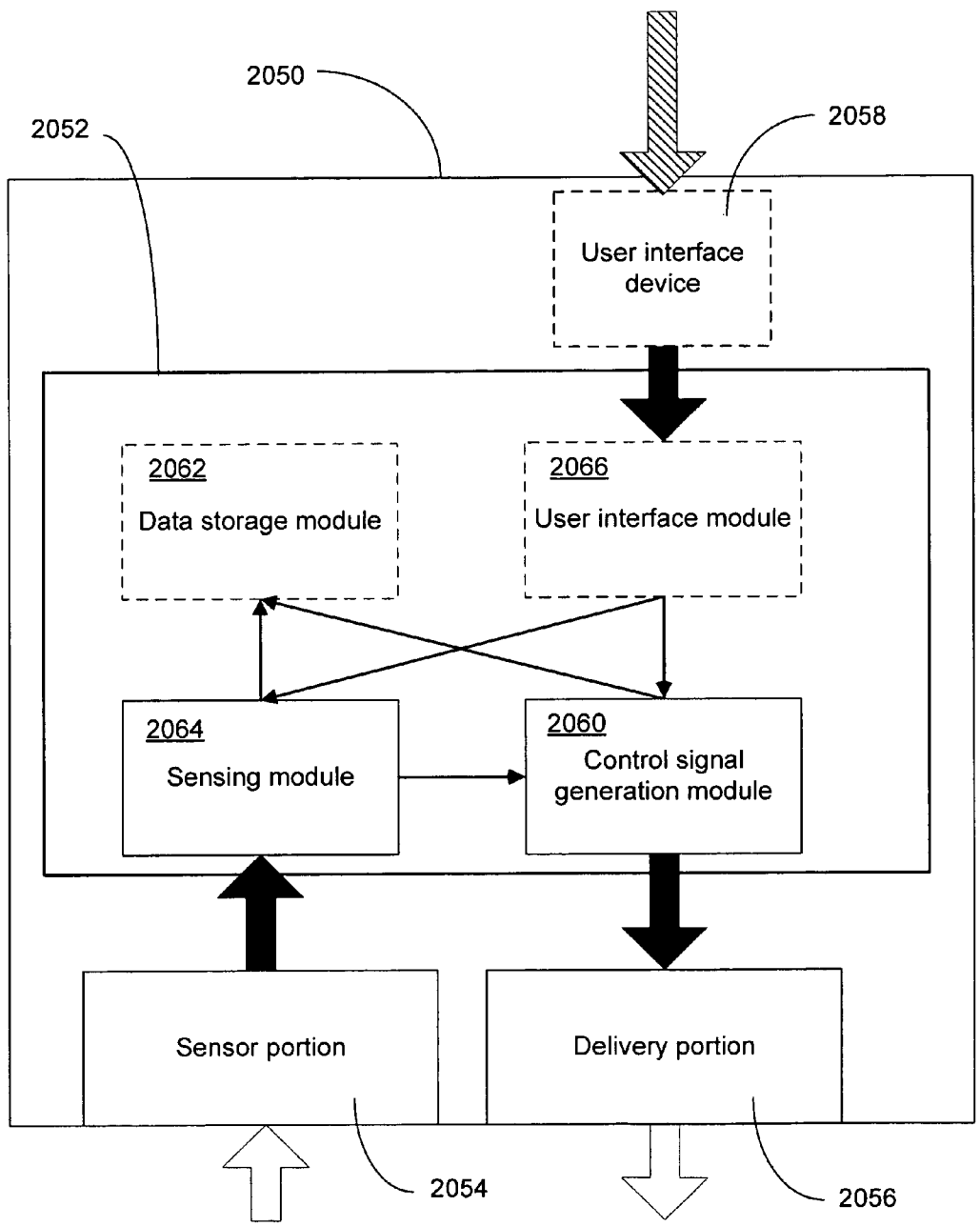
FIG. 66 is a schematic diagram of software for controlling release of a material from device mounted within a nasal region of a subject.

According to various embodiments, a controllable release nasal system may include software for controlling the release of material from a delivery device mounted within a nasal region of a subject. Such software is illustrated in a block diagram in FIG. 66. The basic components of the controllable release nasal system 2050 may include software 2052, at least one sensor 2054, a delivery portion 2056, and a user input device 2058. Non-software components are described elsewhere herein. Software 2052 may include a control signal generation module 2060 capable of generating a delivery control signal corresponding to a desired pattern of delivery of a material into a nasal region of a subject from a delivery portion of the delivery device mounted within the nasal region of the subject, according to a model of the entire system. Software 2052 may include at least one of a data storage module 2062 capable of storing pattern data or pattern parameters representing the desired pattern of delivery of the material into the nasal region of the subject or a sensing module 2064 capable of receiving and processing a sense signal from a sensor portion of the delivery device, wherein the control signal generation module is configured to generate the delivery control signal based upon at least one of the pattern data, pattern parameters or sense signal, generally proceeding according to a model. In another aspect, the software may include both a data storage module 2062 capable of controlling storage of pattern data or pattern parameters representing the desired pattern of delivery of the material into the nasal region of the subject according to a model and a sensing module 2064 capable of receiving and processing a sense signal from a sensor portion 2054 of the delivery device.

Data storage module 2062 may be capable of storing a sense signal received from the sensing module 2064. The sense signal may be a processed sense signal from the sensor portion 2054 of the delivery device. The software may include a data storage module 2062 configured to store one or more values from the delivery device. At least a portion of the one or more values may be sense signal values received from the sensing module 2064. Alternatively, or in addition, at least a portion of the one or more values are sense parameters received from the sensing module 2064. In some embodiments, at least a portion of the one or more values may be delivery control signal values from the control signal generation module 2060.

In another aspect, the software may include a user interface module 2066 configured to receive user input of one or more user-enterable parameters from a user interface device. The software may include a user interface module 2066 configured to receive user input of a desired delivery pattern from a user interface device 2058. In some embodiments, the user interface module may be configured to receive the desired delivery pattern in the form of a digital data transmission.

The software may include a sensing module 2064 capable of receiving and processing a sense signal from a sensor portion 2054 of the delivery device. The sensing module 2064 may be capable of processing the sense signal by various signal processing methods as are known to those of skill in the art, including, but not limited to filtering, windowing, noise reduction, signal averaging, feature detection, time-domain analysis, frequency domain analysis, feature extraction, comparison of the sense signal with, e.g., a template sense signal, sorting, data reduction, or endpoint determination.

In some embodiments, the control signal generation module 2060 may be capable of generating the delivery control signal by calculating the delivery control signal based upon one or more stored parameters. In some embodiments, at least a portion of the stored parameters may be specific to the subject, relating to size, weight, age, gender, medical or health status, and so forth. The control signal generation module 2060 may be capable of generating the delivery control signal from a stored release pattern. The parameters or release pattern may be stored in a data storage location under the control of data storage module 2062.

Delivery devices and systems as described herein may be operated under the control of software. Certain components of system 2050 may be primarily hardware-based, e.g., sensor portion 2054, delivery portion 2056, and, optionally, user interface device 2058. Hardware-based devices may include components that are electrical, mechanical, chemical, optical, electromechanical, electrochemical, electro-optical, and are not limited to the specific examples presented herein. Control signal generation module 2060, data storage module 2062, sensing module 2064, and use interface module 2066 may be all or mostly software-based; however, it will be appreciated that various operations may be performed in hardware, software, firmware, or various combinations thereof.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof and a wide range of components that may impart mechanical force or motion such as rigid bodies, spring or torsional bodies, hydraulics, and electromagnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will recognize that electro-mechanical as used herein is not necessarily limited to a system that has both electrical and mechanical actuation except as context may dictate otherwise. Non-electrical analogs of electrical circuitry may include fluid circuitry, electro-mechanical circuitry, mechanical circuitry, and various combinations thereof.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A controllable release nasal system, comprising:
    a structural element including at least one positioning portion configured for contacting an interior surface of a nasal region and mounting the structural element within the nasal region of a subject;
    a delivery portion mounted relative to the structural element and configured to release at least one material responsive to a delivery control signal; and
    control signal generation circuitry configured to generate a delivery control signal corresponding to a desired pattern of release of the at least one material into the nasal region.

2. The system of claim 1, wherein the controllable release nasal system is configured to reside entirely within the nasal region of the subject.

3. The system of claim 1, wherein the structural element includes a self-expanding structure configured to expand to mount the structural element within the nasal region of the subject.

4. The system of claim 1, wherein the delivery portion is configured to release the at least one material directly into the nasal mucosa for absorption.

5. The system of claim 4, wherein the delivery portion includes a permeation enhancer capable of increasing the permeation of the at least one material into the nasal mucosa.

6. The system of claim 1, wherein the delivery portion is configured to release the at least one material into the nasal cavity.

7. The system of claim 6, wherein the delivery portion is configured to direct the release of the at least one material toward a location selected from the nasal mucosa, the olfactory portion of the nasal mucosa, and the nasopharynx.

8. The system of claim 1, including a source of the at least one material, the source connected to the delivery portion.

9. The system of claim 8, wherein the source is located at one of a location in or on the structural element or a location external to the nasal region of the subject and connected to the delivery portion via a delivery tube that enters the nasal region of the subject via a Nostril of the subject.

10. The system of claim 1, wherein the positioning portion includes at least one of a clip structure, at least a portion of which is configured to extend outside the nasal region of the subject; an adhesive; one or more barb-like structures; a vacuum-generating device; or a hair-engaging structure.

11. The system of claim 1, wherein at least a part of the structural element is configured for mounting within one of a Nostril of the subject or a nasal cavity of the subject.

12. The system of claim 1, including:
 a power source;
 a sensor capable of detecting or measuring a parameter of interest in the nasal region of the subject;
 a memory location; and
 a source of the at least one material, the source connected to the delivery portion.

13. A method of delivering a material to the nasal region of a subject, comprising:
releasing at least one material from a delivery portion of a delivery device mounted within a nasal region of a subject in response to a delivery control signal corresponding to a desired release pattern.

14. The method of claim 13, including generating a delivery control signal at least in part as a function of the individual identity of the subject.

15. The method of claim 13, including releasing at least one material including one or more odorant, aroma, scented material, olfactory modulator, neurotransmitter or neurotransmitter inhibitor.

16. The method of claim 13, including at least one of mounting at least a portion of the delivery device within the nasal region of the subject or removing at least a portion of the delivery portion of the delivery device from the nasal region of the subject following a use period.

* * * * *